United States Patent
Hauser et al.

(10) Patent No.: US 11,207,623 B2
(45) Date of Patent: Dec. 28, 2021

(54) HYDROCARBON FLUID-WATER SEPARATION

(71) Applicant: DONALDSON COMPANY, INC., Minneapolis, MN (US)

(72) Inventors: Bradly G. Hauser, Minneapolis, MN (US); Stephen K. Sontag, Maple Grove, MN (US); Davis B. Moravec, Burnsville, MN (US); Stuti S. Rajgarhia, Bloomington, MN (US); Andrew J. Dallas, Lakeville, MN (US); Vijay K. Kapoor, Eagan, MN (US); Aflal Rahmathullah, Savage, MN (US); Charles S. Christ, Deephaven, MN (US); Joseph M. Block, Carver, MN (US)

(73) Assignee: Donaldson Company, Inc., Minneapolis, MN (US)

( * ) Notice: Subject to any disclaimer, the term of this patent is extended or adjusted under 35 U.S.C. 154(b) by 151 days.

(21) Appl. No.: 16/425,371

(22) Filed: May 29, 2019

(65) Prior Publication Data
US 2019/0314745 A1 Oct. 17, 2019

Related U.S. Application Data

(63) Continuation of application No. 15/678,840, filed on Aug. 16, 2017, now Pat. No. 10,315,140.
(Continued)

(51) Int. Cl.
*B01D 39/16* (2006.01)
*B01D 39/10* (2006.01)
(Continued)

(52) U.S. Cl.
CPC ......... *B01D 39/1623* (2013.01); *B01D 39/16* (2013.01); *B01D 39/1607* (2013.01);
(Continued)

(58) Field of Classification Search
CPC ............... B01D 39/16; B01D 39/1607; B01D 39/1615; B01D 39/1623; B01D 39/20;
(Continued)

(56) References Cited

U.S. PATENT DOCUMENTS

| | | | |
|---|---|---|---|
| 2,933,154 | A | 4/1960 | Lauterbach |
| 3,228,527 | A | 1/1966 | McPherson |

(Continued)

FOREIGN PATENT DOCUMENTS

| | | |
|---|---|---|
| CN | 102665844 | 9/2012 |
| CN | 103108689 | 5/2013 |

(Continued)

OTHER PUBLICATIONS

U.S. Appl. No. 62/543,456, filed Aug. 10, 2017, Donaldson Company, Inc.
(Continued)

*Primary Examiner* — John Kim
(74) *Attorney, Agent, or Firm* — Mueting Raasch Group

(57) ABSTRACT

A substrate for use in a filter media including, for example, in a hydrocarbon fluid-water separation filter; methods of identifying the substrate; methods of making the substrate; methods of using the substrate; and methods of improving the roll off angle of the substrate. In some embodiments, the substrate includes a hydrophilic group-containing polymer or a hydrophilic group-containing polymer coating.

20 Claims, 19 Drawing Sheets

Related U.S. Application Data

(60) Provisional application No. 62/375,772, filed on Aug. 16, 2016, provisional application No. 62/375,768, filed on Aug. 16, 2016.

(51) Int. Cl.

| | | |
|---|---|---|
| *C01B 13/10* | (2006.01) | |
| *C07C 15/06* | (2006.01) | |
| *C08G 65/34* | (2006.01) | |
| *B01D 69/10* | (2006.01) | |
| *B01D 69/12* | (2006.01) | |
| *B01D 39/20* | (2006.01) | |
| *C01B 13/02* | (2006.01) | |

(52) U.S. Cl.
CPC ......... *B01D 39/1615* (2013.01); *B01D 39/20* (2013.01); *B01D 39/2003* (2013.01); *B01D 69/10* (2013.01); *B01D 69/12* (2013.01); *C01B 13/10* (2013.01); *C07C 15/06* (2013.01); *C08G 65/34* (2013.01); *B01D 2239/0421* (2013.01); *B01D 2239/0428* (2013.01); *B01D 2239/10* (2013.01); *B01D 2239/1216* (2013.01); *C01B 13/0214* (2013.01); *C08F 2810/20* (2013.01); *C08G 2650/20* (2013.01); *Y10S 210/05* (2013.01)

(58) Field of Classification Search
CPC ................ B01D 39/2003; B01D 69/10; B01D 2239/0421; B01D 2239/0428; B01D 2239/10; B01D 2239/1216; C01B 13/0214; C01B 13/10; C07C 15/06; C08G 65/34; C08G 2650/20; Y10S 210/05; C08F 2810/20
See application file for complete search history.

(56) References Cited

U.S. PATENT DOCUMENTS

| | | |
|---|---|---|
| 3,231,091 A | 1/1966 | Kingsbury et al. |
| 5,137,633 A | 8/1992 | Wang |
| 5,269,925 A | 12/1993 | Broadhurst |
| 5,443,724 A | 8/1995 | Williamson et al. |
| 5,997,739 A | 12/1999 | Clausen et al. |
| 6,422,396 B1 | 7/2002 | Li et al. |
| 6,569,330 B1 | 5/2003 | Sprenger et al. |
| 7,115,150 B2 | 10/2006 | Johnson et al. |
| 7,147,110 B2 | 12/2006 | Clausen et al. |
| 7,527,739 B2 | 5/2009 | Jiang et al. |
| 7,628,917 B2 | 12/2009 | Penezina et al. |
| 7,635,435 B2 | 12/2009 | Benachenhou |
| 7,824,550 B2 | 11/2010 | Abreu et al. |
| 7,846,242 B2 | 12/2010 | Paling et al. |
| 8,017,011 B2 | 9/2011 | Ellis et al. |
| 8,114,291 B2 | 2/2012 | Ellis et al. |
| 8,356,717 B2 | 1/2013 | Waller, Jr. et al. |
| 8,360,251 B2 | 1/2013 | Wieczorek et al. |
| 8,545,589 B2 | 10/2013 | Rocklitz et al. |
| 8,590,712 B2 | 11/2013 | Wieczorek et al. |
| 9,186,602 B2 | 11/2015 | Rathod et al. |
| 9,823,174 B2 | 11/2017 | Kota et al. |
| 10,023,751 B2 | 7/2018 | Hu et al. |
| 10,315,140 B2 | 6/2019 | Hauser et al. |
| 2003/0010002 A1 | 1/2003 | Johnson et al. |
| 2006/0207234 A1 | 9/2006 | Ward et al. |
| 2006/0242933 A1 | 11/2006 | Webb et al. |
| 2008/0029623 A1 | 2/2008 | Sugiyama et al. |
| 2010/0050871 A1 | 3/2010 | Moy et al. |
| 2011/0198280 A1 | 8/2011 | Jones et al. |
| 2012/0107851 A1 | 5/2012 | Killard et al. |
| 2012/0168359 A1 | 7/2012 | Marshall et al. |
| 2013/0029048 A1 | 1/2013 | Goscha et al. |
| 2013/0032316 A1 | 2/2013 | Dhiman et al. |
| 2013/0109262 A1 | 5/2013 | Zhou |
| 2013/0248436 A1 | 9/2013 | Hacker et al. |
| 2013/0309509 A1 | 11/2013 | Shibuya et al. |
| 2013/0334130 A1* | 12/2013 | Ganguli ................ B01D 65/08 210/500.29 |
| 2013/0341290 A1 | 12/2013 | Yu et al. |
| 2014/0069862 A1* | 3/2014 | Guo ........................ B01D 71/26 210/500.29 |
| 2014/0178611 A1 | 6/2014 | Smith et al. |
| 2014/0197090 A1 | 7/2014 | Popoff et al. |
| 2014/0208703 A1 | 7/2014 | Willems et al. |
| 2014/0275692 A1 | 9/2014 | Patel et al. |
| 2014/0284263 A1 | 9/2014 | Duerr et al. |
| 2014/0284264 A1 | 9/2014 | Klein et al. |
| 2014/0314975 A1 | 10/2014 | Smith et al. |
| 2015/0290561 A1 | 10/2015 | Barsness et al. |
| 2015/0308393 A1 | 10/2015 | Boiger et al. |
| 2015/0328565 A1 | 11/2015 | Swaminathan et al. |
| 2016/0047062 A1 | 2/2016 | Greenawalt |
| 2016/0081541 A1 | 3/2016 | Yasue |
| 2017/0000223 A1 | 1/2017 | Lynn et al. |
| 2018/0050293 A1 | 5/2018 | Hauser et al. |
| 2018/0117797 A1 | 5/2018 | Shin et al. |
| 2018/0147604 A1 | 5/2018 | Dai et al. |
| 2018/0169551 A1 | 6/2018 | Jaganathan et al. |
| 2019/0314745 A1 | 10/2019 | Hauser et al. |
| 2021/0016214 A1 | 1/2021 | Rahmathullah et al. |
| 2021/0060456 A1 | 3/2021 | Rahmathullah et al. |
| 2021/0106935 A1 | 4/2021 | Rahmathullah et al. |

FOREIGN PATENT DOCUMENTS

| | | |
|---|---|---|
| CN | 104857742 | 8/2015 |
| EP | 1 740 287 A1 | 1/2007 |
| GB | 752029 | 7/1956 |
| GB | 1064065 A | 4/1967 |
| GB | 1107607 A | 3/1968 |
| JP | 2005-537129 | 12/2005 |
| JP | 2014-198294 | 10/2014 |
| JP | 2015-039685 | 3/2015 |
| JP | 2015-081521 | 4/2015 |
| WO | 96/37290 | 11/1996 |
| WO | 2007/041559 | 4/2007 |
| WO | 2009/100067 | 8/2009 |
| WO | 2011/042605 | 4/2011 |
| WO | 2011/091432 | 7/2011 |
| WO | WO 2011/127479 A1 | 10/2011 |
| WO | 2012/099125 | 7/2012 |
| WO | WO 2013/155427 A1 | 10/2013 |
| WO | WO 2014/144536 A1 | 9/2014 |
| WO | WO 2015/175877 A1 | 11/2015 |
| WO | 2016/081541 | 5/2016 |
| WO | 2018/035235 | 2/2018 |
| WO | 2019/032773 | 2/2019 |
| WO | 2019/040324 | 2/2019 |
| WO | 2019/161108 | 8/2019 |
| WO | 2019/161110 | 8/2019 |
| WO | 2019/161111 | 8/2019 |

OTHER PUBLICATIONS

International Patent Application No. PCT/US2017/047162, filed Aug. 16, 2017; International Search Report and Written Opinion dated Nov. 27, 2017, 13 pages.

ASTM-D6751-15C, "Standard Specification for Biodiesel Fuel Blend Stock (B100) for Middle Distillate Fuels", ASTM International, West Conshohocken, Pennsylvania, Jan. 2016, 11 pages.

ASTM-D975-17A, "Standard Specification for Diesel Fuel Oils", ASTM International, West Conshohocken, Pennsylvania, Jan. 2018, 28 pages.

Chunglok, "Extreme Wetting-Resistant Multiscale Nano-/Microstructured Surfaces for Viscoelastic Liquid Repellence," *Journal of Nanomaterials*, 2016, vol. 2016, Article ID 9510156, 13 pages.

ISO/TS 16332 Technical Specification, "Diesel engines—Fuel filters—Method for evaluation fuel/water separation efficiency, First Edition," ISO, Geneva, Switzerland, Sep. 15, 2006, 32 pages.

(56) References Cited

OTHER PUBLICATIONS

Feng, et al., "Petal Effect: A Superhydrophobic State with High Adhesive Force", *Langmuir*, 2008, 24(8):4114-4119. Published online Mar. 1, 2008.
Miwa, et al., "Effects of the Surface Roughness on Sliding Angles of Water Droplets on Superhydrophobic Surfaces", *Langmuir*, 2000, 16(13):5754-5760. Published online May 27, 2000.
Wolfram, et al., Chapter 10, "Wetting, Spreading, and Contact Angle," in *Welting, Spreading, and Adhesion*, Padday, J. F., ed.; Academic Press: London, 1978, 237-238.
International Patent Application No. PCT/US2019/018082, filed Feb. 14, 2019, International Preliminary Report on Patentability dated Aug. 18, 2020, 12 pages.
International Patent Application No. PCT/US2019/018082, filed Feb. 14, 2019, International Search Report and Written Opinion, dated Jul. 15, 2019, 18 pages.
International Patent Application No. PCT/US2019/018082, filed Feb. 14, 2019, Invitation to Pay Additional Fees and Partial Search Report, dated May 6, 2019, 13 pages.
International Patent Application No. PCT/US2019/018083, filed Feb. 14, 2019, International Preliminary Report on Patentability dated Aug. 18, 2020, 12 pages.
International Patent Application No. PCT/US2019/018083, filed Feb. 14, 2019, International Search Report and Written Opinion, dated Jul. 15, 2019, 19 pages.
International Patent Application No. PCT/US2019/018083, filed Feb. 14, 2019, Invitation to Pay Additional Fees and Partial Search Report, dated May 13, 2019, 14 pages.
International Patent Application No. PCT/US2019/018080, filed Feb. 14, 2019, International Preliminary Report on Patentability dated Aug. 18, 2020, 11 pages.
International Patent Application No. PCT/US20190/18080, filed Feb. 14, 2019, International Search Report and Written Opinion, dated Jul. 15, 2019, 17 pages.
International Patent Application No. PCT/US2019/018080, filed Feb. 14, 2019, Invitation to Pay Additional Fees and Partial Search Report, dated May 13, 2019, 12 pages.
International Patent Application No. PCT/US2017/047162, filed Aug. 16, 2017, International Preliminary Report on Patentability, dated Feb. 19, 2019, 7 pages.

* cited by examiner

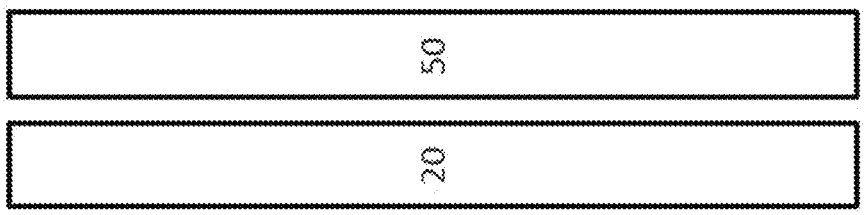
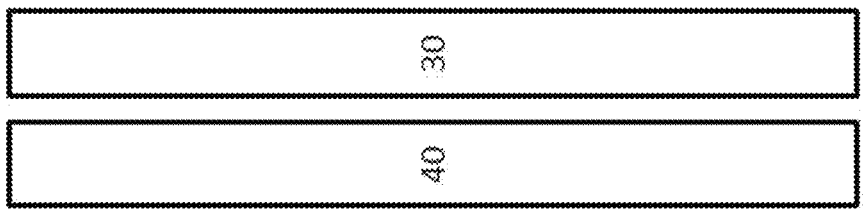
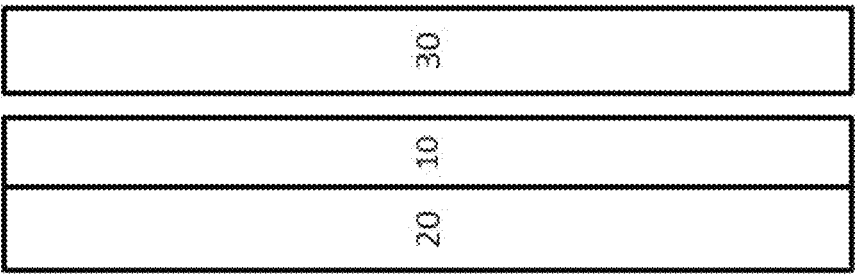
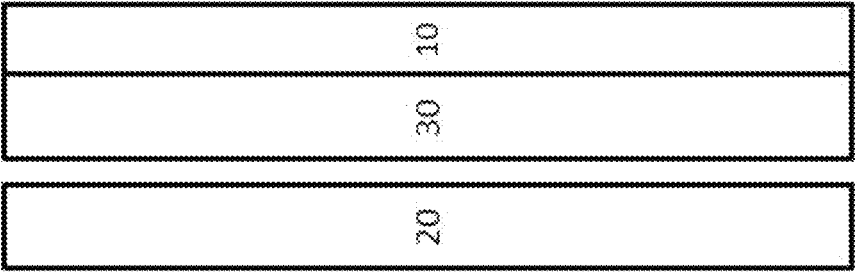

HYDROCARBON FLUID-WATER SEPARATION

CONTINUING APPLICATION DATA

This application is a continuation application of U.S. patent application Ser. No. 15/678,840, filed Aug. 16, 2017, which claims the benefit of U.S. Provisional Application Ser. No. 62/375,768, filed Aug. 16, 2016, and U.S. Provisional Application Ser. No. 62/375,772, filed Aug. 16, 2016, each of which is incorporated by reference herein.

BACKGROUND

Filtration of hydrocarbon fluids including diesel fuels for use in internal combustion engines is often essential to proper engine performance. Water and particle removal can be necessary to provide favorable engine performance as well as to protect engine components from damage. Free water (that is, non-dissolved water), which exists as a separate phase in the hydrocarbon fluid, can, if not removed, cause problems including damage to engine components through cavitation, corrosion, or promotion of microbiological growth.

SUMMARY OF THE INVENTION

This disclosure describes a substrate for use in a filter media including, for example, in a hydrocarbon fluid-water separation filter; methods of identifying the substrate; methods of making the substrate; methods of using the substrate; and methods of improving the roll off angle of the substrate. The hydrocarbon fluid can include fuel including, for example, diesel fuel. The substrate can be identified or modified based on the roll off angle (that is, the adhesion) of a water droplet on a hydrophobic surface of the substrate (that is, a surface having a contact angle of at least 90 degrees) when the surface is immersed in toluene. As described herein, the roll off angle of the water droplet on a hydrophobic surface of a substrate when the surface is immersed in toluene correlates with the ability of a substrate to remove water from hydrocarbon fluid.

In one aspect, this disclosure describes a filter media including a substrate. In some embodiments, the substrate includes a surface having a roll off angle in a range of 50 degrees to 90 degrees and a contact angle in a range of 90 degrees to 180 degrees for a 20 microliter (μL) water droplet when the surface is immersed in toluene. In some embodiments, the surface has a roll off angle in a range of 40 degrees to 90 degrees and a contact angle in a range of 90 degrees to 180 degrees for a 50 μL water droplet when the surface is immersed in toluene. In some embodiments, the surface is a UV-treated surface including, for example, a UV-oxygen treated surface. In some embodiments, the substrate includes a surface that has a hydrophilic group-containing polymer disposed thereon.

In a further aspect, this disclosure describes a filter element including a filter media including a substrate. In some embodiments, the substrate includes a surface having a roll off angle in a range of 50 degrees to 90 degrees and a contact angle in a range of 90 degrees to 180 degrees for a 20 μL water droplet when the surface is immersed in toluene. In some embodiments, the substrate includes a surface having a roll off angle of 40 degrees to 90 degrees and a contact angle in a range of 90 degrees to 180 degrees for a 50 μL water droplet when the surface is immersed in toluene.

In another aspect, this disclosure describes a method of treating a material that includes a surface. The method includes treating the surface to form a treated surface. In some embodiments, the treated surface has a roll off angle in a range of 50 degrees to 90 degrees and a contact angle in a range of 90 degrees to 180 degrees for a 20 μL water droplet when the surface is immersed in toluene. In some embodiments, the treated surface has a roll off angle in a range of 40 degrees to 90 degrees and a contact angle in a range of 90 degrees to 180 degrees for a 50 μL water droplet when the surface is immersed in toluene. In some embodiments, the method includes exposing a surface of the substrate to UV radiation. In some embodiments, the method includes disposing a hydrophilic group-containing polymer on a surface of the substrate.

In yet another aspect, this disclosure describes a method for identifying a material suitable for hydrocarbon fluid-water separation. The method includes determining the roll off angle of a droplet on a surface of the material, wherein the material is immersed in a fluid including a hydrocarbon, and wherein the roll off angle is in a range of 40 degrees to 90 degrees. In some embodiments, the fluid including a hydrocarbon includes toluene.

In further aspects, this disclosure describes the use of UV radiation to improve the roll off angle of a substrate, the use of a substance obtainable by exposure of at least one of an aromatic component and an unsaturated component to UV radiation to improve the roll off angle of a substrate, and the use of a hydrophilic group-containing polymer or a hydrophilic polymer to improve the roll off angle of a substrate.

As used here, the term "chemically distinct" means that two compounds have different chemical compositions.

As used herein, the term "hydrophilic" refers to the ability of a molecule or other molecular entity to dissolve in water, and the term "hydrophile" refers to a molecule or other molecular entity which is hydrophilic and/or that is attracted to, and tends to be miscible with or soluble in water. In some embodiments, "hydrophilic" means that, to the extent saturation has not been reached, at least 90% of the molecules or other molecular entities, preferably at least 95% of the molecules or other molecular entities, more preferably at least 97% of the molecules or other molecular entities, and most preferably at least 99% of the molecules or other molecular entities dissolve in water at 25 degrees Celsius (° C.). In some embodiments, "hydrophile" means that, to the extent saturation has not been reached, at least 90% of the molecules or other molecular entities, preferably at least 95% of the molecules or other molecular entities, more preferably at least 97% of the molecules or other molecular entities, and most preferably at least 99% of the molecules or other molecular entities are miscible with or soluble in water at 25° C.

A "hydrophilic surface" refers to a surface on which a water droplet has a contact angle of less than 90 degrees. In some embodiments, the surface is preferably immersed in toluene.

A "hydrophobic surface" refers to a surface on which a water droplet has a contact angle of at least 90 degrees. In some embodiments, the surface is preferably immersed in toluene.

A substrate or a surface that is "stable" or has "stability" refers to a substrate or surface having the ability to retain a roll off angle of at least 80 percent (%), preferably at least 85%, more preferably at least 90%, or even preferably at least 95% of an initial roll off angle after being submersed in a hydrocarbon fluid at a temperature of at least 50° C. for at least 1 hour, at least 12 hours, or at least 24 hours, and up to 10 days, up to 30 days, or up to 90 days. In some embodiments, the "initial roll off angle" of the surface or the substrate is the roll off angle of a surface substrate that has been submersed in a hydrocarbon fluid for less than an hour, or more preferably less than 20 minutes.

A "polar functional group" refers to a functional group having a net dipole as a result of the presence of electronegative atoms (for example, nitrogen, oxygen, chlorine, fluorine, etc.).

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

The term "consisting of" means including, and limited to, whatever follows the phrase "consisting of" That is, "consisting of" indicates that the listed elements are required or mandatory, and that no other elements may be present.

The term "consisting essentially of" indicates that any elements listed after the phrase are included, and that other elements than those listed may be included provided that those elements do not interfere with or contribute to the activity or action specified in the disclosure for the listed elements.

Unless otherwise specified, "a," "an," "the," and "at least one" are used interchangeably and mean one or more than one.

Also herein, the recitations of numerical ranges by endpoints include all numbers subsumed within that range (for example, 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE DRAWINGS

FIG. 1A shows an exemplary arrangement of the layers of a filter media including a substrate. FIG. 1B shows an exemplary arrangement of the layers of a filter media including a substrate. FIG. 1C shows an exemplary arrangement of the layers of a filter media including a substrate. FIG. 1D shows an exemplary arrangement of the layers of a filter media including a substrate.

DETAILED DESCRIPTION

Figure 2:
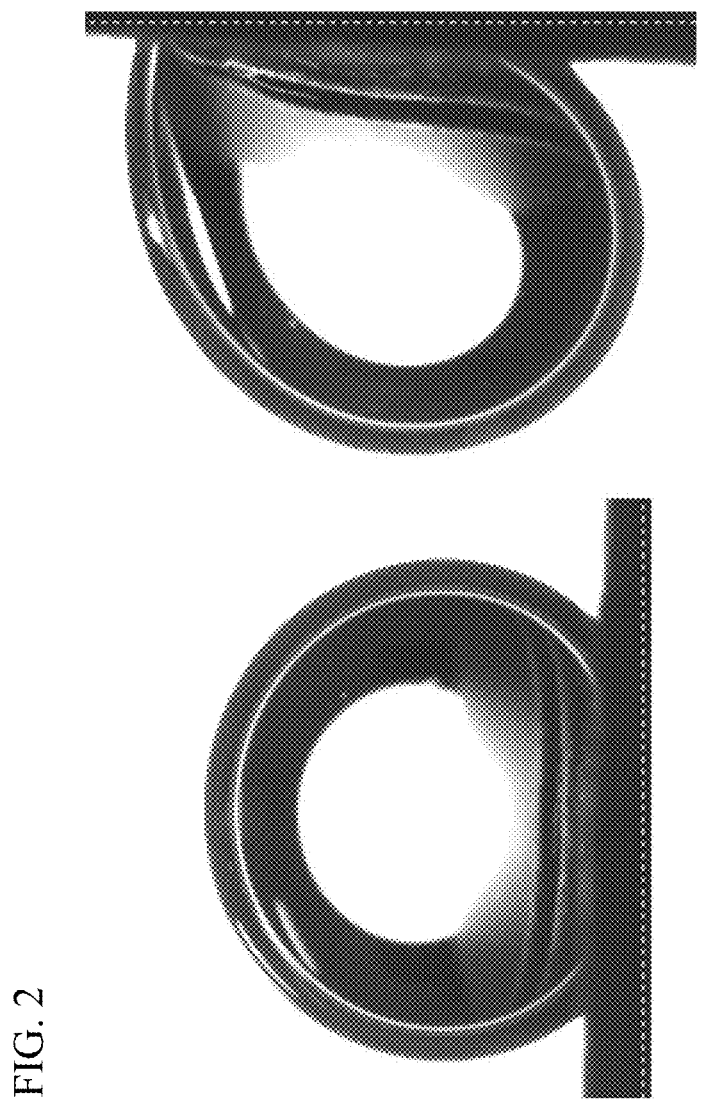
FIG. 2 exemplary images of a 50 µL water droplet on UV-oxygen-treated Substrate 1 immersed in toluene at 0 degrees (0°) rotation (left) and 90° rotation (right).

A hydrocarbon fluid-water separation filter can include a filter media that includes at least one layer to remove particles and/or at least one layer to coalesce water from a hydrocarbon fluid stream; the layer or layers can be a substrate or can be supported by a substrate. In some embodiments, the particle removal layer and the water-coalescing layer can be the same layer and the layer can be a substrate or can be supported by a substrate. This disclosure describes a filter media including a substrate for use in a hydrocarbon fluid-water separation filter, methods of identifying the substrate, methods of making the substrate, methods of using the substrate, and methods of improving the roll off angle of the substrate. Inclusion of the substrate in a filter media or a filter element including, for example, a hydrocarbon fluid-water separation filter element, can provide more efficient filter manufacturing and/or improved performance characteristics of the filter media or filter element including, for example, improved water separation efficiency.

The hydrocarbon fluid can include, for example, diesel fuel, gasoline, hydraulic fluid, compressor oils, etc. In some embodiments, the hydrocarbon fluid preferably includes diesel fuel.

Methods of Identifying Material Suitable for Hydrocarbon Fluid-Water Separation

In one aspect, this disclosure describes a method of identifying a material including, for example, a filter media, having specific properties. The material is preferably suitable for hydrocarbon fluid-water separation.

In some embodiments, the method includes determining the roll off angle and, optionally, the contact angle of a droplet on a surface of the material while the material is immersed in fluid that includes a hydrocarbon. In some embodiments, the method includes identifying a material having the properties of a substrate suitable for hydrocarbon fluid-water separation including the roll off angle and/or contact angles described below.

In some embodiments, the droplet includes a hydrophile. In some embodiments, the droplet preferably includes water. In some embodiments, the droplet consists essentially of water. In some embodiments, the droplet consists of water. In some embodiments, the droplet is at least 5 µL, at least 10 µL, at least 15 µL, at least 20 µL, at least 25 µL, at least 30 µL, at least 35 µL, at least 40 µL, at least 45 µL, or at least 50 µL. In some embodiments, the droplet is up to 10 µL, up to 15 µL, up to 20 µL, up to 25 µL, up to 30 µL, up to 35 µL, up to 40 µL, up to 45 µL, up to 50 µL, up to 60 µL, up to 70 µL, or up to 100 µL. In some embodiments, the droplet is preferably a 20 µL droplet or a 50 µL droplet.

In some embodiments, the fluid that includes a hydrocarbon includes toluene. In some embodiments, the fluid that includes a hydrocarbon consists essentially of toluene. In some embodiments, the fluid that includes a hydrocarbon consists of toluene. Without wishing to be bound by theory, it is believed that, because of its interfacial tension with water, toluene acts as a surrogate for other hydrocarbon fluids including, for example, diesel fuel.

In contrast to previous methods for identifying materials suitable for use in hydrocarbon fluid-water separation, the methods described herein do not rely on the properties of a flat surface (for example, a surface that is non-porous). Rather, the methods described herein provide methods for testing the properties of a porous material (including, for example, a porous substrate) or a material having a porous surface. Furthermore, the methods described herein do not rely on the properties of the material in air. Rather, the materials are identified by the properties of the material in a fluid that includes a hydrocarbon including, for example, toluene.

For example, WO 2015/175877 says that a filter media designed to enhance fluid separation efficiency may comprise one or more layers having a surface modified to wet the fluid to be separated and one or more layers having a surface modified to repel the fluid to be separated. And WO 2015/175877 states that a "hydrophilic surface" may refer to a surface that has a water contact angle of less than 90 degrees and a "hydrophobic surface" may refer to a surface that has a water contact angle of greater than 90 degrees. But WO 2015/175877 does not say that the contact angle should be calculated in fluid rather than in air. And, indeed, the hydrophobicity of a surface in air does not predict the hydrophobicity of a surface in a hydrocarbon fluid.

Moreover, WO 2015/175877 does not say that the roll off angle of a surface is important and does not say how to select materials that alter the roll off angle. Rather, WO 2015/175877 says that roughness or coatings may be used to modify the wettability of a layer with respect to a particular fluid and that the terms "wet" and "wetting" refer to the ability of a fluid to interact with a surface such that the contact angle of the fluid with respect to the surface is less than 90 degrees.

But the wettability or contact angle of a surface alone—whether measured in air or in a hydrocarbon fluid—does not predict the hydrocarbon-water separation ability of the surface in a hydrocarbon fluid. In contrast, and as further described below, the adhesion or roll off angle of a water droplet on a surface in a hydrocarbon fluid optionally in combination with the contact angle of a droplet on the surface in a hydrocarbon fluid can be used to predict the ability of a substrate to remove water from hydrocarbon fluid.

Properties of the Substrate Surface

In one aspect, this disclosure describes a filter media that includes a substrate suitable for hydrocarbon fluid-water separation. The substrate includes a surface. In some embodiments, the substrate or a surface of the substrate are preferably stable.

In some embodiments, the surface has a roll off angle of at least 30 degrees, at least 35 degrees, at least 40 degrees, at least 45 degrees, at least 50 degrees, at least 55 degrees, at least 60 degrees, at least 65 degrees, at least 70 degrees, at least 75 degrees, or at least 80 degrees for a 20 µL water droplet when the surface is immersed in toluene. In some embodiments, the surface has a roll off angle of at least 30 degrees, at least 35 degrees, at least 40 degrees, at least 45 degrees, at least 50 degrees, at least 55 degrees, at least 60 degrees, at least 65 degrees, at least 70 degrees, at least 75 degrees, or at least 80 degrees for a 50 µL water droplet when the surface is immersed in toluene.

In some embodiments, the surface has a roll off angle of up to 60 degrees, up to 65 degrees, up to 70 degrees, up to 75 degrees, up to 80 degrees, up to 85 degrees, or up to 90 degrees for a 20 µL water droplet when the surface is immersed in toluene. In some embodiments, the surface has a roll off angle of up to 60 degrees, up to 65 degrees, up to 70 degrees, up to 75 degrees, up to 80 degrees, up to 85 degrees, or up to 90 degrees for a 50 µL water droplet when the surface is immersed in toluene.

In some embodiments, the surface has a roll off angle in a range of 50 degrees to 90 degrees for a 20 µL water droplet when the surface is immersed in toluene. In some embodiments, the surface has a roll off angle in a range of 40 degrees to 90 degrees for a 50 µL water droplet when the surface is immersed in toluene.

In some embodiments, the surface is preferably hydrophobic, that is, the surface has a contact angle of at least 90 degrees. In some embodiments, the surface has a contact angle of at least 90 degrees, at least 100 degrees, at least 110 degrees, at least 120 degrees, at least 130 degrees, or at least 140 degrees for a 20 µL water droplet when the surface is immersed in toluene. In some embodiments, the surface has a contact angle of at least 90 degrees, at least 100 degrees, at least 110 degrees, at least 120 degrees, at least 130 degrees, or at least 140 degrees for a 50 µL water droplet when the surface is immersed in toluene.

In some embodiments, the surface has contact angle of up to 150 degrees, up to 160 degrees, up to 170 degrees, or up to 180 degrees for a 20 µL water droplet when the surface is immersed in toluene. In some embodiments, the surface has contact angle of up to 150 degrees, up to 160 degrees, up to 170 degrees, or up to 180 degrees for a 50 µL water droplet when the surface is immersed in toluene.

In some embodiments, the surface has a contact angle in a range of 90 degrees to 150 degrees or in a range of 90 degrees to 180 degrees for a 20 µL water droplet when the surface is immersed in toluene.

In some embodiments, the surface has a contact angle in a range of 90 degrees to 150 degrees or in a range of 90 degrees to 180 degrees for a 50 µL water droplet when the surface is immersed in toluene.

As further described below, the roll off angle (that is, the adhesion) of a water droplet on a hydrophobic surface (that is, a surface having a contact angle of at least 90 degrees) of a substrate in a hydrocarbon fluid correlates with the size of a water droplet that can be coalesced or grown on the surface of the substrate in a hydrocarbon fluid. The size of the water droplet that can be coalesced or grown correlates with the ability of a substrate to remove water from hydrocarbon fluid. Thus, the ability of a substrate to remove water from hydrocarbon fluid can be accurately predicted by determining the roll off angle and the contact angle of a water droplet on the surface of the substrate in a hydrocarbon fluid.

Substrates produced and/or identified by the methods disclosed herein have a high contact angle and high roll off angle. The high contact angle is indicative of the low apparent drag forces on a water droplet, while the high roll off angle is indicative of the ability of the droplet to be retained on the substrate surface. Without wishing to be bound by theory, it is believed that this combination of features allows larger droplets to form through coalescence, making the droplets easier to separate from a hydrocarbon fluid stream, and improving the overall efficiency of water separation from the hydrocarbon fluid stream.

The balance of high contact angle and high roll off angle is achievable using the methodology disclosed herein including, for example, by modifying substrate surfaces to increase their roll off angle. Typically, these methods have little negative impact on the contact angle. In some embodiments, filter substrates having high contact angles can, therefore, be modified to provide a substrate having the claimed combination of contact angle and roll off angle.

Substrate Materials and Properties

The substrate can be any substrate suitable for use in a filter media. In some embodiments, the substrate is preferably a substrate suitable for use in a hydrocarbon fluid filter element including, for example, a fuel filter. In some embodiments, the substrate can include, for example, cellulose, polyester, polyamide, polyolefin, glass, or combinations thereof (for example, blends, mixtures, or copolymers thereof). The substrate can include, for example, a nonwoven web, a woven web, a porous sheet, a sintered plastic, a high density screen, a high density mesh, or combinations thereof. In some embodiments, the substrate can include synthetic fibers, naturally occurring fibers, or combinations thereof (for example, blends or mixtures thereof). The substrate is typically of a porous nature and of a specified and definable performance characteristic such as pore size, Frazier air permeability, and/or another suitable metric.

In some embodiments, the substrate can include a thermoplastic or a thermosetting polymer fiber. The polymers of the fiber may be present in a single polymeric material system, in a bicomponent fiber, or in a combination thereof. A bicomponent fiber may include, for example, a thermoplastic polymer. In some embodiments, a bicomponent fiber can have a core-sheath structure, including a concentric or a non-concentric structure. In some embodiments, the sheath of the bicomponent fiber can have a melting temperature lower than the melting temperature of the core such that, when heated, the sheath binds to the other fibers in the layer while the core maintains structural integrity. Exemplary embodiments of bicomponent fibers include side-by-side fibers or island-in-the-sea fibers.

In some embodiments, the substrate can include a cellulosic fiber including, for example, a softwood fiber (such as mercerized southern pine), a hardwood fiber (such as *Eucalyptus* fibers), a regenerated cellulose fiber, a mechanical pulp fiber, or a combination thereof (for example, a mixture or blend thereof).

In some embodiments, the substrate can include a glass fiber including, for example, a microglass, a chopped glass fiber, or a combination thereof (for example, a mixture or blend thereof).

In some embodiments, the substrate includes a fiber having a mean diameter of at least 0.3 micron, at least 1 micron, at least 10 microns, at least 15 microns, at least 20 microns, or at least 25 microns. In some embodiments, the substrate includes a fiber having a mean diameter of up to 50 microns, up to 60 microns, up to 70 microns, up to 75 microns, up to 80 microns, or up to 100 microns. A person having skill in the art will recognize that the diameter of the fiber may be varied depending on the fiber material as well as the process used to manufacture the fiber. The length of these fibers can also vary from a few millimeters in length to being a continuous fibrous structure. The cross-sectional shape of the fiber can also be varied depending on the material or manufacturing process used.

The substrate may, in some embodiments, include one or more binding materials. In some embodiments, a binding material includes a modifying resin that provides additional rigidity and/or hardness to the substrate. For example, in some embodiments, the substrate may be saturated with a modifying resin. A modifying resin may include a UV-reactive resin, as described herein, or a non-UV-reactive resin. A modifying resin may, in some embodiments, include a phenolic resin and/or an acrylic resin. A non-UV-reactive resin may, in some embodiments, include an acrylic resin that lacks an aromatic component and/or an unsaturated component.

In some embodiments, including, for example, when the substrate is prepared by being subjected to UV treatment, the substrate preferably includes an aromatic component and/or an unsaturated component. The aromatic component and/or an unsaturated component may be present in the materials included in the substrate or may be added to the substrate using another material including, for example, a resin. A resin including an aromatic component and/or an unsaturated component is referred to herein as a UV-reactive resin. A UV-reactive resin may include, for example, a phenolic resin. In some embodiments, the unsaturated component preferably includes a double bond.

In some embodiments, the substrate includes pores having an average diameter of up to 10 micrometers (μm), up to 20 μm, up to 30 μm, up to 40 μm, up to 45 μm, up to 50 μm, up to 60 μm, up to 70 μm, up to 80 μm, up to 90 μm, up to 100 μm, up to 200 μm, up to 300 μm, up to 400 μm, up to 500 μm, up to 600 μm, up to 700 μm, up to 800 μm, up to 900 μm, up to 1 millimeter (mm), up to 1.5 mm, up to 2 mm, up to 2.5 mm, or up to 3 mm. In some embodiments, the substrate includes pores having an average diameter of at least 2 μm, at least 5 μm, at least 10 μm, at least 20 μm, at least 30 μm, at least 40 μm, at least 50 μm, at least 60 μm, at least 70 μm, at least 80 μm, at least 90 μm, at least 100 μm, at least 200 μm, at least 300 μm, at least 400 μm, at least 500 μm, at least 600 μm, at least 700 μm, at least 800 μm, at least 900 μm, or at least 1 mm. In some embodiments, the substrate includes pores having an average diameter in a range of 5 μm to 100 μm. In some embodiments, the substrate includes pores having an average diameter in a range of 40 μm to 50 μm. In some embodiments, pore size may be measured using capillary flow porometry. In some embodiments, pore size is preferably measured by liquid extrusion porometry, as described in US Patent Publication No. 2011/0198280.

In some embodiments, the substrate is at least 15% porous, at least 20% porous, at least 25% porous, at least 30% porous, at least 35% porous, at least 40% porous, at least 45% porous, at least 50% porous, at least 55% porous, at least 55% porous, at least 60% porous, at least 65% porous, at least 70% porous, at least 75% porous, or at least 80% porous. In some embodiments, the substrate is up to 75% porous, up to 80% porous, up to 85% porous, up to 90% porous, up to 95% porous, up to 96% porous, up to 97% porous, up to 98% porous, or up to 99% porous. For example, the substrate may be at least 15% porous and up to 99% porous, at least 50% porous and up to 99% porous, or at least 80% porous and up to 95% porous.

In some embodiments, the filter media may be designed for flow that passes from upstream to downstream during use of the filter media. In some embodiments, including for example, when a filter media includes a substrate located downstream of an upstream layer, the substrate may include pores having an average diameter greater than the average diameter of the pores of the upstream layer. Additionally or alternatively, the substrate may include pores having an average diameter greater than the average diameter of a droplet that forms on a downstream side of the upstream layer. For example, when a filter media includes an upstream layer that is a coalescing layer that includes pores having an average diameter, the substrate may include pores having an average diameter greater than the average diameter of the pores of the coalescing layer.

Typically, a surface of a material (including, for example, a substrate), prior to any surface modification or treatment, has a roll off angle of less than 50 degrees, less than 40 degrees, or less than 30 degrees for a 20 μL water droplet when the surface is immersed in toluene. Typically, a surface of a material (including, for example, a substrate), prior to any surface modification or treatment, has a roll off angle of less than 30 degrees, less than 20 degrees, less than 15 degrees, or less than 12 degrees for a 50 μL water droplet when the surface is immersed in toluene.

For example, the roll off angle of the surface prior to any surface modification or treatment may be in a range of 0 degrees to 50 degrees for a 20 μL water droplet when the surface is immersed in toluene.

In some embodiments, the roll off angle of the surface prior to any surface modification or treatment may preferably be in a range of 0 degrees to 40 degrees for a 20 μL water droplet when the surface is immersed in toluene.

For example, the roll off angle of the surface prior to any surface modification or treatment may be in a range of 0 degrees to 20 degrees for a 50 μL water droplet when the surface is immersed in toluene.

Providing a material (including, for example, a substrate) having a surface having a suitable roll off angle is within the remit of the skilled person.

Typically, a surface of a material (including, for example, a substrate), prior to any surface modification or treatment, has a contact angle of at least 90 degrees, at least 100 degrees, or at least 110 degrees for a 20 μL water droplet when the surface is immersed in toluene. Typically, a surface of a material (including, for example, a substrate), prior to any surface modification or treatment, has a contact angle of at least 90 degrees, at least 100 degrees, or at least 110 degrees for a 50 μL water droplet when the surface is immersed in toluene.

For example, the contact angle of the surface, prior to any surface modification or treatment, may be in a range of 90 degrees to 180 degrees for a 20 μL water droplet when the surface is immersed in toluene.

In some embodiments, the contact angle of the surface, prior to any surface modification or treatment, may preferably be in a range of 100 degrees to 150 degrees for a 20 μL water droplet when the surface is immersed in toluene.

For example, the contact angle of the surface, prior to any surface modification or treatment, may be in a range of 90 degrees to 180 degrees for a 50 μL water droplet when the surface is immersed in toluene.

In some embodiments, the contact angle of the surface, prior to any surface modification or treatment, may preferably be in a range of 100 degrees to 150 degrees for a 50 μL water droplet when the surface is immersed in toluene.

In some embodiments, the surface, prior to any surface modification or treatment, may have a contact angle of 0 degrees, that is, a droplet will completely spread out on the surface. In some embodiments, including when the surface, prior to any surface modification or treatment, has a contact angle of 0 degrees, the roll of angle, prior to any surface modification or treatment, will be undefined.

Providing a material (including, for example, a substrate) having a surface having a suitable contact angle is within the remit of the skilled person. Typically, including materials that are generally hydrophobic will usually result in a higher contact angle.

Other factors that influence the contact angle of a surface may include the pore size and porosity. For instance, pores of a certain size may promote hydrocarbon fluid, which is hydrophobic, being trapped in the filter. Moreover, the high interfacial tension of water prevents it from effectively penetrating pores below a certain size.

Filter Media Including the Substrate

In some embodiments, a filter media including the substrate is preferably used for hydrocarbon-water separation or, more preferably, fuel-water separation, and, most preferably, diesel fuel-water separation.

The filter media may include one layer, two layers, or a plurality of layers. In some embodiments, one or more of the layers of the filter media may be supported by the substrate, may include the substrate, or may be the substrate.

In some embodiments, and, as shown, for example, in FIG. 1A-D, the filter media may include a layer to remove particles from a hydrocarbon liquid stream 20 and/or a layer to coalesce water from a hydrocarbon liquid stream (also referred to as a coalescing layer) 30. In some embodiments, a layer to remove particles from a hydrocarbon liquid stream and/or a coalescing layer may be supported by the substrate 10, as shown in an illustrative embodiment in FIG. 1A and FIG. 1B. In some embodiments, including, for example, when the filter media is designed to accommodate a flow that passes from upstream to downstream during use of the filter media, a layer to remove particles from a hydrocarbon liquid stream and/or a coalescing layer can be located upstream of the substrate. In some embodiments, the layer to remove particles from a hydrocarbon liquid stream and the substrate are the same layer 40, as shown in one embodiment in FIG. 1C. In some embodiments, the coalescing layer and the substrate are the same layer 50, as shown in one embodiment in FIG. 1D. When the substrate and the layer to remove particles from a hydrocarbon liquid stream are the same layer or when the substrate and the layer to coalesce water from a hydrocarbon liquid stream are the same layer, filter media manufacturing may be more efficient because the filter media may include a decreased number of total layers.

In some embodiments, a surface of the substrate preferably forms a downstream side of the substrate. In some embodiments, a surface of the substrate can form a downstream side or layer of the filter media or a downstream side of the filter media.

In some embodiments, including, for example, when a surface of the substrate forms a downstream side or layer of the filter media or a downstream side of the filter media, the substrate may preferably be separated from another layer by sufficient space to allow water droplet formation and/or water droplet roll off. In some embodiments, the substrate may be separated from another layer by at least 10 µm, at least 20 µm, at least 30 µm, at least 40 µm, at least 50 µm, at least 100 µm, at least 200 µm, at least 500 µm, or at least 1 mm. In some embodiments, the substrate may be separated from another layer by up to 40 µm, up to 50 µm, up to 100 µm, up to 200 µm, up to 500 µm, up to 1 mm, up to 2 mm, up to 3 mm, up to 4 mm, or up to 5 mm.

In some embodiments, a layer configured to remove particulate contaminants 20 is located upstream of a coalescing layer 30 and the coalescing layer is located upstream of the substrate 10, as shown in one embodiment, in FIG. 1A. In some embodiments, a coalescing layer is located downstream of the substrate. In some embodiments, the filter media may include at least two coalescing layers with one of the coalescing layers located downstream of the substrate.

In some embodiments, the substrate may be included in a flow-by structure including, for example, a structure as described in U.S. Patent Application No. 62/543,456, filed Aug. 10, 2017 and entitled: Fluid Filtration Apparatuses, Systems, and Methods, which is hereby incorporated by reference for its description of media structures.

In some embodiments, the filter media can be included in a filter element. The filter media can have any suitable configuration. In some embodiments, the filter element can include a screen. In some embodiments, the screen can be located downstream of the substrate.

The filter media may have any suitable configuration. For example, the filter media can have a tubular configuration. In some embodiments, the filter media can include pleats.

Methods of Making

This disclosure further describes methods of making a material. In some embodiments, the material can include a filter media including a substrate. The material, filter media, substrate, and/or a surface thereof may be treated by any suitable method to achieve the desired roll off angle and the desired contact angle. In some embodiments, treating of the material, filter media, substrate, and/or a surface thereof includes treating only a portion of the material, filter media, substrate, and/or a surface thereof.

In some embodiments, the treatment to achieve the desired roll off angle and the desired contact angle does not change the structure of the substrate. For example, in some embodiments, the treatment does not change at least one of the average diameter of the pores of the substrate and permeability of the substrate. In some embodiments, the treatment does not change the appearance of the media when viewed at 500× magnification.

Curing

In some embodiments, the substrate includes a resin (for example, a modifying resin). Resins are well known and are typically used to improve the internal bonding of filter substrates.

Any suitable resin may be used including, for example, a UV-reactive resin or a non-UV-reactive resin. The resin may include, for example, a partially-cured resin (for example, a partially-cured phenolic resin), and curing of the resin may be performed to increase the rigidity of the substrate and/or to prevent disintegration of the substrate during use. Curing may be performed prior to performing a treatment to achieve the desired roll off angle and the desired contact angle or after performing a treatment to achieve the desired roll off angle and the desired contact angle. For example, if the substrate includes a hydrophilic group-containing polymer present in a separate layer from the resin, curing of the resin may be performed prior to formation of the layer including the hydrophilic group-containing polymer or after formation of the layer including the hydrophilic group-containing polymer. In some embodiments, the resin is preferably impregnated into the substrate.

The resin can include polymerizable monomers, polymerizable oligomers, polymerizable polymers, or combinations thereof (for example, blends, mixtures, or copolymers thereof). As used herein, curing refers to hardening of the resin and can include crosslinking and/or polymerizing components of the resin. In some embodiments, the resin includes polymers, and, during curing, the molecular weight of the polymer is increased due to crosslinking of the polymers.

Curing may be performed by any suitable means including, for example, by heating the substrate. In some embodiments, curing is preferably performed by heating the substrate at a temperature and for a time sufficient to cure a resin (including, for example, a phenolic resin). In some embodiments, the substrate may be heated at a temperature of at least 50° C., at least 75° C., at least 100° C., or at least 125° C. In some embodiments, the substrate may be heated at a temperature of up to 125° C., up to 150° C., up to 175° C., or up to 200° C. In some embodiments, the substrate may be heated to a temperature having a range of 50° C. to 200° C. In some embodiments, the substrate may be heated for at least 1 minute, at least 2 minutes, at least 5 minutes, at least 7 minutes, at least 10 minutes, or at least 15 minutes. In some embodiments, the substrate may be heated for up to 8 minutes, up to 10 minutes, up to 12 minutes, up to 15 minutes, up to 20 minutes, or up to 25 minutes. In some embodiments, it may be preferred to heat the substrate at 150° C. for 10 minutes.

Methods of Treating a Substrate to Improve the Roll off Angle

In some embodiments, the disclosure relates to methods of treating a substrate to improve the roll off angle of a surface. Without wishing to be bound by theory, the various methods disclosed are believed to improve the roll off angle by modifying the surface properties of the substrate to make the microstructure of the surface more hydrophilic, while retaining the overall hydrophobic properties of the surface to water droplets.

The various different approaches include those set out below.

UV

In some embodiments, the substrate includes a UV-treated surface, that is, a surface treated with UV radiation. In such embodiments, the substrate preferably includes an aromatic and/or unsaturated component.

For instance, the substrate may include a fibrous material having an aromatic and/or unsaturated component. In some embodiments, the substrate may include a UV-reactive resin, that is, a resin having an aromatic and/or unsaturated component. Such a UV-reactive resin may be present in addition to a fibrous material having an aromatic and/or unsaturated component, or may be used in combination with fibrous material not having an aromatic and/or unsaturated component. In some embodiments, the substrate preferably includes an aromatic resin (that is, a resin containing aromatic groups) including, for example, a phenolic resin.

In some embodiments, the UV radiation is applied to the substrate at a distance from the source of at least 0.25 centimeters (cm), at least 0.5 cm, at least 0.75 cm, at least 1 cm, at least 1.25 cm, at least 2 cm, or at least 5 cm. In some embodiments, the UV radiation is applied to the substrate at a distance from the source of up to 0.5 cm, up to 1 cm, up to 2 cm, up to 3 cm, up to 5 cm, or up to 10 cm.

In some embodiments, the substrate is exposed to UV radiation of at least 250 microwatts per square centimeter ($\mu W/cm^2$), at least 300 $\mu W/cm^2$, at least 500 $\mu W/cm^2$, at least 1 milliwatt per square centimeter ($mW/cm^2$), at least 5 $mW/cm^2$, at least 10 $mW/cm^2$, at least 15 $mW/cm^2$, at least 20 $mW/cm^2$, at least 21 $mW/cm^2$, or at least 25 $mW/cm^2$. In some embodiments, the substrate is exposed to UV radiation of up to 20 $mW/cm^2$, up to 21 $mW/cm^2$, up to 22 $mW/cm^2$, up to 25 $mW/cm^2$, up to 30 $mW/cm^2$, up to 40 $mW/cm^2$, up to 50 $mW/cm^2$, up to 60 $mW/cm^2$, up to 70 $mW/cm^2$, up to 80 $mW/cm^2$, up to 90 $mW/cm^2$, up to 100 $mW/cm^2$, up to 150 $mW/cm^2$, or up to 200 $mW/cm^2$.

In some embodiments, for example, the substrate is exposed to UV radiation in a range of 300 $\mu W/cm^2$ to 100 $mW/cm^2$.

In some embodiments, for example, the substrate is exposed to UV radiation in a range of 300 $\mu W/cm^2$ to 200 $mW/cm^2$.

In some embodiments, the substrate is exposed to (that is, treated with) UV radiation for at least 1 second, at least 2 seconds, at least 3 seconds, at least 5 seconds, at least 10 seconds, at least 30 seconds, at least 1 minute, at least 2 minutes, at least 3 minutes, at least 4 minutes, at least 5 minutes, at least 7 minutes, at least 9 minutes, at least 10 minutes, at least 11 minutes, at least 13 minutes, at least 15 minutes, at least 17 minutes, or at least 20 minutes. In some embodiments, the substrate is exposed to UV radiation for up to 5 seconds, up to 10 seconds, up to 30 seconds, up to 1 minute, up to 2 minutes, up to 4 minutes, up to 5 minutes, up to 6 minutes, up to 8 minutes, up to 10 minutes, up to 12 minutes, up to 14 minutes, up to 15 minutes, up to 16 minutes, up to 18 minutes, up to 20 minutes, up to 22 minutes, up to 24 minutes, up to 25 minutes, up to 26 minutes, up to 28 minutes, or up to 30 minutes.

In some embodiments, the UV radiation is applied for a time in a range of 2 seconds to 20 minutes.

In some embodiments, different wavelengths of UV radiation may be applied sequentially. In some embodiments, it may be preferable to apply different wavelengths of UV radiation simultaneously.

Without wishing to be bound by theory, it is believed that the UV radiation causes an aromatic and/or unsaturated component to react and become chemically modified. This reaction increases the roll off angle of the surface while substantially retaining the contact angle properties.

It has been found that additional agents, such as those set out below, may promote the chemical reaction of aromatic and/or unsaturated components present in and/or on the substrate. These additional agents may be used individually, sequentially, and/or simultaneously during treatment of the substrate with UV.

UV+Oxygen

In some embodiments, the substrate preferably includes a UV-oxygen-treated surface, that is, a surface treated with UV radiation in the presence of oxygen. Treatment in the presence of oxygen can include at least one of, for example, treatment in atmospheric air including oxygen, treatment in an oxygen-containing environment, treatment in an oxygen-enriched environment, or treatment of a substrate that includes oxygen in or on the substrate.

In some embodiments, the substrate is preferably treated under conditions and with wavelengths of UV radiation sufficient to generate ozone and oxygen radicals. In some embodiments, the UV radiation source is preferably a low pressure mercury lamp. The UV radiation may be applied using any combination of the parameters described above with respect to treatment with UV radiation including distance, intensity, and time, and multiple wavelengths may be applied using sequential or simultaneous application.

In some embodiments, the UV radiation includes a wavelength capable of forming two oxygen radicals (O.) from $O_2$. Oxygen radicals can react with $O_2$ to form ozone ($O_3$). In some embodiments, the UV radiation includes a wavelength of at least 165 nanometers (nm), at least 170 nm, at least 175 nm, at least 180 nm, or at least 185 nm. In some embodiments, the UV radiation includes a wavelength of up to 190 nm, up to 195 nm, up to 200 nm, up to 205 nm, up to 210 nm, up to 215 nm, up to 220 nm, up to 230 nm, or up to 240 nm. In some embodiments, the UV radiation includes a wavelength in a range of 180 nm to 210 nm. In some embodiments, the UV radiation includes a wavelength of 185 nm.

In some embodiments, the UV radiation includes a wavelength capable of splitting ozone ($O_3$) to form $O_2$ and an oxygen radical (O.). In some embodiments, the UV radiation includes a wavelength of at least 200 nm, at least 205 nm, at least 210 nm, at least 215 nm, at least 220 nm, at least 225 nm, at least 230 nm, at least 235 nm, at least 240 nm, at least 245 nm, or at least 250 nm. In some embodiments, the UV radiation includes a wavelength of up to 260 nm, up to 265 nm, up to 270 nm, up to 275 nm, up to 280 nm, up to 285 nm, up to 290 nm, up to 295 nm, up to 300 nm, up to 310 nm, or up to 320 nm. In some embodiments, the UV radiation includes a wavelength in a range of 210 nm to 280 nm. In some embodiments, the UV radiation includes a wavelength of 254 nm.

UV+Ozone

In some embodiments, the substrate includes a UV-ozone-treated surface, that is, a surface treated with UV radiation in the presence of ozone ($O_3$). The UV radiation may be applied using any combination of the parameters described above with respect to treatment with UV radiation including distance, intensity, and time, and multiple wavelengths may be applied using sequential or simultaneous application.

Treatment in the presence of ozone can include, for example, treatment in an ozone-containing environment or treatment during the generation of ozone within the environment (for example, by corona discharge). In some embodiments, the ozone-containing environment includes $O_2$. In other embodiments the ozone-containing environment includes less than 10 percent by volume (vol.-%) $O_2$, less than 5 vol.-% $O_2$, less than 2 vol.-% $O_2$, or less than 1 vol.-% $O_2$. In some embodiments, the ozone-containing environment includes an inert gas, such as nitrogen, helium, argon, or mixtures thereof.

In some embodiments the ozone-containing environment includes at least 0.005 vol.-% $O_3$, at least 0.01 vol.-% $O_3$, at least 0.05 vol.-% $O_3$, at least 0.1 vol.-% $O_3$, at least 0.5 vol.-% $O_3$, at least 1 vol.-% $O_3$, at least 2 vol.-% $O_3$, at least 5 vol.-% $O_3$, at least 10 vol.-% $O_3$, or at least 15 vol.-% $O_3$. In some embodiments, the ozone-containing environment includes a higher concentration of ozone at the surface of the substrate. Such a concentration can be achieved by, for example, introducing the ozone at the substrate surface (for example, by allowing ozone to diffuse from the back side of the media.) In some embodiments, the concentration of ozone at or near the surface of the substrate is preferably sufficient to generate oxygen radicals from the ozone present in the presence of UV radiation.

In some embodiments, the UV radiation includes a wavelength capable of splitting ozone ($O_3$) to form $O_2$ and an oxygen radical (O.). In embodiments, including, for example, when the ozone-containing environment includes less than 10 vol.-% $O_2$, less than 5 vol.-% $O_2$, less than 2 vol.-% $O_2$, or less than 1 vol.-% $O_2$, the UV radiation can include a wavelength of at least 165 nm, at least 170 nm, at least 175 nm, at least 180 nm, or at least 185 nm and of up to 260 nm, up to 265 nm, up to 270 nm, up to 275 nm, up to 280 nm, up to 285 nm, or up to 290 nm. In some embodiments, the UV radiation includes a wavelength in a range of 180 nm to 280 nm.

In embodiments when the ozone-containing environment includes $O_2$ that would absorb UV radiation in a range of 180 nm to 210 nm, the UV radiation preferably includes a wavelength of at least 210 nm, at least 215 nm, at least 220 nm, at least 225 nm, at least 230 nm, at least 235 nm, at least 240 nm, at least 245 nm, or at least 250 nm. In some embodiments, the UV radiation includes a wavelength of up to 260 nm, up to 265 nm, up to 270 nm, up to 275 nm, up to 280 nm, up to 285 nm, up to 290 nm, up to 295 nm, up to 300 nm, up to 310 nm, or up to 320 nm. In some embodiments, the UV radiation includes a wavelength in a range of 210 nm to 280 nm. In some embodiments, the UV radiation includes a wavelength of 254 nm.

UV+$H_2O_2$

In some embodiments, the substrate includes a UV-$H_2O_2$-treated surface, that is, a surface treated with UV radiation and $H_2O_2$. In some embodiments, the surface of the substrate and/or the entire substrate may be placed in contact with (for example, coated with and/or submerged in) a solution including $H_2O_2$. In some embodiments, the solution can include at least 20 percent by weight (wt.-%) $H_2O_2$, at least 25 wt.-% $H_2O_2$, at least 30 wt.-% $H_2O_2$, at least 40 wt.-% $H_2O_2$, at least 50 wt.-% $H_2O_2$, at least 60 wt.-% $H_2O_2$, at least 70 wt.-% $H_2O_2$, at least 80 wt.-% $H_2O_2$, or at least 90 wt.-% $H_2O_2$. In some embodiments, the solution can contain up to 30 wt.-% $H_2O_2$, up to 40 wt.-% $H_2O_2$, up to 50 wt.-% $H_2O_2$, up to 60 wt.-% $H_2O_2$, up to 70 wt.-% $H_2O_2$, up to 80 wt.-% $H_2O_2$, up to 90 wt.-% $H_2O_2$, or up to 100 wt.-% $H_2O_2$.

In some embodiments, the substrate may be placed in contact with a solution including $H_2O_2$ for at least 10 seconds, at least 30 seconds, at least 45 seconds, at least 1 minute, at least 2 minutes, at least 4 minutes, at least 6 minutes, or at least 8 minutes. In some embodiments, the substrate may be in contact with a solution including $H_2O_2$ for up to 30 seconds, up to 45 seconds, up to 1 minute, up to 2 minutes, up to 4 minutes, up to 6 minutes, up to 8 minutes, up to 10 minutes, or up to 30 minutes.

In some embodiments, the substrate may be treated with UV radiation while in contact with a solution including $H_2O_2$. In some embodiments, the substrate may be treated with UV radiation after being in contact with a solution including $H_2O_2$. The UV radiation may be applied using any combination of the parameters described above with respect to treatment with UV radiation including distance, intensity, and time, and multiple wavelengths may be applied using sequential or simultaneous application.

The substrate may be treated with UV radiation sufficient to generate hydroxyl radicals (.OH). The substrate may be treated with UV radiation while the surface is in contact with $H_2O_2$, after the surface has been in contact with $H_2O_2$, or both during contact and after contact with $H_2O_2$. In some embodiments, the UV radiation includes a wavelength capable of forming two oxygen radicals (O.) from $O_2$. Oxygen radicals can react with $O_2$ to form ozone ($O_3$). In some embodiments, the UV radiation includes a wavelength of at least 165 nm, at least 170 nm, at least 175 nm, at least 180 nm, or at least 185 nm. In some embodiments, the UV radiation includes a wavelength of up to 190 nm, up to 195 nm, up to 200 nm, up to 205 nm, up to 210 nm, up to 215 nm, up to 220 nm, up to 230 nm, or up to 240 nm. In some embodiments, the UV radiation includes a wavelength in a range of 180 nm to 210 nm. In some embodiments, the UV radiation includes a wavelength of 185 nm.

In some embodiments, the UV radiation includes a wavelength capable of splitting ozone ($O_3$) to form $O_2$ and an oxygen radical (O.). In some embodiments, the UV radiation includes a wavelength of at least 200 nm, at least 205 nm, at least 210 nm, at least 215 nm, at least 220 nm, at least 225 nm, at least 230 nm, at least 235 nm, at least 240 nm, at least 245 nm, or at least 250 nm. In some embodiments, the UV radiation includes a wavelength of up to 260 nm, up to 265 nm, up to 270 nm, up to 275 nm, up to 280 nm, up to 285 nm, up to 290 nm, up to 295 nm, up to 300 nm, up to 310 nm, or up to 320 nm. In some embodiments, the UV radiation includes a wavelength in a range of 210 nm to 280 nm. In some embodiments, the UV radiation includes a wavelength of 254 nm.

In some embodiments, the UV radiation includes a wavelength of at least 200 nm, at least 250 nm, at least 300 nm, at least 330 nm, at least 340 nm, at least 350 nm, at least 355 nm, at least 360 nm, or at least 370 nm. In some embodiments, the UV radiation includes a wavelength of up to 350 nm, up to 360 nm, up to 370 nm, up to 375 nm, up to 380 nm, up to 385 nm, up to 390 nm, up to 395 nm, up to 400 nm, up to 410 nm, or up to 420 nm. In some embodiments, the UV radiation includes a wavelength in a range of 350 nm to 370 nm. In some embodiments, the UV radiation includes a wavelength of 360 nm.

In some embodiments, a substrate may be dried after being placed in contact with a solution including $H_2O_2$ and before being treated with UV. In some embodiments, a substrate may be dried after being placed in contact with a solution including $H_2O_2$ and after being treated with UV. In some embodiments, the substrate may be oven dried.

The UV treatment (whether UV alone or UV with oxygen, ozone, and/or hydrogen peroxide) is more effective when the substrate includes an aromatic and/or unsaturated component, including, for example, when the substrate includes a UV-reactive resin including, for example, an aromatic resin (for example, a resin containing aromatic groups) including, for example, a phenolic resin.

Substrate Including a Hydrophilic Group-Containing Polymer

As an alternative or in addition to UV treatment, the surface properties of the substrate may be modified by the inclusion of a hydrophilic group-containing polymer in and/or on the substrate. In some embodiments when both UV treatment and inclusion of a hydrophilic group-containing polymer are used, it may be preferred to include a hydrophilic group-containing polymer in a substrate or to modify a substrate to include a hydrophilic group-containing polymer prior to UV treatment.

In some embodiments, the substrate includes a hydrophilic group-containing polymer. The hydrophilic group of the hydrophilic group-containing polymer can include a hydrophilic pendant group or a hydrophilic group that repeats within the polymer backbone or both. As used herein, a "pendant group" is covalently bound to the polymer backbone but does not form a part of the polymer backbone. In some embodiments, the hydrophilic group includes at least one of a hydroxy, an amide, an alcohol, an acrylic acid, a pyrrolidone, a methyl ether, an ethylene glycol, a propylene glycol, dopamine, and an ethylene imine. In some embodiments, a hydrophilic pendant group includes at least one of a hydroxy, an amide, an alcohol, an acrylic acid, a pyrrolidone, a methyl ether, and dopamine. In some embodiments, a hydrophilic group that repeats within the polymer backbone includes at least one of an ethylene glycol, a propylene glycol, dopamine, and an ethylene imine.

In some embodiments, a substrate including a hydrophilic group-containing polymer may include a surface having a hydrophilic group-containing polymer disposed thereon. In some embodiments, the substrate preferably includes a layer including a hydrophilic group-containing polymer. In some embodiments, the surface having the hydrophilic group-containing polymer disposed thereon or, in some embodiments, the hydrophilic group-containing polymer-containing layer, preferably forms the surface of the substrate having the desired properties (including roll off angle and contact angle), as described herein.

The layer may be formed using any suitable method. For example, the layer could be formed by applying a polymer including, for example, a pre-polymerized polymer. Additionally or alternatively, the layer could be formed by applying monomers, oligomers, polymers, or combinations thereof (for example, blends, mixtures, or copolymers thereof) and then polymerizing the monomers, oligomers, polymers, or combinations thereof to form a polymer, copolymer, or combination thereof. In some embodiments, a polymer may be deposited from a solution using oxidative or reductive polymerization.

In some embodiments, the layer may be formed using any suitable coating process including, for example, plasma-deposition coating, roll-to-roll coating, dip coating, and/or spray coating. Spray coating may include, for example, air pressure spraying, electrostatic spraying, etc. In some embodiments, the surface may be laminated. In some embodiments, the layer may be formed by spinning a polymer onto the substrate. Spinning a polymer onto the substrate may include, for example, electrospinning the polymer onto the substrate or depositing the polymer on the substrate by wet spinning, dry spinning, melt spinning, gel spinning, jet spinning, magnetospinning, etc. The spinning of the polymer onto the substrate may, in some embodiments, form polymer nanofibers. Additionally or alternatively, spinning of the polymer onto the substrate may coat fibers already present in the substrate. In some embodiments, including wherein the polymer is deposited by dry spinning polymer solution onto the substrate, one or more driving forces including air, an electric field, centrifugal force, a magnetic field, etc., may be used individually or in combination.

In some embodiments, the hydrophilic group-containing polymer includes polar functional groups.

In some embodiments, the hydrophilic group-containing polymer is a hydrophilic polymer.

In some embodiments, the hydrophilic group-containing polymer is not able to dissolve in water (for example, it is not a hydrophilic polymer) but rather includes at least one of a pendant group able to dissolve in water (for example, a hydrophilic pendant group) or a group that repeats within the polymer backbone that is able to dissolve in water (for example, a hydrophilic group that repeats within the polymer backbone).

In some embodiments, the hydrophilic group-containing polymer includes a hydroxylated methacrylate polymer. In some embodiments, the hydrophilic group-containing polymer does not include a fluorine group.

In some embodiments, the hydrophilic group-containing polymer does not include a fluoropolymer. As used herein, a fluoropolymer refers to a polymer that includes at least 5% fluorine, at least 10% fluorine, at least 15% fluorine, or at least 20% fluorine.

In some embodiments, the hydrophilic group-containing polymer can include, for example, poly(hydroxypropyl methacrylate) (PHPM) including poly(2-hydroxypropyl methacrylate, poly(3-hydroxypropyl methacrylate, or a mixture thereof; poly(2-hydroxyethyl methacrylate) (PHEM); poly(2-ethyl-2-oxazoline) (P2E2O); polyethyleneimine (PEI); quaternized polyethyleneimine; or poly(dopamine); or combinations thereof (for example, blends, mixtures, or copolymers thereof).

In some embodiments, the hydrophilic group-containing polymer can be dispersed and/or dissolved in a solvent during layer formation. In some embodiments, the solvent preferably solubilizes the hydrophilic group-containing polymer but does not solubilize the substrate or any component of the substrate. In some embodiments, the solvent is preferably non-toxic. In some embodiments, the hydrophilic group-containing polymer is preferably insoluble in a hydrocarbon fluid. In some embodiments, the hydrophilic group-containing polymer is preferably insoluble in toluene.

In some embodiments, the solvent is a solvent having a high dielectric constant. The solvent can include, for example, methanol, ethanol, propanol, isopropanol (also called isopropyl alcohol (IPA)), butanol (including each of its isomeric structures), butanone (including each of its isomeric structures), acetone, ethylene glycol, dimethyl formamide, ethyl acetate, water, etc.

The concentration of the hydrophilic group-containing polymer in the solvent can be selected based on the molecular weight of the polymer. In some embodiments, the hydrophilic group-containing polymer may be present in the solvent at a concentration of at least 0.25 percent (%) weight/volume (w/v), at least 0.5% (w/v), at least 0.75% (w/v), at least 1.0% (w/v), at least 1.25% (w/v), at least 1.5% (w/v), at least 1.75% (w/v), at least 2.0% (w/v), at least 3% (w/v), at least 5% (w/v), at least 10% (w/v), at least 20% (w/v), at least 30% (w/v), at least 40% (w/v), or at least 50% (w/v). In some embodiments, the hydrophilic group-containing polymer may be present in the solvent at a concentration of up to 0.5% (w/v), up to 0.75% (w/v), up to 1.0% (w/v), up to 1.25% (w/v), up to 1.5% (w/v), up to 1.75% (w/v), up to 2.0% (w/v), up to 3% (w/v), up to 4% (w/v), up to 5% (w/v), up to 10% (w/v), up to 15% (w/v), up to 20% (w/v), up to 30% (w/v), up to 40% (w/v), up to 50% (w/v), or up to 60% (w/v).

In some embodiments, including, for example, for depositing the hydrophilic group-containing polymer by dip coating, the polymer may be present in the solvent at a concentration in a range of 0.5% (w/v) to 4% (w/v).

In some embodiments, including, for example, for depositing the hydrophilic group-containing polymer by dip coating, the polymer may be present in the solvent at a concentration in a range of 0.5% (w/v) to 1% (w/v).

In some embodiments, including, for example, for depositing the hydrophilic group-containing polymer by electrospinning, the polymer may be present in the solvent at a concentration in a range of 5% (w/v) to 30% (w/v).

In some embodiments, the layer may be formed using dip coating. The dip coating can be accomplished by using, for example, a Chemat DipMaster 50 dip coater. In some embodiments, the layer may be formed by dip coating the substrate one, two, three, or more times. In some embodiments, the substrate may be dip coated, rotated 180 degrees, and dip coated again. In some embodiments, the substrate may be submerged in a dispersion including the hydrophilic group-containing polymer and withdrawn at a rate of 50 millimeters per minute (mm/min). In some embodiments, the dispersion is preferably a solution.

In some embodiments, the layer may be formed using electrospinning. The electrospinning may be accomplished as described, for example, in US20160047062 A1.

In some embodiments, including, for example, when the hydrophilic group-containing polymer includes poly(dopamine), the hydrophilic group-containing polymer may be deposited from a solution using oxidative or reductive polymerization. For example, a layer including poly(dopamine) may be prepared from the oxidative polymerization of dopamine.

In some embodiments, the layer including a hydrophilic group-containing polymer has a thickness of at least 0.5 Angstrom (Å), at least 1 Å, at least 5 Å, at least 8 Å, at least 10 Å, at least 12 Å, at least 14 Å, at least 16 Å, at least 18 Å, at least 20 Å, at least 25 Å, at least 30 Å, or at least 50 Å.

In some embodiments, solvent may be removed after layer formation including, for example, after a dip coating procedure. The solvent may be removed, for example, by evaporation including, for example, by drying using an oven.

In some embodiments, a charged coating may be formed (for example, via quaternization, electrochemical oxidation, or reduction) and/or the coating may include a charged polymer. In some embodiments, the layer including a hydrophilic group-containing polymer may be altered after formation of the layer. For example, the hydrophilic group-containing polymer may be quaternized. In some embodiments, the hydrophilic group-containing polymer can be quaternized by treating the polymer layer with an acid. In some embodiments, the hydrophilic group-containing polymer can be quaternized by dipping the substrate including the hydrophilic group-containing polymer layer in a solution including an acid. In some embodiments, the acid can be HCl.

In some embodiments, the hydrophilic group-containing polymer and/or the coating may be treated with maleic anhydride.

In some embodiments, the substrate may include a hydrophilic group-containing polymer disposed therein. If the substrate includes a modifying resin, the polymer is chemically distinct from the modifying resin. In some embodiments, the hydrophilic group-containing polymer may be applied simultaneously with a modifying resin. For example, the hydrophilic group-containing polymer may be mixed with a modifying resin before the modifying resin is applied to the substrate.

In some embodiments, the hydrophilic group-containing polymer may be crosslinked. In some embodiments, including, for example, when the polymer forms a hydrophilic group-containing polymer forms layer on a substrate, the polymer may be crosslinked by including a crosslinker in the polymer dispersion used for coating or electrospinning. In some embodiments, including, for example, when the polymer is disposed within a substrate, the hydrophilic group-containing polymer may be crosslinked by including a crosslinker in a dispersion used to introduce the hydrophilic group-containing polymer. In some embodiments, the dispersion is preferably a solution.

Any suitable crosslinker for use with the hydrophilic group-containing polymer may be selected. For example, N-(2-Aminoethyl)-3-aminopropyltrimethoxysilane (DAMO-T) may be used as a crosslinker for PHEM. For example, (3-glycidyloxypropyl) trimethoxy silane or poly(ethylene glycol) diacrylate (PEGDA) may be used as a crosslinker for polyethyleneimine (PEI). Hydrophilic group-containing polymers including primary or secondary amine groups could be crosslinked by, for example, compounds including carboxylic acids (adipic acid), aldehydes (for example, gluteraldehyde), ketones, melamine-formaldehyde resins, phenol-formaldehyde resins, etc. In another example, hydrophilic group-containing polymers containing primary or secondary alcohol groups could be crosslinked by, for example, compounds including carboxylic acids (adipic acid), isocyanates (toluene diisocyanate), organic silanes (tetramethoxysilane), titanium(IV) complexes (tetrabutyltitanate), phenol-formaldehyde resins, melamine-formaldehyde resins, etc.

In some embodiments, crosslinking of the hydrophilic group-containing polymer may accelerated by exposing the hydrophilic group-containing polymer and the crosslinker to heat. The heat may be applied by any suitable method including, for example, by heating the substrate in an oven, exposing the substrate to an infrared light, exposing the substrate to steam, or treating the substrate with heated rollers. Any combination of time and temperature suitable for use with the hydrophilic group-containing polymer, crosslinker, and substrate may be used. In some embodiments, the hydrophilic group-containing polymer and the crosslinker may be exposed to temperatures of at least 80° C., at least 90° C., at least 100° C., at least 110° C., at least 120° C., at least 130° C., at least 140° C., at least 150° C., at least 160° C., at least 170° C., at least 180° C., or at least 190° C. In some embodiments, the hydrophilic group-containing polymer and the crosslinker may be exposed to temperatures of up to 140° C., up to 150° C., up to 160° C., up to 170° C., up to 180° C., up to 190° C., up to 200° C., up to 210° C., up to 220° C., up to 230° C., up to 240° C., up to 260° C., up to 280° C., or up to 300° C. In some embodiments, the hydrophilic group-containing polymer and the crosslinker may be exposed to a heat treatment for at least 15 seconds, at least 30 seconds, at least 60 seconds, at least 120 seconds, at least 2 minutes, at least 5 minutes, at least 10 minutes, or at least 1 hour. In some embodiments, the media is exposed to heat for up to 2 minutes, up to 3 minutes, up to 5 minutes, up to 10 minutes, up to 15 minutes, up to 20 minutes, up to 1 hour, up to 2 hours, up to 24 hours, or up to 2 days. For example, in some embodiments, the hydrophilic group-containing polymer may be crosslinked by heating the hydrophilic group-containing polymer and the crosslinker at a temperature of at least 100° C. and up to 150° C. for between 15 seconds and 15 minutes. In another example, in some embodiments, the hydrophilic group-containing polymer may be crosslinked by heating the hydrophilic group-containing polymer and the crosslinker at a temperature of at least 80° C. and up to 200° C. for between 15 seconds and 15 minutes.

In some embodiments, the hydrophilic group-containing polymer may be annealed. As used herein, "annealing" includes exposing a hydrophilic group-containing polymer to an environment with the purpose of reorienting functional groups within the hydrophilic group-containing polymer and/or increasing the crystallinity of the hydrophilic group-containing polymer. If crosslinking of the hydrophilic group-containing polymer is accelerated by exposing the hydrophilic group-containing polymer and the crosslinker to heat, the hydrophilic group-containing polymer may be annealed before crosslinking, during crosslinking, or after crosslinking. In some embodiments, if crosslinking of the hydrophilic group-containing polymer is accelerated by exposing the hydrophilic group-containing polymer and the crosslinker to heat, the hydrophilic group-containing polymer may preferably be annealed during crosslinking or after crosslinking. In some embodiments, the hydrophilic group-containing polymer may preferably be annealed after crosslinking.

In some embodiments, annealing includes heating the substrate including the hydrophilic group-containing polymer in the presence of a polar solvent. For example, annealing may include submerging a hydrophilic group-containing polymer-containing and/or a hydrophilic group-containing polymer-coated substrate in a polar solvent. Additionally or alternatively, annealing may include exposing a hydrophilic group-containing polymer-containing and/or a hydrophilic group-containing polymer-coated substrate to a polar solvent in the form of steam. In some embodiments, including, for example, when a hydrophilic group-containing polymer layer is applied by dip coating a substrate in a polymer solution, the polymer solution may include a polar solvent, and heating and subsequent evaporation of the polar solvent from the substrate may anneal the polymer layer.

A polar solvent suitable for annealing may include, for example, water or an alcohol. An alcohol may include, for example, methanol, ethanol, isopropanol, t-butanol, etc. Other suitable polar solvents may include, for example, acetone, ethyl acetate, methyl ethyl ketone (MEK), dimethylformamide (DMF), etc.

In some embodiments, annealing includes exposing the substrate to a temperature of at least the glass transition temperature (Tg) of the hydrophilic group-containing polymer. In some embodiments, annealing includes exposing the substrate to a solvent having a temperature of at least the Tg of the hydrophilic group-containing polymer.

In some embodiments, including for example, when annealing includes submerging the hydrophilic group-containing polymer-coated substrate in a polar solvent, the polar solvent is at least 50° C., at least 55° C., at least 60° C., at least 65° C., at least 70° C., at least 75° C., at least 80° C., at least 85° C., at least 90° C., at least 95° C., at least 100° C., at least 110° C., at least 120° C., at least 130° C., at least 140° C., or at least 150° C. In some embodiments, the polar solvent is up to 90° C., up to 95° C., up to 100° C., up to 105° C., up to 110° C., up to 115° C., up to 120° C., up to 130° C., up to 140° C., up to 150° C., or up to 200° C. In some embodiments, the media is submerged in the polar solvent for at least 10 seconds, at least 30 seconds, at least 60 seconds, at least 90 seconds, at least 120 seconds, at least 150 seconds, or at least 180 seconds. In some embodiments, the media is submerged in the polar solvent for up to 60 seconds, up to 120 seconds, up to 150 seconds, up to 180 seconds, up to 3 minutes, or up to 5 minutes. In some embodiments, the polar solvent may preferably be water. For example, in some embodiments, annealing includes submerging the hydrophilic group-containing polymer-coated media in 90° C. water for at least 10 seconds and up to 5 minutes.

Without wishing to be bound by theory, it is believed that the surface of the substrate having a hydrophilic group-containing polymer disposed thereon or including a hydrophilic group-containing polymer disposed therein may have the desired properties (including roll off angle and contact angle), described above, because of discontinuities on the substrate surface. Accordingly, in some embodiments, the substrate may include a mixture of fibers. In some embodiments, the substrate may include both non-polymer and polymer fibers and/or two different types of polymer fibers. For example, the substrate could include, polyester fibers discontinuously wrapped with nylon and/or nylon fibers discontinuously wrapped with polyester. Additionally or alternatively, the substrate may include a fiber that, if it formed the entire surface, would create a hydrophilic surface and a fiber that, if it formed the entire surface, would create a hydrophobic surface.

In some embodiments, a substrate including a hydrophilic group-containing polymer—including a substrate including a hydrophilic group-containing polymer coating or a substrate including a hydrophilic group-containing polymer disposed therein—is preferably stable. In some embodiments, the stability of a substrate including a hydrophilic group-containing polymer may be increased by treating with maleic anhydride, annealing the hydrophilic group-containing polymer, and/or crosslinking the hydrophilic group-containing polymer. Without wishing to be bound by theory, in some embodiments, stability of a substrate including a hydrophilic group-containing polymer is believed to be increased by decreasing the solubility of the hydrophilic group-containing polymer—including, for example, by crosslinking. Again, without wishing to be bound by theory, in some embodiments, it is believed that the stability of a substrate may to be increased by increasing the accessibility of a polymer's hydrophilic pendant group (for example, a hydroxyl group) on a surface of a substrate—including, for example, by annealing.

Treated Substrates and Uses

In some embodiments, the disclosure relates to a filter media including a substrate obtainable by a method that includes exposing a surface of the substrate to UV radiation. The substrate includes at least one of an aromatic component and an unsaturated component.

In some embodiments, the surface of the substrate, prior to treatment, preferably has a contact angle of at least 90 degrees, as further described herein.

In some embodiments, exposing a surface of the substrate to UV radiation includes exposing the surface to UV radiation in the presence of oxygen, as further described herein. In some embodiments, exposing a surface of the substrate to UV radiation includes exposing the surface to UV radiation and at least one of $H_2O_2$ and ozone, as further described herein. In some embodiments, the substrate includes a UV-reactive resin, that is, a resin including at least one of an aromatic component and an unsaturated component. In some embodiments, the UV-reactive resin includes a phenolic resin.

In some embodiments, the disclosure relates to a filter media including a substrate obtainable by a method that includes disposing a hydrophilic group-containing polymer on a surface of the substrate.

In some embodiments, the surface of the substrate, prior to treatment, preferably has a contact angle of at least 90 degrees, as further described herein.

In some embodiments, the disclosure relates to the use of UV radiation to improve the roll off angle of a surface of a substrate, the substrate including at least one of an aromatic component and an unsaturated component.

In some embodiments, the use is characterized by the substrate including an aromatic resin.

In some embodiments, the use is characterized by the substrate including a phenolic resin.

In some embodiments, the use is characterized by the use of UV radiation in the presence of at least one of oxygen, ozone, and $H_2O_2$.

In some embodiments, the disclosure relates to the use of a substance obtainable by exposure of at least one of an aromatic component and an unsaturated component to UV radiation to improve the roll off angle of a substrate.

In some embodiments, the use relates to a use of a substance obtainable by exposure of a UV-reactive resin to UV radiation to improve the roll off angle of a substrate.

In some embodiments, the use relates to a use of a substance obtainable by exposure of an aromatic resin to UV radiation to improve the roll off angle of a substrate.

In some embodiments, the use relates to a use of a substance obtainable by exposure of a phenolic resin to UV radiation to improve the roll off angle of a substrate.

In some embodiments, the use is characterized by exposure to UV radiation in the presence of at least one of oxygen, ozone, and $H_2O_2$.

The disclosure also relates to the use of a hydrophilic group-containing polymer to improve the roll off angle of a substrate.

The disclosure further relates to the use of a hydrophilic polymer to improve the roll off angle of a substrate.

In some embodiments of these uses, the substrate is preferably a filter substrate, including, for instance, a filter substrate having a contact angle in a range of 90 degrees to 180 degrees for a 20 μL water droplet when the surface is immersed in toluene, as further described herein.

In some embodiments of these uses, the substrate is preferably a filter substrate, including, for instance, a filter substrate having a contact angle in a range of 90 degrees to 180 degrees for a 50 μL water droplet when the surface is immersed in toluene, as further described herein.

EXEMPLARY FILTER MEDIA EMBODIMENTS

Embodiment 1

A filter media comprising a substrate, wherein the substrate comprises a surface having a roll off angle in a range of 50 degrees to 90 degrees and a contact angle in a range of 90 degrees to 180 degrees for a 20 μL water droplet when the surface is immersed in toluene.

Embodiment 2

The filter media of embodiment 1, wherein the surface has a roll off angle in a range of 60 degrees to 90 degrees, in a range of 70 degrees to 90 degrees, or in a range of 80 degrees to 90 degrees.

Embodiment 3

A filter media comprising a substrate, wherein the substrate comprises a surface having a roll off angle in a range of 40 degrees to 90 degrees and a contact angle in a range of 90 degrees to 180 degrees for a 50 μL water droplet when the surface is immersed in toluene.

Embodiment 4

The filter media of embodiment 3, wherein the surface has a roll off angle in a range of 50 degrees to 90 degrees, in a range of 60 degrees to 90 degrees, in a range of 70 degrees to 90 degrees, or in a range of 80 degrees to 90 degrees.

Embodiment 5

The filter media of any one of embodiments 1 to 4, wherein the surface comprises a UV-treated surface.

Embodiment 6

The filter media of any one of any one of embodiments 1 to 5, wherein the surface comprises a UV-oxygen-treated surface.

Embodiment 7

The filter media of any one of any one of embodiments 1 to 6, wherein the surface comprises a UV-ozone-treated surface.

Embodiment 8

The filter media of any one of any one of embodiments 1 to 7, wherein the surface comprises a UV-$H_2O_2$-treated surface.

Embodiment 9

The filter media of any one of embodiments 1 to 8, wherein the substrate comprises a hydrophilic group-containing polymer.

Embodiment 10

The filter media of any one of embodiments 1 to 9, wherein the surface comprises a hydrophilic group-containing polymer disposed thereon.

Embodiment 11

The filter media of either of embodiments 9 or 10, wherein the hydrophilic group-containing polymer comprises a hydrophilic pendant group.

Embodiment 12

The filter media of any one of embodiments 9 to 11, wherein the hydrophilic group-containing polymer comprises poly(hydroxypropyl methacrylate) (PHPM), poly(2-hydroxyethyl methacrylate) (PHEM), poly(2-ethyl-2-oxazoline) (P2E2O), polyethyleneimine (PEI), quaternized polyethyleneimine, poly(dopamine), or combinations thereof.

Embodiment 13

The filter media of any one of embodiments 9 to 12, wherein the hydrophilic group-containing polymer comprises a hydrophilic polymer.

Embodiment 14

The filter media of any one of embodiments 9 to 13, wherein the hydrophilic group-containing polymer comprises a charged polymer.

Embodiment 15

The filter media of any one of embodiments 9 to 14, wherein the hydrophilic group-containing polymer comprises a hydroxylated methacrylate polymer.

Embodiment 16

The filter media of any one of embodiments 9 to 15, wherein the hydrophilic group-containing polymer does not comprise a fluoropolymer.

Embodiment 17

A filter media comprising a substrate,
wherein the substrate comprises a surface having a roll off angle in a range of 50 degrees to 90 degrees and a contact angle in a range of 90 degrees to 180 degrees for a 20 µL water droplet when the surface is immersed in toluene; and
wherein the surface comprises poly(hydroxypropyl methacrylate) (PHPM), poly(2-hydroxyethyl methacrylate) (PHEM), poly(2-ethyl-2-oxazoline) (P2E2O), polyethyleneimine (PEI), quaternized polyethyleneimine, poly(dopamine), or combinations thereof.

Embodiment 18

The filter media of embodiment 17, wherein the surface has a roll off angle in a range of 60 degrees to 90 degrees, in a range of 70 degrees to 90 degrees, or in a range of 80 degrees to 90 degrees.

Embodiment 19

A filter media comprising a substrate,
wherein the substrate comprises a surface having a roll off angle in a range of 40 degrees to 90 degrees and a contact angle in a range of 90 degrees to 180 degrees for a 50 µL water droplet when the surface is immersed in toluene; and
wherein the surface comprises poly(hydroxypropyl methacrylate) (PHPM), poly(2-hydroxyethyl methacrylate) (PHEM), poly(2-ethyl-2-oxazoline) (P2E2O), polyethyleneimine (PEI), quaternized polyethyleneimine, poly(dopamine), or combinations thereof.

Embodiment 20

The filter media of embodiment 19, wherein the surface has a roll off angle in a range of 50 degrees to 90 degrees, in a range of 60 degrees to 90 degrees, in a range of 70 degrees to 90 degrees, or in a range of 80 degrees to 90 degrees.

Embodiment 21

The filter media of any one of embodiments 1 to 20, wherein the substrate comprises cellulose, polyester, polyamide, polyolefin, glass, or a combination thereof.

Embodiment 22

The filter media of any one of embodiments 1 to 21, wherein the substrate comprises at least one of an aromatic component and an unsaturated component.

Embodiment 23

The filter media of any one of any one of embodiments 1 to 22, wherein the substrate comprises a modifying resin.

Embodiment 24

The filter media of any one of any one of embodiments 1 to 23, wherein the substrate comprises a UV-reactive resin.

Embodiment 25

The filter media of any one of any one of embodiments 1 to 24, wherein the substrate comprises a phenolic resin.

Embodiment 26

The filter media of any one of embodiments 1 to 25, wherein the substrate comprises pores having an average diameter of up to 2 mm.

Embodiment 27

The filter media of any one of embodiments 1 to 26, wherein the substrate comprises pores having an average diameter in a range of 40 µm to 50 µm.

Embodiment 28

The filter media of any one of embodiments 1 to 27, wherein the substrate is at least 15% porous and up to 99% porous.

Embodiment 29

The filter media of any one of embodiments 1 to 28, wherein the filter media further comprises a coalescing layer located upstream of the substrate.

Embodiment 30

The filter media of embodiment 29, wherein the coalescing layer comprises pores having an average diameter and the substrate comprises pores having an average diameter, and the average diameter of the pores of the substrate is greater than the average diameter of the pores of the coalescing layer.

Embodiment 31

The filter media of either of embodiments 29 or 30, wherein the substrate comprises pores having an average diameter, and wherein a droplet having an average diameter forms on a downstream side of the coalescing layer, and further wherein the average diameter of the pores of the substrate is greater than the average diameter of the droplet.

Embodiment 32

The filter media of any one of embodiments 1 to 31, wherein the substrate is stable.

EXEMPLARY METHOD OF TREATMENT EMBODIMENTS

Embodiment 1

A method of treating a material comprising a surface, the method comprising treating the surface to form a treated surface, wherein the treated surface has a roll off angle in a range of 50 degrees to 90 degrees and a contact angle in a range of 90 degrees to 180 degrees for a 20 µL water droplet when the surface is immersed in toluene.

Embodiment 2

The method of embodiment 1, wherein the treated surface has a roll off angle in a range of 60 degrees to 90 degrees, in a range of 70 degrees to 90 degrees, or in a range of 80 degrees to 90 degrees.

Embodiment 3

A method of treating a material comprising a surface, the method comprising
treating the surface to form a treated surface,
wherein the treated surface has a roll off angle in a range of 40 degrees to 90 degrees and a contact angle in a range of 90 degrees to 180 degrees for a 50 µL water droplet when the surface is immersed in toluene.

Embodiment 4

The method of embodiment 3, wherein the treated surface has a roll off angle in a range of 50 degrees to 90 degrees, in a range of 60 degrees to 90 degrees, in a range of 70 degrees to 90 degrees, or in a range of 80 degrees to 90 degrees.

Embodiment 5

The method of any one of embodiments 1 to 4, wherein treating the surface comprises exposing the surface to ultraviolet (UV) radiation.

Embodiment 6

The method of embodiment 5, wherein treating the surface comprises exposing the surface to ultraviolet (UV) radiation in the presence of oxygen, and wherein the UV radiation comprises a first wavelength in a range of 180 nm to 210 nm and a second wavelength in a range of 210 nm to 280 nm.

Embodiment 7

The method of any one of embodiments 1 to 6, wherein the UV radiation comprises a wavelength of 185 nm.

Embodiment 8

The method of any one of embodiments 1 to 7, wherein the UV radiation comprises a wavelength of 254 nm.

Embodiment 9

The method of any one of embodiments 1 to 8, wherein treating the surface comprises exposing the surface to $H_2O_2$.

Embodiment 10

The method of any one of embodiments 1 to 9, wherein treating the surface comprises exposing the surface to ultraviolet (UV) radiation comprising a wavelength in a range of 350 nm to 370 nm.

Embodiment 11

The method of any one of embodiments 1 to 10, wherein treating the surface comprises exposing the surface to ultraviolet (UV) radiation in the presence of ozone.

Embodiment 12

The method of any one of embodiments 1 to 11, wherein treating the surface comprises exposing the surface to UV radiation in a range of 300 µW/cm$^2$ to 200 mW/cm$^2$.

Embodiment 13

The method of any one of embodiments 1 to 12, wherein treating the surface comprises exposing the surface to UV radiation for a time in a range of 2 seconds to 20 minutes.

Embodiment 14

The method of any one of embodiments 1 to 13, wherein treating the surface comprises forming a layer comprising a hydrophilic group-containing polymer on the surface.

Embodiment 15

The method of embodiment 14, wherein the hydrophilic group-containing polymer comprises poly(hydroxypropyl methacrylate) (PHPM), poly(2-hydroxyethyl methacrylate) (PHEM), poly(2-ethyl-2-oxazoline) (P2E2O), polyethyleneimine (PEI), quaternized polyethyleneimine, poly(dopamine), or combinations thereof.

Embodiment 16

The method of either of embodiments 14 or 15, wherein the hydrophilic group-containing polymer comprises a hydrophilic polymer.

Embodiment 17

The method of any one of embodiments 14 to 16, wherein the hydrophilic group-containing polymer comprises a hydrophilic pendant group.

Embodiment 18

The method of any one of embodiments 14 to 17, wherein the hydrophilic group-containing polymer comprises a hydroxylated methacrylate polymer.

Embodiment 19

The method of any one of embodiments 14 to 18, wherein the hydrophilic group-containing polymer does not comprise a fluoropolymer.

Embodiment 20

The method of any one of embodiments 14 to 19, wherein the layer comprises a charged layer.

Embodiment 21

The method of any one of embodiments 14 to 20, wherein forming a layer comprising a hydrophilic group-containing polymer comprises dip coating the material in a solution comprising the hydrophilic group-containing polymer.

Embodiment 22

The method of embodiment 21, wherein the solution comprising the hydrophilic group-containing polymer further comprises a crosslinker.

Embodiment 23

The method of embodiment 22, wherein the crosslinker comprises at least one of N-(2-Aminoethyl)-3-aminopropyltrimethoxysilane (DAMO-T), 3-glycidyloxypropyl) trimethoxy silane and poly (ethylene glycol) diacrylate (PEGDA).

Embodiment 24

The method of any one of embodiments 14 to 20, wherein forming a layer comprising a hydrophilic group-containing polymer on the surface comprises electrospinning a solution comprising a hydrophilic group-containing polymer onto the surface.

Embodiment 25

The method of embodiment 24, the method further comprising forming nanofibers comprising the hydrophilic group-containing polymer on the surface.

Embodiment 26

The method of either of embodiments 24 or 25, wherein the solution comprising a hydrophilic group-containing polymer further comprises a crosslinker.

Embodiment 27

The method of embodiment 26, wherein the crosslinker comprises at least one of N-(2-Aminoethyl)-3-aminopropyltrimethoxysilane (DAMO-T), 3-glycidyloxypropyl) trimethoxy silane and poly (ethylene glycol) diacrylate (PEGDA).

Embodiment 28

The method of any one of embodiments 14 to 27, the method further comprising crosslinking the hydrophilic group-containing polymer.

Embodiment 29

The method of Embodiment 28, wherein crosslinking the hydrophilic group-containing polymer comprises heating the hydrophilic group-containing polymer-coated material at a temperature in a range of 80° C. to 200° C. for 30 seconds to 15 minutes.

Embodiment 30

The method of any one of embodiments 14 to 29, the method further comprising annealing the hydrophilic group-containing polymer.

Embodiment 31

The method of Embodiment 30, wherein annealing the hydrophilic group-containing polymer comprises submerging the hydrophilic group-containing polymer-coated material in a solvent for at least 10 seconds, wherein the temperature of the solvent is at least the glass transition temperature of the hydrophilic group-containing polymer.

Embodiment 32

The method of any one of embodiments 1 to 31, wherein the material comprises a filter media.

Embodiment 33

The method of embodiment 32, wherein the filter media comprises a substrate.

Embodiment 34

The method of any one of embodiments 1 to 33, wherein the material comprises cellulose, polyester, polyamide, polyolefin, glass, or a combination thereof.

Embodiment 35

The method of any one of embodiments 1 to 34, wherein the material comprises a at least one of an aromatic component and an unsaturated component.

Embodiment 36

The method of any one of embodiments 1 to 35, wherein the material comprises a modifying resin.

Embodiment 37

The method of any one of embodiments 1 to 36, wherein the material comprises a UV-reactive resin.

Embodiment 38

The method of any one of embodiments 1 to 37, wherein the material comprises a phenolic resin.

Embodiment 39

The method of any one of embodiments 1 to 38, wherein the material comprises pores having an average diameter of up to 2 mm.

Embodiment 40

The method of any one of embodiments 1 to 39, wherein the material comprises pores having an average diameter in a range of 40 μm to 50 μm.

Embodiment 41

The method of any one of embodiments 1 to 40, wherein the material is at least 15% porous and up to 99% porous.

Embodiment 42

The method of any one of embodiments 1 to 41, wherein the treated surface is stable.

Embodiment 43

The method of any one of embodiments 1 to 42, wherein the surface of the material, prior to treatment, has a contact angle in a range of 90 degrees to 180 degrees for a 20 μL water droplet when the surface is immersed in toluene.

Embodiment 44

The method of any one of embodiments 1 to 43, wherein the surface of the material, prior to treatment, has a contact angle in a range of 100 degrees to 150 degrees for a 20 μL water droplet when the surface is immersed in toluene.

Embodiment 45

The method of any one of embodiments 1 to 44, wherein the surface of the material, prior to treatment, has a roll off angle in a range of 0 degrees to 50 degrees for a 20 μL water droplet when the surface is immersed in toluene.

Embodiment 46

The method of any one of embodiments 1 to 42, wherein the surface of the material, prior to treatment, has a contact angle in a range of 90 degrees to 180 degrees for a 50 μL water droplet when the surface is immersed in toluene.

Embodiment 47

The method of any one of embodiments 1 to 42 or 46, wherein the surface of the material, prior to treatment, has a contact angle in a range of 100 degrees to 150 degrees for a 50 μL water droplet when the surface is immersed in toluene.

Embodiment 48

The method of any one of embodiments 1 to 42, 46, or 47 wherein the surface of the material, prior to treatment, has a roll off angle in a range of 0 degrees to 40 degrees for a 50 μL water droplet when the surface is immersed in toluene.

EXEMPLARY FILTER ELEMENT EMBODIMENTS

Embodiment 1

A filter element comprising:
a filter media comprising a substrate, wherein the substrate comprises a surface having a roll off angle in a range of 50 degrees to 90 degrees and a contact angle in a range of 90 degrees to 180 degrees for a 20 μL water droplet when the surface is immersed in toluene.

Embodiment 2

The filter element of embodiment 1, wherein the surface has a roll off angle in a range of 60 degrees to 90 degrees, in a range of 70 degrees to 90 degrees, or in a range of 80 degrees to 90 degrees.

Embodiment 3

A filter element comprising a filter media comprising a substrate, wherein the substrate comprises a surface having a roll off angle in a range of 40 degrees to 90 degrees and a contact angle in a range of 90 degrees to 180 degrees for a 50 μL water droplet when the surface is immersed in toluene.

Embodiment 4

The filter element of embodiment 3, wherein the surface has a roll off angle in a range of 50 degrees to 90 degrees, in a range of 60 degrees to 90 degrees, in a range of 70 degrees to 90 degrees, or in a range of 80 degrees to 90 degrees.

Embodiment 5

The filter element of any one of embodiments 1 to 4, wherein the surface defines a downstream side of the filter media.

Embodiment 6

The filter element of any one of embodiments 1 to 5, wherein the filter media comprises a layer configured to remove particulate contaminants.

Embodiment 7

The filter element of embodiment 6, wherein the layer configured to remove particulate contaminants is upstream of the substrate.

Embodiment 8

The filter element of any one of embodiments 1 to 7, wherein the filter media comprises a coalescing layer.

Embodiment 9

The filter element of embodiment 8, wherein the coalescing layer is upstream of the substrate.

Embodiment 10

The filter element of any one of embodiments 1 to 9, wherein the filter media comprises a layer configured to remove particulate contaminants and a coalescing layer, and the layer configured to remove particulate contaminants is upstream of the coalescing layer and the coalescing layer is upstream of the substrate.

Embodiment 11

The filter element of any one of embodiments 1 to 10, the filter element further comprising a screen.

Embodiment 12

The filter element of embodiment 11, wherein the screen is downstream of the substrate.

Embodiment 13

The filter element of any one of embodiments 1 to 12, the filter element further comprising a second coalescing layer downstream of the substrate.

Embodiment 14

The filter element of any one of embodiments 1 to 13, wherein the filter media has a tubular configuration.

Embodiment 15

The filter element of any one of embodiments 1 to 14, wherein the filter media comprises pleats.

Embodiment 16

The filter element of any one of embodiments 1 to 15, wherein the filter element is configured to remove water from a hydrocarbon fluid.

Embodiment 17

The filter element of embodiment 16, wherein the hydrocarbon fluid comprises diesel fuel.

Embodiment 18

The filter element of any one of embodiments 1 to 17, wherein the surface is stable.

Exemplary Methods of Identifying Material Suitable for Hydrocarbon Fluid-Water Separation

Embodiment 1

A method for identifying a material suitable for hydrocarbon fluid-water separation, the method comprising determining the roll off angle of a droplet on a surface of the material, wherein the material is immersed in a fluid comprising a hydrocarbon, and wherein the roll off angle is in a range of 40 degrees to 90 degrees.

Embodiment 2

The method of embodiment 1, wherein the droplet comprises a hydrophile.

Embodiment 3

The method of either of embodiments 1 or 2, wherein the droplet comprises water.

Embodiment 4

The method of any one of embodiments 1 to 3, wherein the fluid comprising a hydrocarbon comprises toluene.

Embodiment 5

The method of any one of embodiments 1 to 4, wherein the droplet is a 20 µL droplet.

Embodiment 6

The method of any one of embodiments 1 to 4, wherein the droplet is a 50 µL droplet.

Embodiment 7

The method of any one of embodiments 1 to 6, wherein the method further comprises determining the contact angle of the droplet on the surface of the material.

Embodiment 8

The method of embodiment 7, wherein the contact angle is in a range of 90 degrees to 180 degrees.

Embodiment 9

The method of any one of embodiments 1 to 8, wherein the material comprises a hydrophilic group-containing polymer disposed thereon.

Embodiment 10

The method of embodiment 10, wherein the hydrophilic group-containing polymer comprises a hydrophilic polymer.

Embodiment 11

The method of any one of embodiments 1 to 10, wherein the surface of the material is stable.

Embodiment 12

The method of any one of embodiments 1 to 11, wherein the material comprises pores having an average diameter of up to 2 mm.

Embodiment 13 method of any one of embodiments 1 to 12, wherein the material comprises pores having an average diameter in a range of 40 µm to 50 µm.

Embodiment 14 method of any one of embodiments 1 to 13, wherein the material is at least 15% porous and up to 99% porous.

EXEMPLARY UV RADIATION-TREATED SUBSTRATE EMBODIMENTS

Embodiment 1

A filter media comprising a substrate obtainable by a method comprising:
exposing a surface of the substrate to ultraviolet (UV) radiation, wherein the substrate comprises at least one of an aromatic component and an unsaturated component.

Embodiment 2

The filter media of embodiment 1, wherein the surface of the substrate, prior to treatment, has a contact angle in a range of 90 degrees to 180 degrees for a 20 µL water droplet when the surface is immersed in toluene.

Embodiment 3

The filter media of either of embodiments 1 or 2, wherein the surface of the substrate, prior to treatment, has a contact angle in a range of 100 degrees to 150 degrees for a 20 µL water droplet when the surface is immersed in toluene.

Embodiment 4

The filter media of embodiment 1, wherein the surface of the substrate, prior to treatment, has a contact angle in a range of 90 degrees to 180 degrees for a 50 µL water droplet when the surface is immersed in toluene.

Embodiment 5

The filter media of either of embodiments 1 or 4, wherein the surface of the substrate, prior to treatment, has a contact angle in a range of 100 degrees to 150 degrees for a 50 µL water droplet when the surface is immersed in toluene.

Embodiment 6

A filter media comprising a substrate obtainable by a method comprising
providing a substrate comprising at least one of an aromatic component and an unsaturated component, the substrate having a surface having a contact angle in a range of 90 degrees to 180 degrees for a 20 µL water droplet when the surface is immersed in toluene, and
exposing a surface of the substrate to ultraviolet (UV) radiation.

Embodiment 7

The filter media of embodiment 6, wherein the surface of the substrate, prior to treatment, has a contact angle in a range of 100 degrees to 150 degrees for a 20 µL water droplet when the surface is immersed in toluene.

Embodiment 8

A filter media comprising a substrate obtainable by a method comprising
providing a substrate comprising at least one of an aromatic component and an unsaturated component, the substrate having a surface, the surface having, prior to treatment, a contact angle in a range of 90 degrees to 180 degrees for a 50 µL water droplet when the surface is immersed in toluene, and
exposing a surface of the substrate to ultraviolet (UV) radiation.

Embodiment 9

The filter media of embodiment 8, wherein the surface of the substrate, prior to treatment, has a contact angle in a range of 100 degrees to 150 degrees for a 50 µL water droplet when the surface is immersed in toluene.

Embodiment 10

The filter media of any one of embodiments 1 to 9, wherein exposing the surface of the substrate to UV radiation comprises exposing the surface to UV radiation in the presence of oxygen, and wherein the UV radiation comprises a first wavelength in a range of 180 nm to 210 nm and a second wavelength in a range of 210 nm to 280 nm.

Embodiment 11

The filter media of any one of embodiments 1 to 10, wherein the UV radiation comprises a wavelength of 185 nm.

Embodiment 12

The filter media of any one of embodiments 1 to 11, wherein the UV radiation comprises a wavelength of 254 nm.

Embodiment 13

The filter media of any one of embodiments 1 to 12, wherein exposing the surface comprises exposing the surface to $H_2O_2$.

Embodiment 14

The filter media of any one of embodiments 1 to 13, wherein exposing the surface comprises exposing the surface to UV radiation comprising a wavelength in a range of 350 nm to 370 nm.

Embodiment 15

The filter media of any one of embodiments 1 to 14, wherein exposing the surface comprises exposing the surface to UV radiation in the presence of ozone.

Embodiment 16

The filter media of any one of embodiments 1 to 15, wherein exposing the surface comprises exposing the surface to UV radiation in a range of 300 $\mu W/cm^2$ to 200 $mW/cm^2$.

Embodiment 17

The filter media of any one of embodiments 1 to 16, wherein exposing the surface comprises exposing the surface to UV radiation for a time in a range of 2 seconds to 20 minutes.

Embodiment 18

The filter media of any one of embodiments 1 to 17, wherein the substrate comprises an aromatic component and an unsaturated component.

Embodiment 19

The filter media of embodiment 18, wherein the substrate comprises a UV-reactive resin.

Embodiment 20

The filter media of either of embodiments 18 or 19, the UV-reactive resin comprising a phenolic resin.

Embodiment 21

The filter media of any one of embodiments 1 to 20, wherein the substrate comprises pores having an average diameter of up to 2 mm.

Embodiment 22

The filter media of any one of embodiments 1 to 21, wherein the substrate comprises pores having an average diameter in a range of 40 $\mu m$ to 50 $\mu m$.

Embodiment 23

The filter media of any one of embodiments 1 to 22, wherein the substrate is at least 15% porous and up to 99% porous.

Embodiment 24

The filter media of any one of embodiments 1 to 22, wherein the substrate, prior to treatment, has a roll off angle in a range of 0 degrees to 50 degrees for a 20 $\mu L$ water droplet when the surface is immersed in toluene.

Embodiment 25

The filter media of any one of embodiments 1 to 22, wherein the substrate, prior to treatment, has a roll off angle in a range of 0 degrees to 40 degrees for a 50 $\mu L$ water droplet when the surface is immersed in toluene.

EXEMPLARY HYDROPHILIC GROUP-CONTAINING POLYMER-TREATED SUBSTRATE EMBODIMENTS

Embodiment 1

A filter media comprising a substrate obtainable by a method comprising:
disposing a hydrophilic group-containing polymer on a surface of the substrate.

Embodiment 2

The filter media of embodiment 1, wherein the surface of the substrate, prior to treatment, has a contact angle in a range of 90 degrees to 180 degrees for a 20 $\mu L$ water droplet when the surface is immersed in toluene.

Embodiment 3

The filter media of either of embodiments 1 or 2, wherein the surface of the substrate, prior to treatment, has a contact angle in a range of 100 degrees to 150 degrees for a 20 $\mu L$ water droplet when the surface is immersed in toluene.

Embodiment 4

The filter media of embodiment 1, wherein the surface of the substrate, prior to treatment, has a contact angle in a range of 90 degrees to 180 degrees for a 50 $\mu L$ water droplet when the surface is immersed in toluene.

Embodiment 5

The filter media of either of embodiments 1 or 4, wherein the surface of the substrate, prior to treatment, has a contact angle in a range of 100 degrees to 150 degrees for a 50 $\mu L$ water droplet when the surface is immersed in toluene.

Embodiment 6

The filter media of any one of embodiments 1 to 5, wherein the hydrophilic group-containing polymer comprises poly(hydroxypropyl methacrylate) (PHPM), poly(2-hydroxyethyl methacrylate) (PHEM), poly(2-ethyl-2-oxazoline) (P2E2O), polyethyleneimine (PEI), quaternized polyethyleneimine, poly(dopamine), or combinations thereof.

Embodiment 7

The filter media of any one of embodiments 1 to 6, wherein the hydrophilic group-containing polymer comprises a hydrophilic polymer.

Embodiment 8

The filter media of any one of embodiments 1 to 7, wherein the hydrophilic group-containing polymer comprises a hydrophilic pendant group.

Embodiment 9

The filter media of any one of embodiments 1 to 8, wherein the hydrophilic group-containing polymer comprises a hydroxylated methacrylate polymer.

Embodiment 10

The filter media of any one of embodiments 1 to 9, wherein the hydrophilic group-containing polymer does not comprise a fluoropolymer.

Embodiment 11

The filter media of any one of embodiments 1 to 10, wherein disposing a hydrophilic group-containing polymer on the surface of the substrate comprises forming a layer comprising the hydrophilic group-containing polymer on the surface.

Embodiment 12

The filter media of embodiment 11, wherein the layer comprises a charged layer.

Embodiment 13

The filter media of any one of embodiments 1 to 12, wherein disposing a hydrophilic group-containing polymer on the surface of the substrate comprises dip coating the substrate in a solution comprising the hydrophilic group-containing polymer.

Embodiment 14

The filter media of embodiment 13, wherein the solution comprising the hydrophilic group-containing polymer further comprises a crosslinker.

Embodiment 15

The filter media of embodiment 14, wherein the crosslinker comprises at least one of N-(2-Aminoethyl)-3-aminopropyltrimethoxysilane (DAMO-T), 3-glycidyloxypropyl) trimethoxy silane and poly (ethylene glycol) diacrylate (PEGDA).

Embodiment 16

The filter media of any one of embodiments 1 to 12, wherein disposing a hydrophilic group-containing polymer on the surface of the substrate comprises electrospinning a solution comprising a hydrophilic group-containing polymer onto the surface.

Embodiment 17

The filter media of embodiment 16, wherein electrospinning a solution comprising a hydrophilic group-containing polymer onto the surface comprises forming nanofibers comprising the hydrophilic group-containing polymer on the surface.

Embodiment 18

The filter media of either of embodiments 16 or 17, wherein the solution comprising a hydrophilic group-containing polymer further comprises a crosslinker.

Embodiment 19

The filter media of embodiment 18, wherein the crosslinker comprises at least one of N-(2-Aminoethyl)-3-aminopropyltrimethoxysilane (DAMO-T), 3-glycidyloxypropyl) trimethoxy silane and poly (ethylene glycol) diacrylate (PEGDA).

Embodiment 20

The filter media of any one of embodiments 1 to 20, the method further comprising crosslinking the hydrophilic group-containing polymer.

Embodiment 21

The filter media of Embodiment 20, wherein crosslinking the hydrophilic group-containing polymer comprises heating the hydrophilic group-containing polymer-coated material at a temperature in a range of 80° C. to 200° C. for 30 seconds to 15 minutes.

Embodiment 22

The filter media of any one of embodiments 1 to 21, the method further comprising annealing the hydrophilic group-containing polymer.

Embodiment 23

The filter media of Embodiment 22, wherein annealing the hydrophilic group-containing polymer comprises submerging the hydrophilic group-containing polymer-coated material in a solvent for at least 10 seconds, wherein the temperature of the solvent is at least the glass transition temperature of the hydrophilic group-containing polymer.

Embodiment 24

The filter media of any one of embodiments 1 to 23, wherein the substrate comprises pores having an average diameter of up to 2 mm.

Embodiment 25

The filter media of any one of embodiments 1 to 24, wherein the substrate comprises pores having an average diameter in a range of 40 μm to 50 μm.

Embodiment 26

The filter media of any one of embodiments 1 to 25, wherein the substrate is at least 15% porous and up to 99% porous.

Embodiment 27

The filter media of any one of embodiments 1 to 26, wherein the substrate, prior to treatment, has a roll off angle in a range of 0 degrees to 50 degrees for a 20 μL water droplet when the surface is immersed in toluene.

Embodiment 28

The filter media of any one of embodiments 1 to 26, wherein the substrate, prior to treatment, has a roll off angle in a range of 0 degrees to 40 degrees for a 50 μL water droplet when the surface is immersed in toluene.

EXEMPLARY USE EMBODIMENTS

Embodiment 1

The use of ultraviolet (UV) radiation to improve the roll off angle of a surface of a substrate, the substrate comprising at least one of an aromatic component and an unsaturated component.

Embodiment 2

The use of embodiment 1, the use characterized by the substrate comprising an aromatic resin.

Embodiment 3

The use of either of embodiments 1 or 2, the use characterized by the substrate comprising a phenolic resin.

Embodiment 4

The use of any one of embodiments 1 to 3, the use characterized by the use of UV radiation in the presence of oxygen to improve the roll off angle.

Embodiment 5

The use of any one of embodiments 1 to 4, the use characterized by the use of UV radiation in the presence of ozone to improve the roll off angle.

Embodiment 6

The use of any one of embodiments 1 to 5, the use characterized by the use of UV radiation in the presence of $H_2O_2$ to improve the roll off angle.

Embodiment 7

The use of a substance obtainable by exposure of at least one of an aromatic component and an unsaturated component to UV radiation to improve the roll off angle of a substrate.

Embodiment 8

The use of embodiment 7, wherein the use relates to a use of a substance obtainable by exposure of a UV-reactive resin to UV radiation to improve the roll off angle of a substrate.

Embodiment 9

The use of either of embodiments 7 or 8, wherein the use relates to a use of a substance obtainable by exposure of a phenolic resin to UV radiation to improve the roll off angle of a substrate.

Embodiment 10

The use of any one of embodiments 7 to 9, the use characterized by exposure of at least one of an aromatic component and an unsaturated component to UV radiation in the presence of oxygen.

Embodiment 11

The use of any one of embodiments 7 to 9, the use characterized by exposure of at least one of an aromatic component and an unsaturated component to UV radiation in the presence of ozone.

Embodiment 12

The use of any one of embodiments 7 to 9, the use characterized by exposure of at least one of an aromatic component and an unsaturated component to UV radiation in the presence of $H_2O_2$.

Embodiment 13

The use of a hydrophilic group-containing polymer to improve the roll off angle of a substrate.

Embodiment 14

The use of a hydrophilic polymer to improve the roll off angle of a substrate.

Embodiment 15

The use of any one of embodiments 1 to 14 wherein the substrate is a filter substrate.

Embodiment 16

The use of embodiment 15, wherein the filter substrate has a contact angle in a range of 90 degrees to 180 degrees for a 20 μL water droplet when the surface is immersed in toluene.

Embodiment 17

The use of embodiment 15, wherein the filter substrate has a contact angle in a range of 90 degrees to 180 degrees for a 50 μL water droplet when the surface is immersed in toluene.

The present invention is illustrated by the following examples. It is to be understood that the particular examples, materials, amounts, and procedures are to be interpreted broadly in accordance with the scope and spirit of the invention as set forth herein.

Examples

Materials

All purchased materials were used as received (that is, with no further purification). Unless otherwise specified, materials were purchased from Sigma Aldrich (St. Louis, Mo.).
CHROMASOLV Isopropyl Alcohol (IPA)—99.9%
CHROMASOLV Toluene—99.9%
CHROMASOLV Ethyl Acetate—99.9%
Methyl Alcohol—ACS Reagent—99.8%
Ethyl Alcohol (EtOH)
Maleic Anhydride—99%
$H_2O_2$—30% or 50%
$NH_4OH$—ACS Reagent—50%
N-(2-Aminoethyl)-3-aminopropyltrimethoxysilane (also referred to as DYNASYLAN DAMO-T or DAMO-T)—Evonik Industries AG (Essen, Germany)

DYNASYLAN SIVO 203—Evonik Industries AG (Essen, Germany)
Tyzor 131 (Tyzor)
HCl in isopropyl alcohol (IPA)—0.05M
Poly(2-hydroxyethyl methacrylate) (PHEM)—Scientific Polymer Products (Ontario, N.Y.)—Mw=20,000
Poly(2-ethyl-2-oxazoline) (P2E2O)—Mw=50,000
Polyethyleneimine, branched (PEI-10K or PEI 10000)—Mw=25,000-Mn=10,000
Polyethyleneimine, branched (PEI-600)—Mw=600
Poly(hydroxypropyl methacrylate) (PHPM)—Scientific Polymer Products (Ontario, N.Y.)—Granular
Poly(ethylene oxide) diamine terminated (PEO-NH2)—Scientific Polymer Products (Ontario, N.Y.)—Mw=2000
Polystyrene-co-Allyl Alcohol (PS-co-AA)—40 mol %
Poly(acrylic acid) (PAA)
Acrodur 950L—BASF Corporation (Florham Park, N.J.)
3-glycidyloxypropyl) trimethoxy silane
poly (ethylene glycol) diacrylate (PEGDA)
Ultra-pure water was generated by treating tap water with Millipore Elix 10 UV and Millipore Milli-Q A10 modules and had a resistance of 18.2 MΩ*cm
Diesel fuel or Pump Fuel=Ultra-Low Sulfur Diesel (ULSD) that meets ASTM-D975. "Pump fuel" indicates that the sourced ULSD was used as-received from a fuel pump.
Bio Diesel=soy-based biodiesel that meets ASTM-D6751 (Renewable Energy Group (REG), Inc., Mason City, Iowa).

Test Procedures

Contact Angles and Roll-off Angles

The contact angle and the roll-off angle of a substrate were measured using a DropMaster DM-701 contact angle meter equipped with a tilt stage (Kyowa Interface Science Co., Ltd.; Niiza-City, Japan). Measurements were performed using the wide camera lens setting and calibrated using a 6 millimeter (mm) calibration standard with the FAMAS software package (Kyowa Interface Science Co., Ltd.; Niiza-City, Japan). Measurements were taken only after the droplet had reached equilibrium on the surface (that is, the contact angle and exposed droplet volume was constant for one minute). Measurements were taken of droplets that were in contact with only the substrate, that is, the droplet was not in contact with any surface supporting the substrate.

Water contact angles in toluene were measured using 20 μL drops or 50 μL drops of ultra-pure water deposited on a substrate sample that was submersed in toluene. Contact angles were measured using a tangent fit and were calculated from an average of five independent measurements taken on different areas of the substrate.

Water roll-off angles in toluene were measured using 20 μL drops or 50 μL drops of ultra-pure water deposited on a substrate sample that was submersed in toluene. The stage was set to rotate to 90° at a rotation speed of 2 degrees per second (°/sec). At the point when the water drop freely rolled away, or the rear contact line moved at least 0.4 millimeters (mm) relative to the media surface, the rotation was stopped. The angle at the time the rotation was stopped was measured; this angle is defined as the roll-off angle. If the droplet did not roll-off before 90 degrees (°), the value is reported as 90°. If the droplet rolled away during the deposition process, the value is reported at 1°. Exemplary images of water droplets on a substrate sample immersed in toluene are shown in FIG. 2. Reported values were calculated from an average of five independent measurements taken on different areas of media. Intentional depressions in the substrate (for example, point-bonding depressions) were avoided. If the substrate had a directional macrostructure (for example, corrugation), the roll-off angles were measured in a direction that minimized the effect of the macrostructure.

Droplet Sizing Test

Figure 3:
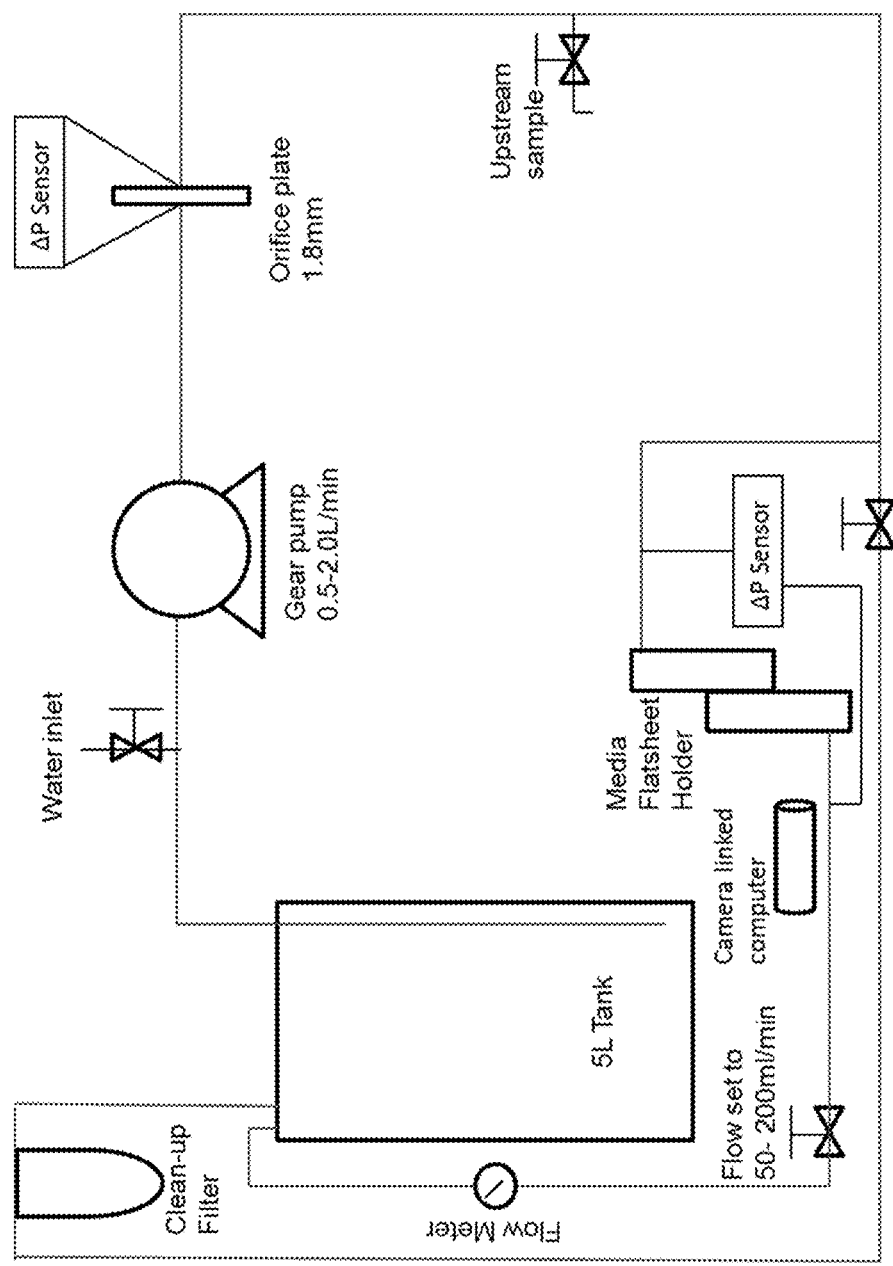
FIG. 3 shows a schematic of the two loop system used for the droplet sizing test.

To determine droplet sizing, a modified version of ISO 16332 was used. A 10 Liter (L) tank supplying a two loop system in multi-pass, shown in FIG. 3, was employed. A main loop handled the majority of the flow, and a test loop, including a media holder, provided a slipstream off the main loop. Manual back-pressure valves were used to regulate the flow to a face velocity of 0.07 feet per minute (ft/min) through the test media throughout the duration of the test. This face velocity is typical of values for in-the-field applications.

Two inch by two inch square samples of each layer were cut and then packed in to a multi-layer media composite including: a loading layer, an efficiency layer, and the substrate sample. The substrate sample to be tested was placed downstream of the efficiency layer, and the efficiency layer was placed downstream of the loading layer. The loading layer and the efficiency layer were thermally bonded sheets that included 20% to 80% bi-component binder fiber having a fiber diameter of 5 μm to 50 μm and a fiber length of 0.1 cm to 15 cm, glass fiber having a fiber diameter of 0.1 micron to 30 microns and an aspect ratio of 10 to 10,000, and have a pore size of 0.5 μm to 100 μm.

Once packed in to a multi-layer media composite, the media layers were held in a custom-built clear acrylic holder. Stainless steel ¼ inch outside diameter (OD) tubing, attached with National Pipe Thread Taper (NPT) fittings, was used to deliver fuel into and out of the from the test loop. The holder was 6 inches×4 inches with a 1 inch×1 inch sample window and a 1 inch×4 inch×¾ inch channel on the downstream side of the media to allow coalesced droplets to exit the fuel stream. As droplets exited the fuel stream, they passed through a zone where a charge-coupled device (CCD) camera captured images of the droplets. Image analysis software (Image J 1.47T, available on the world wide web at imagej.nih.gov) was used to analyze the captured images to determine droplet sizes. The measured droplet sizes were used for statistical analysis. Reported mean droplet sizes were volume weighted: D10 represents the diameter at which 10% of the droplets included a total water volume less than D10 and 90% of the droplets included a total water volume greater than D10; D50 represents the median diameter at which 50% of the droplets included a total water volume less than D50 and 50% of the droplets included a total water volume greater than D50; D90 represents the diameter at which 90% of the droplets included a total water volume less than D90 and 10% of the droplets included a total water volume greater than D90.

Ultra-Low Sulfur Diesel from Chevron Phillips Chemical (The Woodlands, Tex.) was used as a base fuel. 5% (by volume) soy biodiesel (Renewable Energy Group (REG), Inc., Mason City, Iowa) was added to the base fuel to form a fuel mixture. The interfacial tension of the fuel mixture was 21±2 dynes per centimeter, as determined by pendant drop method. The same batch of fuel mixture was used for all testing.

For testing, a multi-layer media composite was placed in the holder, and the holder was filled with the fuel mixture. A face velocity of 0.07 ft/min was set and manually maintained for 10 minutes prior to introducing water.

A water-in-fuel emulsion was generated by injecting water into the main fuel loop and forcing it through an orifice plate. To achieve the desired mean 20 μm emulsion, a 1.8 mm plate was used. The flow speed in the main loop was adjusted to achieve a differential pressure across the orifice plate of 5.0 pounds per square inch (psi) (approximately 1.2 Liters per minute (Lpm)). The water was injected at a rate of 0.3 milliliter per minute (mL/min) with an initial target challenge of 2500 parts per million (ppm) water. Fuel that was not taken into the test loop was sent through a clean-up filter before being directed back into the main tank where it could be passed through the orifice again. The system provides a consistent emulsion challenge to the multi-layer media composite during the duration of a 20 minute test.

Fuel-Water Separation Efficiency Test

Fuel-water separation efficiency testing was done using the ISO/TS 16332 laboratory test method, modified as described herein.

For testing flat-sheets of media, an aluminum holder that holds a 7 inch×7 inch sheet of filter media (effective size of 6 inches×6 inches) was used. On the downstream side of the filter media, a 100 μm polyester screen (effective size of 6 inches×6 inches) was placed to ensure that coalesced water droplets larger than 100 μm in diameter were not carried downstream with the fuel flow.

The upstream water concentration in fuel was set at 5000 ppm and is considered to be constant through the duration of the test. This concentration of water was determined by measuring the known flow rates of both the water injection pump and the fuel flow rate. The downstream water concentration was recorded at predetermined intervals. The water concentration was measured using a Karl-Fisher volumetric titration method using a commercial Metrohm AG (Herisau, Switzerland) 841 Titrando titrator.

The droplet size distribution of the upstream free water was determined using a commercial Malvern Instruments (Malvern, United Kingdom) Insitec SX droplet size analyzer with an attached wet flow cell. For an emulsified water test, the droplet size distribution typically has a D50 of 10 μm±1 μm with a D10 and D90 of 3 μm and 25 μm, respectively.

The face velocity across the media in all tests unless otherwise specified was fixed at 0.05 feet per minute (fpm or ft/min). Unless otherwise specified, the total test time was 15 minutes.

The percent separation efficiency of the media during the test was calculated as the ratio of the downstream water concentration to the upstream water concentration.

Permeability Test

A sample at least 38 cm$^2$ was cut from a media to be tested. The sample was mounted on a TEXTEST® FX 3310 (obtained from Textest AG, Schwerzenbach, Switzerland). Permeability through the media was measured using air, wherein cubic feet of air per square feet of media per minute (ft$^3$ air/ft$^2$ media/min) or cubic meters of air per square meters of media per minute (m$^3$ air/m$^2$ media/min) was measured at a pressure drop of 0.5 inches (1.27 cm) of water.

Preparation Methods

Example 1—UV Treatment

UV-treated media layers were made by exposing the downstream (wire side) surface of a substrate to UV radiation. The UV source was a low pressure mercury lamp (4 inch×4 inch Standard Mercury Grid Lamp, BHK, Inc., Ontario, Canada). The low pressure mercury lamp produces UV light at the following discrete wavelengths: 185 nm, 254 nm, 297 nm, 302 nm, 313 nm, 365 nm, and 366 nm. 4 inch×4 inch samples were exposed to the lamp for between 1 and 20 minutes. Samples shown in FIG. 2 were exposed to the lamp for 20 minutes; samples used for water drop sizing experiments were treated for 8 minutes. Samples were placed approximately 1 cm below the lamp during treatment.

A sample of each substrate listed in Table 1 was UV treated with the low pressure mercury lamp in the presence of atmospheric oxygen. Using the same batch of fuel, D10, D50, and D90 for each substrate before and after treatment were measured; results are shown in Table 2. The contact angles and roll-off angles (for 20 μL drops and 50 μL drops) of each substrate (in toluene) before and after treatment are shown in Table 3.

UV-oxygen treatment with the low pressure mercury lamp resulted in substrates exhibiting an increased roll off angle compared to untreated substrate. As shown in Table 2, with the exception of Substrate 6, an enhancement of D50 mean droplet size of at least 2 fold was also observed. Higher roll off angles measured using drops of water deposited on a substrate sample submersed in toluene (Table 3) correlate with the coalescence of larger droplets by the substrate (D50 enhancement) in diesel fuel (Tables 2 and 3). Because the roll off angle correlates with the size of droplets that coalesce on a surface of a substrate, the roll off angle may be used to identify a substrate that has the ability to coalesce larger droplets capable of exiting the fuel stream.

Without wishing to be bound by theory, it is believed that the acrylic-based resin system of Substrate 6 does not allow for necessary modification(s) of the surface during exposure to UV irradiation. Given the ability of UV-oxygen treatment to enhance adhesion and droplet growth in 100% polyester and phenolic resin containing medias (Substrate 7 and Substrates 1-5, respectively), it is believed that an aromatic component or another form of carbon-carbon bond unsaturation can enhance the effect of UV-oxygen treatment of substrates.

In contrast, when the low pressure mercury lamp was fitted with either a UV bandpass filter (FSQ-UGS, Newport Corp., Irving, Calif.) that blocks wavelengths less than approximately 220 nm and greater than approximately 400 nm, treated Substrate 1 showed little to no change in roll-off angle or mean droplet size compared to untreated media.

Similarly, when Substrates 1 and 7 were treated with a lamp that emits UV at wavelengths greater than 360 nm (Model F300S, Heraeus Noblelight Fusion UV Inc., Gaithersburg, Md.), the treated substrates showed little to no change in mean droplet size compared to untreated substrates and only a small increase in roll off angle compared to untreated substrates.

TABLE 1

| | Composition |
|---|---|
| Substrate 1 | 80% Cellulose 20% Polyester; Phenolic Resin |
| Substrate 2 | 80% Cellulose 20% Polyester; Phenolic Resin with Silicone |
| Substrate 3 | 92% Cellulose 8% Glass; Phenolic Resin |
| Substrate 4 | 100% Cellulose; Phenolic Resin with Silicone |
| Substrate 5 | 90% Cellulose 10% Polyester; Phenolic Resin |
| Substrate 6 | 100% Cellulose; Acrylic Resin |
| Substrate 7 | 100% Polyester (PET) Meltblown; No Resin |
| Substrate 8 | 100% Polyamide (Nylon 6,6) Spunbound; No Resin |

TABLE 2

|  |  | Unmodified | UV Exposed | Enhancement |
|---|---|---|---|---|
| Substrate 1 | D90 (mm) | 0.60 | 1.49 | 2.5x |
|  | D50 (mm) | 0.38 | 0.81 | 2.1x |
|  | D10 (mm) | 0.18 | 0.19 | 1.1x |
| Substrate 2 | D90 (mm) | 0.38 | 1.32 | 3.5x |
|  | D50 (mm) | 0.20 | 0.49 | 2.5x |
|  | D10 (mm) | 0.12 | 0.17 | 1.3x |
| Substrate 3 | D90 (mm) | 0.45 | 1.46 | 3.2x |
|  | D50 (mm) | 0.22 | 1.06 | 4.8x |
|  | D10 (mm) | 0.12 | 0.49 | 4.0x |
| Substrate 4 | D90 (mm) | 0.16 | 1.75 | 10.8x |
|  | D50 (mm) | 0.12 | 1.17 | 9.5x |
|  | D10 (mm) | 0.08 | 0.32 | 4.1x |
| Substrate 5 | D90 (mm) | 0.37 | 2.24 | 6.1x |
|  | D50 (mm) | 0.27 | 1.71 | 6.3x |
|  | D10 (mm) | 0.16 | 0.86 | 5.6x |
| Substrate 6 | D90 (mm) | 0.76 | 0.76 | 1.0x |
|  | D50 (mm) | 0.61 | 0.67 | 1.1x |
|  | D10 (mm) | 0.32 | 0.34 | 1.1x |
| Substrate 7 | D90 (mm) | 0.17 | 0.70 | 4.1x |
|  | D50 (mm) | 0.09 | 0.27 | 3.0x |
|  | D10 (mm) | 0.05 | 0.10 | 2.0x |
| Substrate 8 | D90 (mm) | 0.70 | 1.97 | 2.8x |
|  | D50 (mm) | 0.49 | 1.35 | 2.8x |
|  | D10 (mm) | 0.32 | 0.74 | 2.3x |

TABLE 3

|  | Contact Angle in Toluene | | 20 uL Roll Off Angle in Toluene | | 50 uL Roll Off Angle in Toluene | | D50 |
|---|---|---|---|---|---|---|---|
|  | Untreated | UV Exposed | Untreated | UV Exposed | Untreated | UV Exposed | Enhancement |
| Substrate 1 | 137 | 102 | 41 | 90 | 10 | 90 | 2.1 |
| Substrate 2 | 143 | 138 | 3 | 90 | 1 | 34 | 2.5 |
| Substrate 3 | 130 | 101 | 12 | 90 | 5 | 90 | 4.8 |
| Substrate 4 | 142 | 129 | 3 | 90 | 1 | 90 | 9.5 |
| Substrate 5 | 145 | 110 | 15 | 90 | 7 | 90 | 6.3 |
| Substrate 6 | 157 | 152 | 7 | 17 | 3 | 15 | 1.1 |
| Substrate 7 | 150 | 137 | 10 | 90 | 10 | 90 | 3.0 |
| Substrate 8 | — | — | — | — | — | — | 2.8 |

Figure 4:
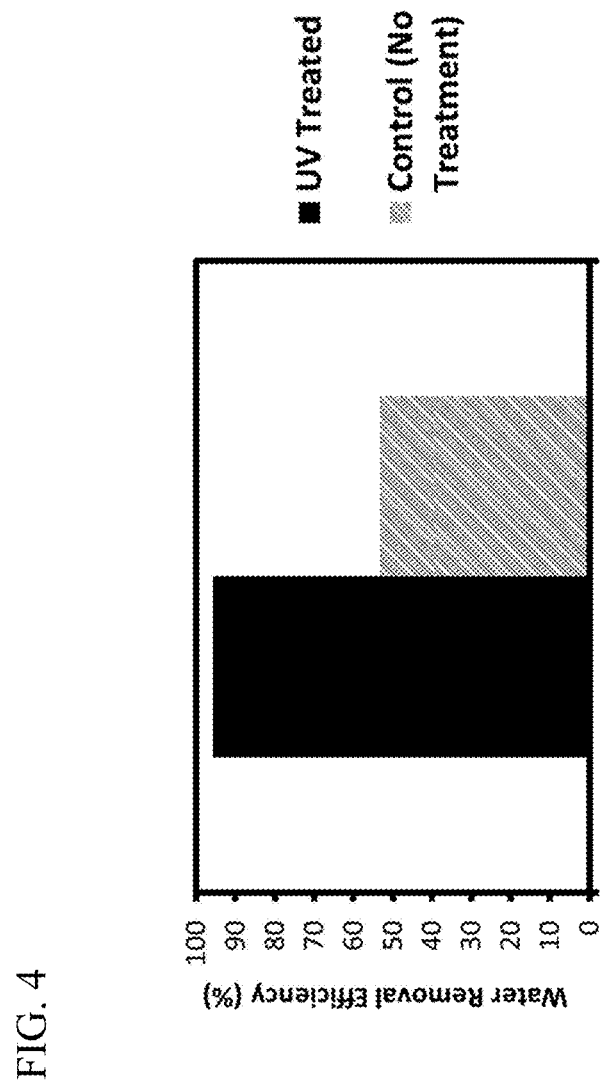
FIG. 4 shows performance of untreated Substrate 1 (control) and UV-oxygen-treated Substrate 1, as measured by water removal efficiency.

The ability of Substrate 1 samples (untreated and UV-oxygen-treated) to remove water from fuel (that is, the performance of the media) was determined by measuring downstream water content after 15 minutes; results are shown in FIG. 4. As can be seen in FIG. 4, compared to untreated Substrate 1, UV-oxygen-treated Substrate 1 samples exhibited significantly improved ability to remove water from the fuel and to maintain low downstream water content, consistent with the observed increased roll off angle and D50 enhancement compared to untreated substrate.

Figure 5:
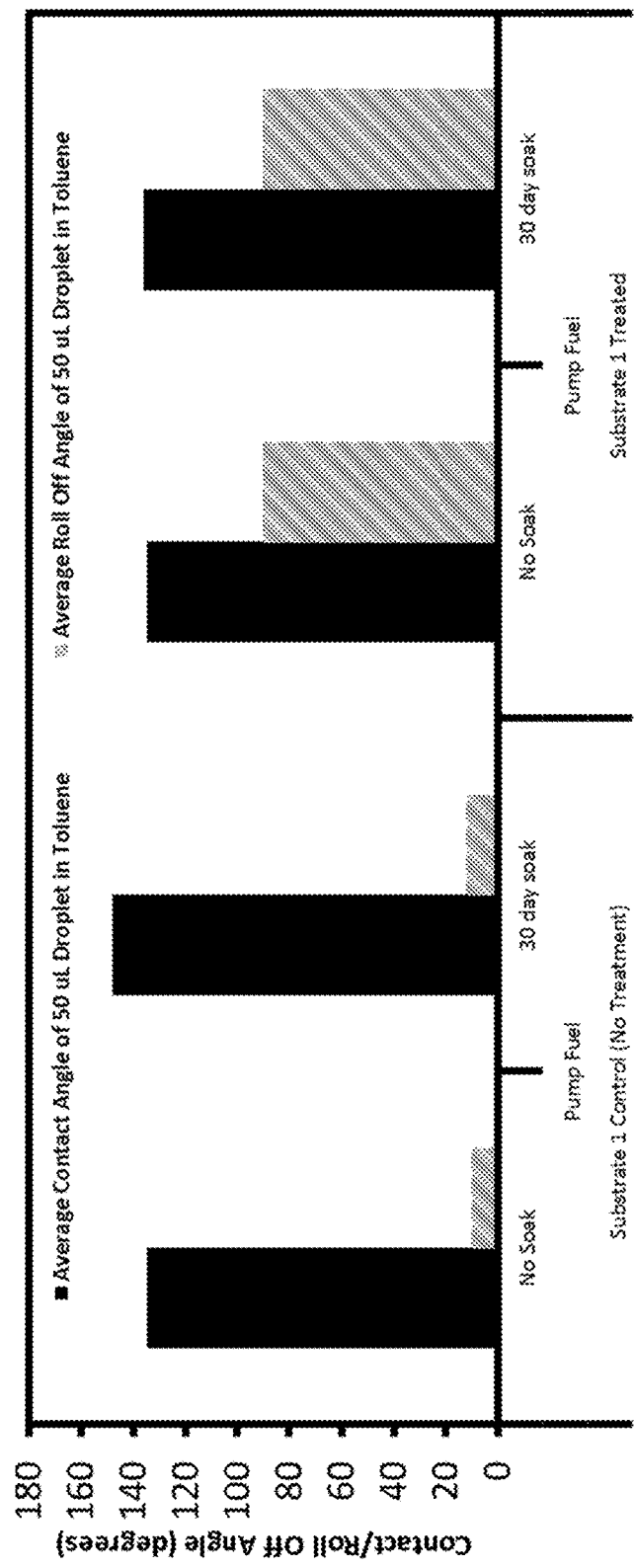
FIG. 5 shows the contact angle and the roll off angle of untreated Substrate 1 and UV-oxygen-treated Substrate 1 without soaking or after soaking in Pump Fuel for 30 days. Contact angles and roll off angles were measured using a 50 µL water droplet in toluene, and reported values are an average of three independent measurements taken on different areas of the media.

Substrate 1 samples (untreated and UV-oxygen-treated) were soaked in 200 milliliters (mL) of Pump Fuel for 30 days at 55° C. Before testing, control (not soaked) and treated samples were washed with hexane and then heated for five minutes in an 80° C. oven to evaporate the hexane. Contact angles in toluene and roll-off angles in toluene were measured using 50 μL drops of ultra-pure water deposited on a substrate sample that was submersed in toluene. Measurements were performed as described above. Results are shown in FIG. 5 and Table 4. The average roll off angle and contact angle—and the corresponding ability to remove water from fuel—were maintained in UV-oxygen-treated substrates even after being soaked in fuel for 30 days at 55° C., conditions that are found in some in-the-field applications and can accelerate aging of a substrate.

TABLE 4

|  |  | Treatment | | | | | | |
|---|---|---|---|---|---|---|---|---|
|  |  |  | UV-Treated | UV >300 nm | UV 254 nm Only | $H_2O_2$ + UV | Untreated Soaked 24 Hrs | UV Treated Soaked 24 hrs |
| Concentration |  |  | 0 nm | 8 min | 8 min | 8 min | 8 min | 0 min | 8 min |
| Droplet Sizing | D90 (mm) |  | 0.60 | 1.49 | 0.50 | 0.80 | 0.93 | 0.50 | 1.01 |
|  | D50 (mm) |  | 0.29 | 0.81 | 0.31 | 0.33 | 0.31 | 0.36 | 0.81 |
|  | D10 (mm) |  | 0.17 | 0.19 | 0.19 | 0.15 | 0.14 | 0.18 | 0.35 |

TABLE 4-continued

| | Treatment | | | | | |
|---|---|---|---|---|---|---|
| | UV-Treated | UV >300 nm | UV 254 nm Only | H$_2$O$_2$ + UV | Untreated Soaked 24 Hrs | UV Treated Soaked 24 hrs |
| | | | Time | | | |
| Concentration | 0 nm | 8 min | 8 min | 8 min | 0 min | 8 min |
| D90 Enhancement | 2.5x | 0.8x | 1.3x | 1.5x | 0.8x | 1.7x |
| D50 Enhancement | 2.8x | 1.1x | 1.1x | 1.1x | 1.2x | 3.6x |
| D10 Enhancement | 1.1x | 1.1x | 0.9x | 0.9x | 1.1x | 2.1x |
| Contact Angle in Toluene | 137° | 102° | 132° | 137° | 141° | — | — |
| 20 uL Roll Off Angle in Toluene | 41° | 90° | — | 37° | — | — | — |
| 50 uL Roll Off Angle in Toluene | 10° | 90° | 31° | 23° | 47° | — | — |

Example 2—UV/H$_2$O$_2$ Treatment

Substrate 1 was cured by heating the media at 150° C. for 10 minutes. The substrate was then submerged in a 50% H$_2$O$_2$ solution contained in a shallow petri dish (1 cm deep) and UV treated with a low pressure mercury lamp (4 inch×4 inch Standard Mercury Grid Lamp, BHK, Inc., Ontario, Canada) for 0 minutes, 2 minutes, 4 minutes, 6 minutes, or 8 minutes. The substrate was then oven dried at 80° C. for 5 minutes.

Figure 6:
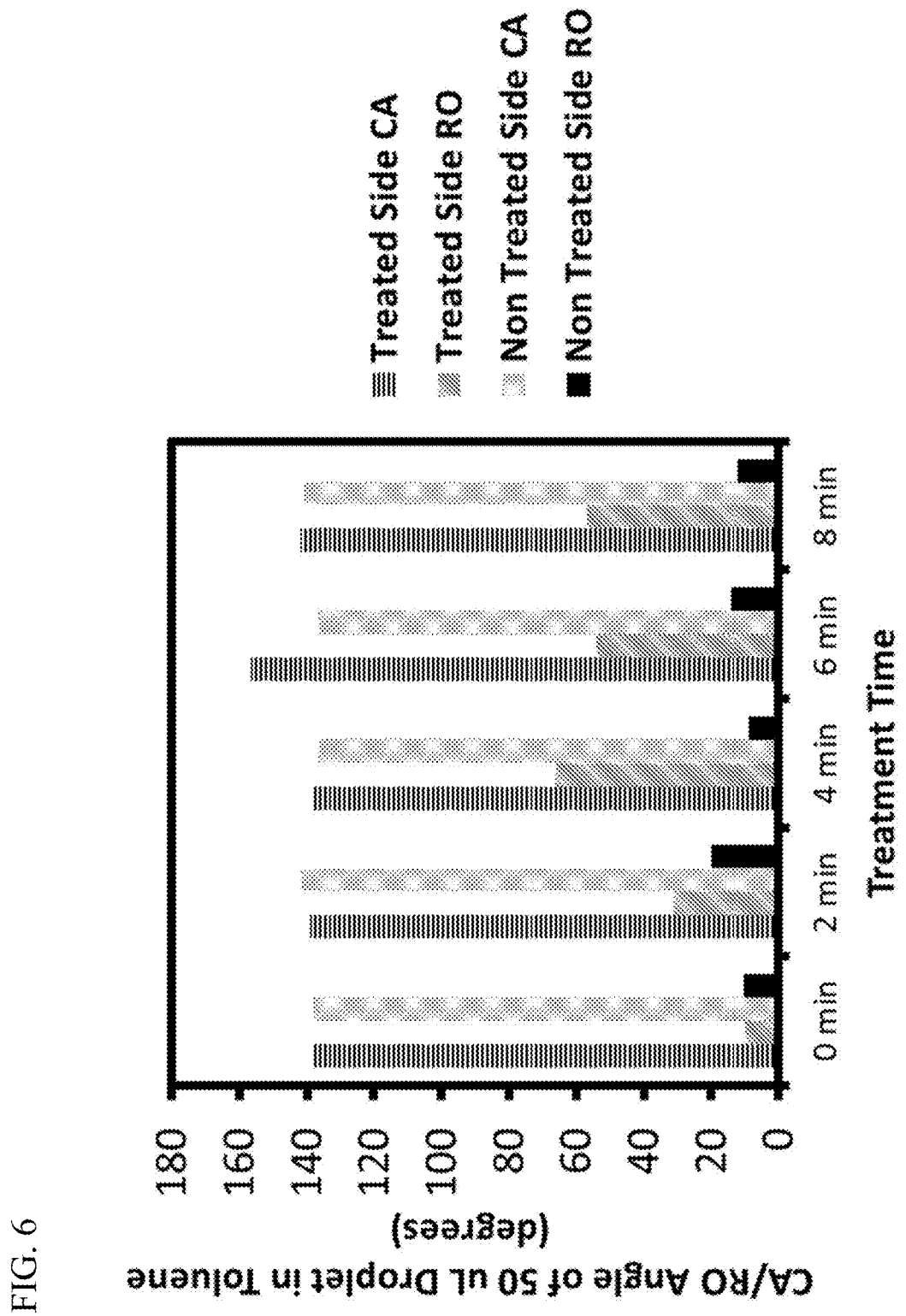
FIG. 6 shows the contact angle (CA) and roll off angle (RO) of a treated side and an untreated side of $UV/H_2O_2$-treated Substrate 1 immersed in toluene, measured using a 50 µL water droplet.
Figure 7:
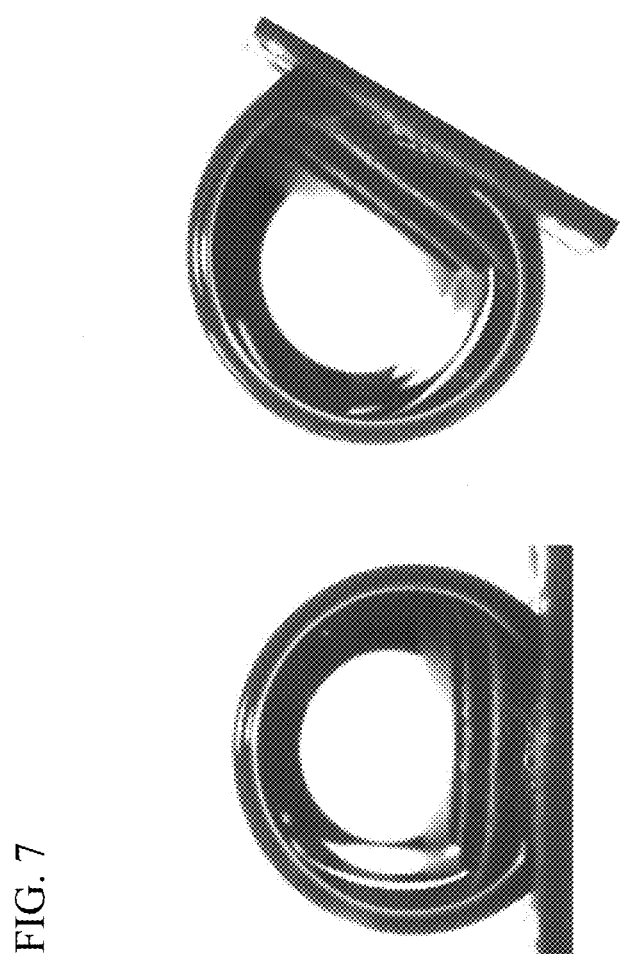
FIG. 7 shows exemplary images of a 20 µL water droplet on PHPM-treated Substrate 1 immersed in toluene at 0° rotation (left) and 60° rotation (right).

The contact angles (CA) in toluene and water roll-off angles (RO) of the treated side and the untreated side of each substrate were measured using 50 μL drops of ultra-pure water in toluene. Results are shown in Table 4 and FIG. 6.

Example 3—Comparative Examples

The contact angle and roll-off angle in toluene of a Cummins MO-608 fuel-water separation filter was tested using 20 μL water drops. The upstream side of the filter media had a contact angle of 143° and a roll-off angle of 19°. The downstream side of the filter media had a contact angle of 146° and a roll-off angle of 24°.

The contact angle and roll-off angle in toluene of an ACDelco TP3018 fuel-water separation filter was tested using 20 μL water drops. The upstream side of the filter media had a contact angle of 146° and a roll-off angle of 28°. The downstream side of the filter media had a reported roll-off angle of 1° (that is, drops rolled away during the deposition process).

The contact angle and roll-off angle in toluene of a Ford F150 FD4615 fuel-water separation filter was tested using 20 μL water drops. The upstream side of the filter media had a contact angle of 149° and a roll-off angle of 10°. The downstream side of the filter media had a contact angle of 137° and a roll-off angle of 9°.

The contact angle and roll-off angle in toluene of a Donaldson P551063 fuel-water separation filter was tested using 20 μL water drops. The upstream side of the filter media had a contact angle of 157° and a roll-off angle of 22°. The downstream side of the filter media had a contact angle of 125° and a roll-off angle of 11°.

The contact angle and roll-off angle in toluene of a polytetrafluoroethylene (PTFE) membrane was tested using 50 μL water drops. The membrane had a reported roll-off angle of 1° (that is, drops rolled away during the deposition process), making it was impossible to stabilize the droplet to measure a contact angle. It was approximated that the contact angle is at least 165°.

The contact angle and roll-off angle in toluene of a Komatsu 600-319-5611 fuel filter was tested using 20 μL water drops. The upstream side of the filter media had a contact angle of 150° and a roll-off angle of 3°. The downstream side of the filter media had a contact angle of 145° and a roll-off angle of 32°.

Example 4—Polymer Coating by Dip Coating

Substrate 1 (20% polyester/80% cellulose media with a partially-cured phenolic resin component) was coated with a polymer, using the polymers, concentrations, and solvents shown in Table 5. Samples were dip coated using a Chemat DipMaster 50 dip coater (Chemat Technology, Inc., Northridge, Calif.). Media was fully submerged in a solution including polymer and withdrawn at a rate of 50 mm/min. To ensure coating homogeneity, media was dip coated, rotated 180 degrees, and dip coated again (for a total of two dip coats). Non-aqueous solvents were removed via oven drying at 80° C. for 5 minutes, and water was removed via oven drying at 100° C. for 5 minutes.

To create a charged coating (via quaternization) of PEI-600 (see Table 5 (PEI-600 HCl)), Substrate 1 that had been previously coated with PEI-600 was dip coated in HCl (0.05 M in IPA), using the dip coating procedures described above. To create PEI-10K+Maleic Anhydride coating (see Table 5), Substrate 1 that had been previously coated with PEI-10K was dip coated in maleic anhydride using the dip coating procedures described above.

After the dip coating procedure was complete, to increase rigidity of the media and cure the partially-cured phenolic resin, a curing treatment was applied at 150° C. for 10 minutes after drying at 80° C. for 5 minutes.

Figure 8:
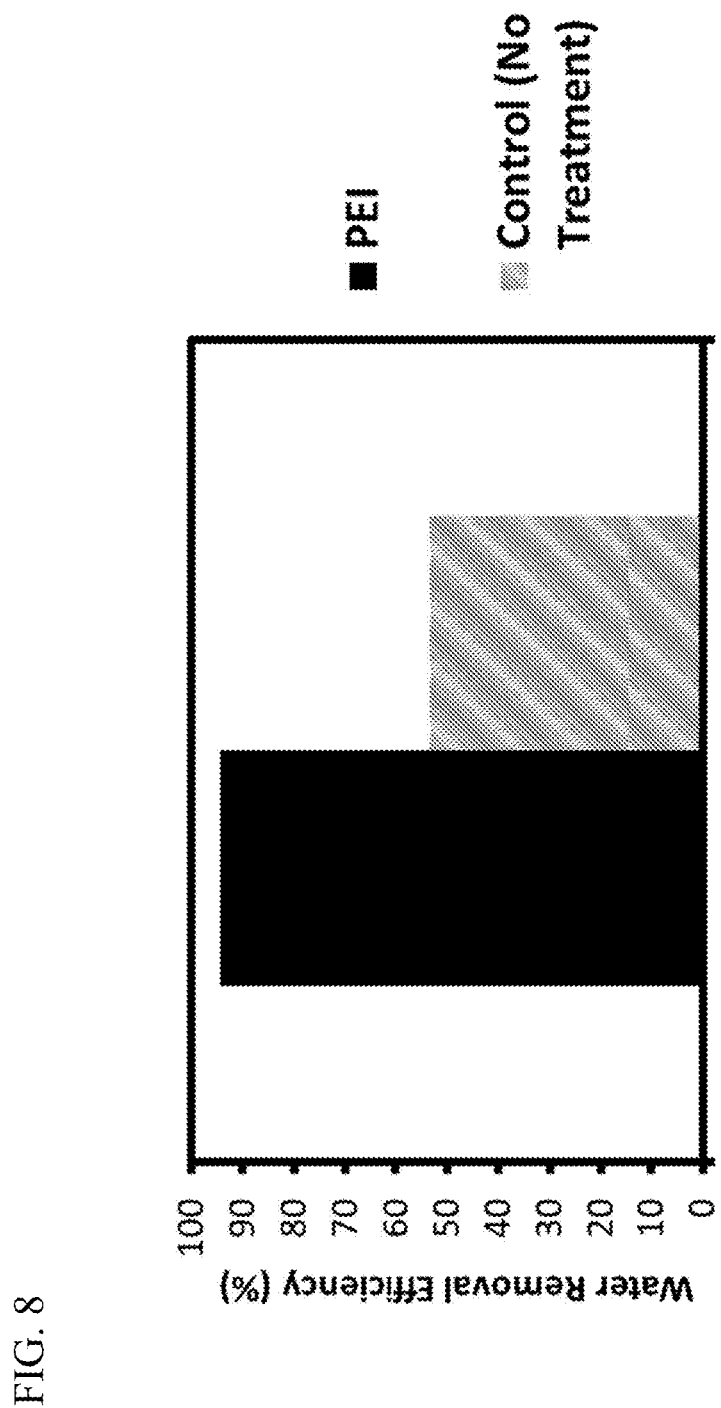
FIG. 8 shows the performance as measured by water removal efficiency of uncoated (control) and PEI-10K-coated Substrate 1.

Results are shown in Table 5 and FIG. 8. An exemplary image of a 20 μL water droplet on a PHPM-treated substrate (see Table 5) immersed in toluene at 0° rotation (left) and 60° rotation (right) is shown in FIG. 2.

As shown in Table 4, higher roll off angles measured using drops of water deposited on a substrate sample submersed in toluene correlate with the coalescence of larger droplets by the substrate (D50 enhancement) in diesel fuel. Because the roll off angle correlates with the size of droplets that coalesce on a surface of a substrate, the roll off angle may be used to identify a substrate that has the ability to coalesce larger droplets capable of exiting the fuel stream. As shown in FIG. 8, increased fuel-water separation efficiency was seen for PEI-10K coated substrate compared to untreated substrate, consistent with the observed increased roll off angle and D50 enhancement.

TABLE 5

| | | Polymer | | |
|---|---|---|---|---|
| | | PEI-10K | PS-co-AA | PHPM |
| | | | Concentration | |
| | | 1 g/200 mL | 1 g/200 mL | 1 g/200 mL |
| | | | Solvent | |
| | | IPA | IPA | MeOH |
| | | | Dry Time (at 80° C.) | |
| | untreated | 5 | 5 | 5 |
| Droplet Sizing | | | | |
| D90 (mm) | 0.60 | 1.00 | 0.43 | 2.02 |
| D50 (mm) | 0.29 | 0.69 | 0.30 | 1.09 |
| D10 (mm) | 0.17 | 0.29 | 0.20 | 0.65 |
| D90 Enhancement | | 1.7x | 0.7x | 3.4x |
| D50 Enhancement | | 2.4x | 1.0x | 3.8x |
| D10 Enhancement | | 1.7x | 1.2x | 3.9x |
| Contact Angle in Toluene | 137° | 138° | 134° | 125° |
| 20 uL Roll Off Angle in Toluene | 41° | 68° | 8° | 90° |
| 50 uL Roll Off Angle in Toluene | 10° | 18° | — | 90° |

| | Polymer | | | |
|---|---|---|---|---|
| | PAA | PEI-600 | PEI-600 HCl | PEI-10K + Maleic Anhydride |
| | | | Concentration | |
| | 1 g/200 mL | 1 g/200 mL | 1 g/200 mL | 1 g/200 mL |
| | | | Solvent | |
| | IPA | IPA | IPA | IPA |
| | | | Dry Time (at 80° C.) | |
| | 5 | 5 | 5 | 5 |
| Droplet Sizing | | | | |
| D90 (mm) | 0.43 | 0.55 | 0.87 | |
| D50 (mm) | 0.29 | 0.35 | 0.52 | 0.50 |
| D10 (mm) | 0.15 | 0.18 | 0.35 | 0.30 |
| D90 Enhancement | 0.7x | 0.9x | 1.5x | 0.16 |
| D50 Enhancement | 1.0x | 1.2x | 1.8x | 0.8x |
| D10 Enhancement | 0.9x | 1.1x | 2.1x | 1.0x |
| | | | | 1.0x |
| Contact Angle in Toluene | 135° | 127° | 131° | 144° |
| 20 uL Roll Off Angle in Toluene | 34° | 37° | 90° | 34° |
| 50 uL Roll Off Angle in Toluene | — | 11° | 21° | — |
| | | | | — |

| | Polymer | | | | |
|---|---|---|---|---|---|
| | PHEM | P2E2O | DAMO-T | Tyzor | SIVO 203 |
| | | | Concentration | | |
| | 1 g/200 mL | 1 g/200 mL | 2 g/200 mL | 10 mL/200 mL | 4 g/400 mL |
| | | | Solvent | | |
| | IPA | MeOH | EtOH | Hexane | IPA |
| | | | Dry Time (at 80° C.) | | |
| | 5 | 5 | 5 | 15 | 15 |
| Droplet Sizing | | | | | |
| D90 (mm) | 0.65 | 1.33 | 0.44 | 0.41 | 0.31 |
| D50 (mm) | 0.42 | 0.68 | 0.27 | 0.25 | 0.19 |
| D10 (mm) | 0.28 | 0.34 | 0.14 | 0.15 | 0.12 |
| D90 Enhancement | 1.1x | 2.2x | 0.7x | 0.7x | 0.5x |
| D50 Enhancement | 1.5x | 2.4x | 0.9x | 0.9x | 0.7x |

TABLE 5-continued

|  |  |  |  |  |  |
|---|---|---|---|---|---|
| D10 Enhancement | 1.7x | 2.1x | 0.9x | 0.9x | 0.7x |
| Contact Angle in Toluene | 139° | 125° | 136° | 132° | 133° |
| 20 uL Roll Off Angle in Toluene | 56° | 90° | <60° | 28° | 17° |
| 50 uL Roll Off Angle in Toluene | 16° | 90° | — | — | — |

Example 5—Effect of Polymer Coating on Permeability

Substrate 1 (20% polyester/80% cellulose media with a partially-cured phenolic resin component) was dip coated using a Chemat DipMaster 50 dip coater (Chemat Technology, Inc., Northridge, Calif.) with 2% (w/v) PHEM, 4% (w/v) PHEM, 6% (w/v) PHEM, or 8% (w/v) PHEM in methanol. Media was fully submerged in the solution including polymer and withdrawn at a rate of 50 mm/min. To ensure coating homogeneity, media was dip coated, rotated 180 degrees, and dip coated again (for a total of two dip coats). Non-aqueous solvents were removed via oven drying at 80° C. for 5 minutes, and water was removed via oven drying at 100° C. for 5 minutes.

After the dip coating procedure was complete and after drying at 80° C. for 5 minutes, a curing treatment was applied at 150° C. for 10 minutes.

Figure 9:
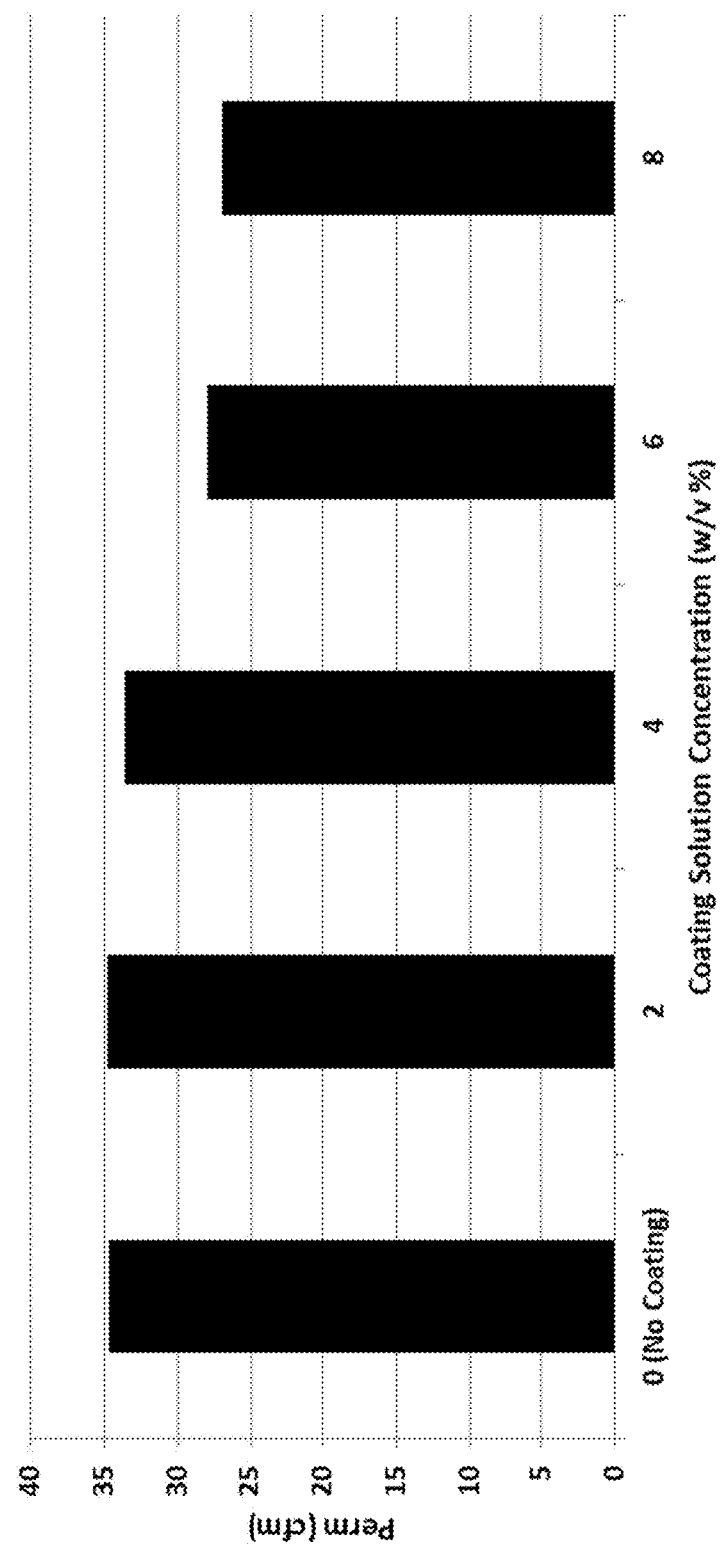
FIG. 9 shows the permeability of uncoated Substrate 1 and of Substrate 1 coated with 2% (w/v) PHEM, 4% (w/v) PHEM, 6% (w/v) PHEM, or 8% (w/v) PHEM.

Permeability was tested as described above. Results are shown in FIG. 9.

Example 6—Polymer Coating by Dip Coating, Crosslinking, and Annealing

Substrate 1 (20% polyester/80% cellulose media with a partially-cured phenolic resin component; see Table 1) was coated with a polymer, using the polymers, crosslinkers, concentrations, and solvents shown in Tables 6 and 7. Samples were dip coated using a Chemat DipMaster 50 dip coater (Chemat Technology, Inc., Northridge, Calif.). Media was fully submerged in a solution including polymer and withdrawn at a rate of 50 mm/min. To ensure coating homogeneity, media was dip coated, rotated 180 degrees, and dip coated again (for a total of two dip coats). Non-aqueous solvents were removed via oven drying at 80° C. for 5 minutes, and water was removed via oven drying at 100° C. for 5 minutes.

After dip coating and/or before annealing, if performed, the media was oven dried at 80° C. for 5 minutes and then exposed to 150° C. for 5 minutes. The heating is believed to increase rigidity of the media, to cure the partially-cured phenolic resin, and to accelerate crosslinking of the crosslinker, if present.

If the polymer coating was annealed, after the dip coating procedure and heating were complete, the media was submerging in hot (90° C.) water for 1-2 minutes. After annealing, the media was oven dried for 100° C. for 5 minutes.

Figure 10:
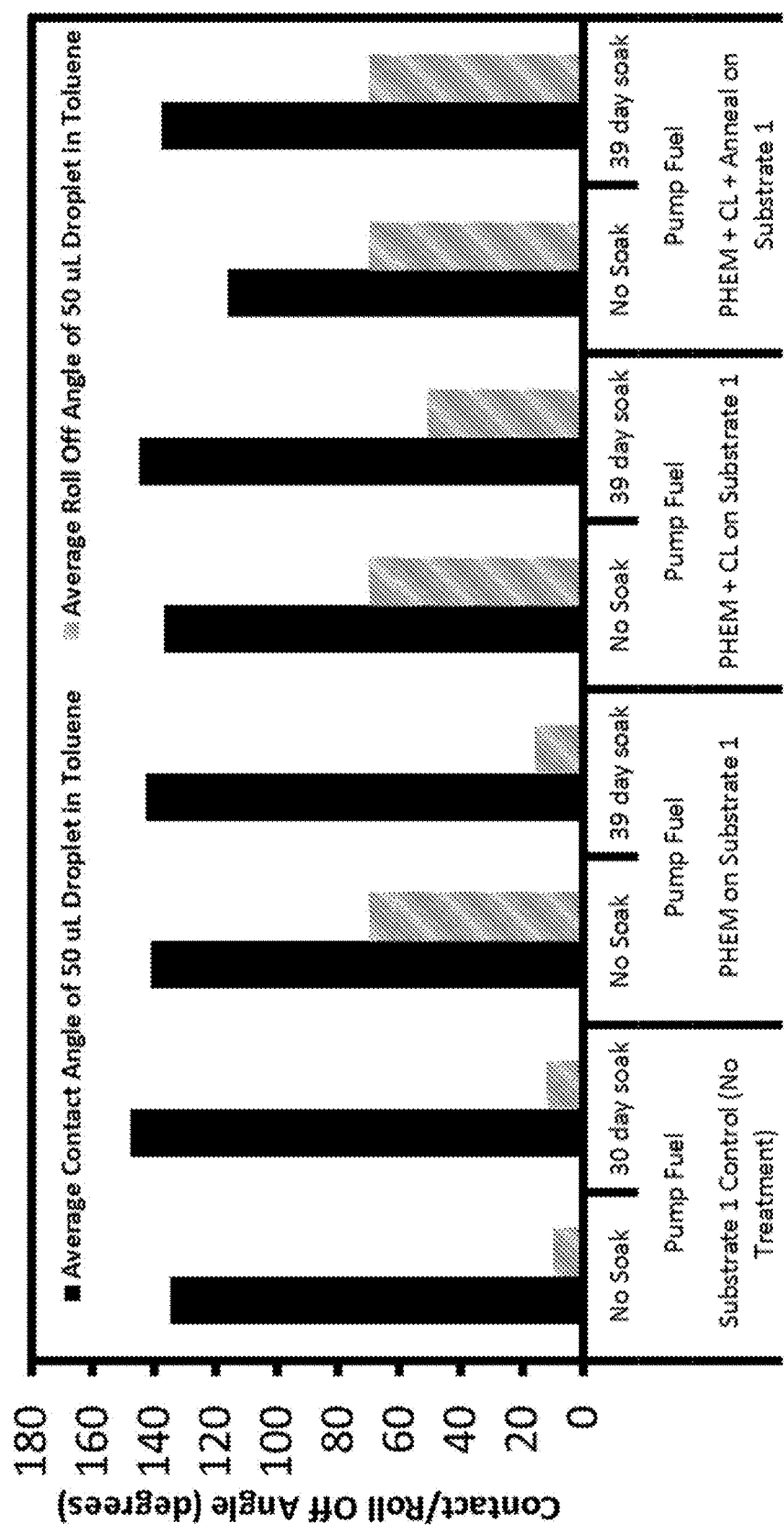
FIG. 10 shows the contact angle and the roll off angle of a 50 µL water droplet on uncoated Substrate 1 (control), PHPM-coated Substrate 1, PHPM-coated Substrate 1 crosslinked (CL) using 1% (w/v) N-(2-Aminoethyl)-3-aminopropyltrimethoxysilane, and PHPM-coated Substrate 1 crosslinked (CL) using 1% (w/v) N-(2-Aminoethyl)-3-aminopropyltrimethoxysilane and annealed without soaking or after soaking in Pump Fuel for the indicated period.
Figure 11:
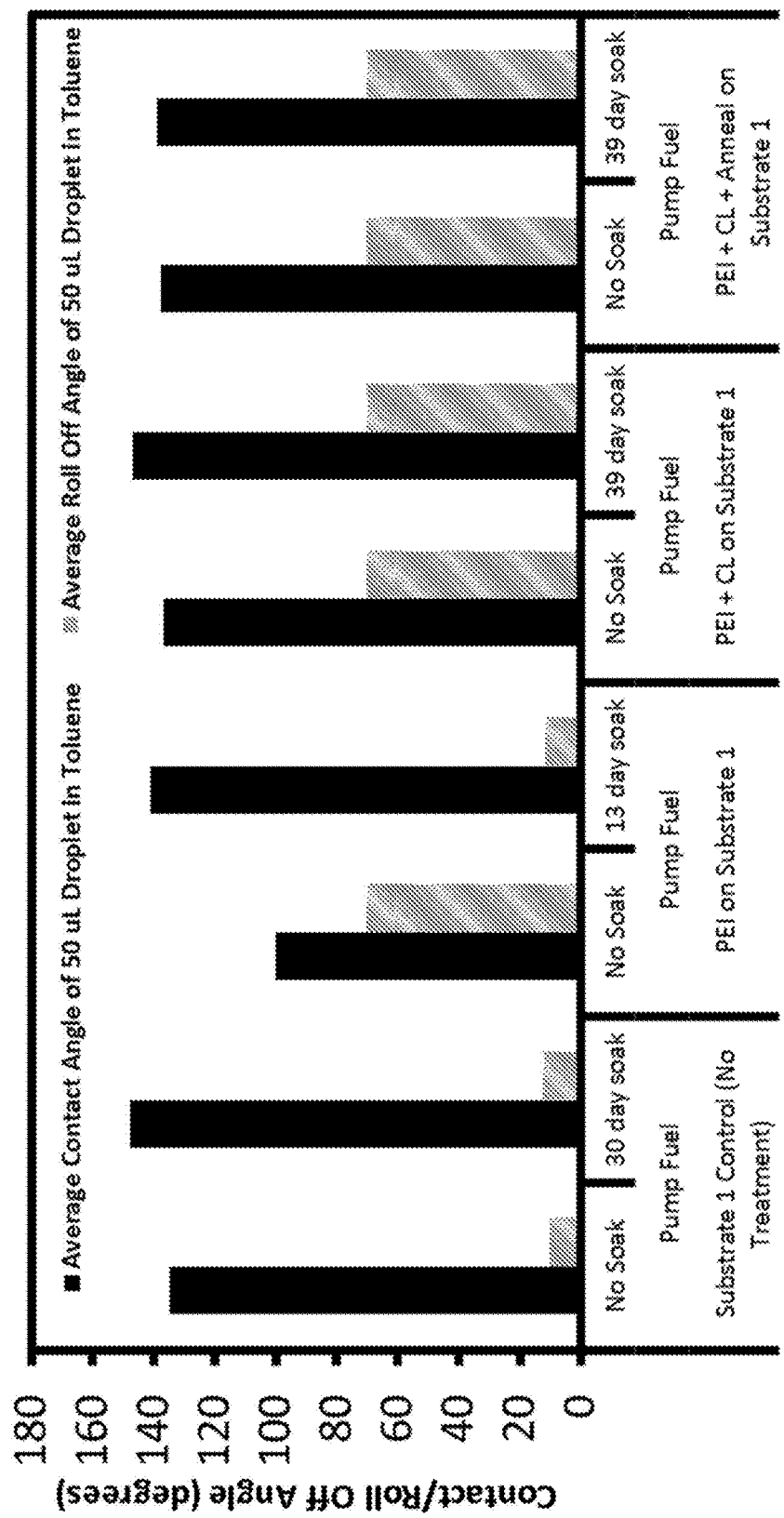
FIG. 11 shows the contact angle and the roll off angle of a 50 µL water droplet on uncoated Substrate 1 (control), PEI-10K-coated Substrate 1, PEI-10K-coated Substrate 1 crosslinked (CL) using 1% (w/v) (3-glycidyloxypropyl) trimethoxysilane), and PEI-10K-coated Substrate 1 crosslinked (CL) using 1% (w/v) (3-glycidyloxypropyl) trimethoxysilane and annealed without soaking or after soaking in Pump Fuel for the indicated period.

Substrate 1 samples (untreated and polymer coated) were soaked in 200 milliliters (mL) of Pump Fuel for 13 days, 30 days, or 39 days (as indicated in FIG. 10 or FIG. 11) at 55° C. Before testing, control (not soaked) and treated samples were washed with hexane and then heated for five minutes in an 80° C. oven to evaporate the hexane. Contact angles in toluene and roll-off angles in toluene were measured using 50 µL drops of ultra-pure water deposited on a substrate sample that was submersed in toluene. Measurements were performed as described above.

Results are shown in FIG. 10 and FIG. 11. The average roll off angle and contact angle—and the corresponding ability to remove water from fuel—were maintained in crosslinked polymer-coated substrates and crosslinked and annealed polymer-coated substrates even after being soaked in fuel for 39 days at 55° C., conditions that are found in some in-the-field applications and can accelerate aging of a substrate.

TABLE 6

| Polymer | PEI-10K | PEI-10K |
|---|---|---|
| Polymer Concentration | 4 g/100 mL | 4 g/100 mL |
| Solvent | methanol | methanol |
| Crosslinker | none | 3-glycidyloxypropyl)trimethoxysilane |
| Crosslinker Concentration |  | 1 g/100 mL |
| Dry Time (at 80° C.) | 5 | 5 |

TABLE 7

| Polymer | PHEM | PHEM |
|---|---|---|
| Polymer Concentration | 4 g/100 mL | 4 g/100 mL |
| Solvent | methanol | methanol |
| Crosslinker | none | N-(2-Aminoethyl)-3-aminopropyltrimethoxysilane |
| Crosslinker Concentration |  | 1 g/100 mL |
| Dry Time (at 80° C.) | 5 | 5 |

Example 7—Polymer Coating by Electrospinning

A coating was formed on Substrate 6 (see Table 1) by electrospinning with a 10% polymer (w/v) solution using the conditions shown in Table 8. A methanol solution was used for poly(2-hydroxyethyl methacrylate) (PHEM) and an isopropyl alcohol (IPA) solution was used for PEI-10K. Coatings were formed with and without the presence of a crosslinker in the spinning solution. 0.5% (w/v) N-(2-Aminoethyl)-3-aminopropyltrimethoxysilane (also referred to herein as DAMO-T) was used as a crosslinker for PHEM; 0.5% (w/v) (3-glycidyloxypropyl) trimethoxy silane (also referred to herein as crosslinker 1) or 0.5% (w/v) poly (ethylene glycol) diacrylate (PEGDA) (also referred to herein as crosslinker 2) were used as the crosslinker for PEI-10K.

Figure 12:
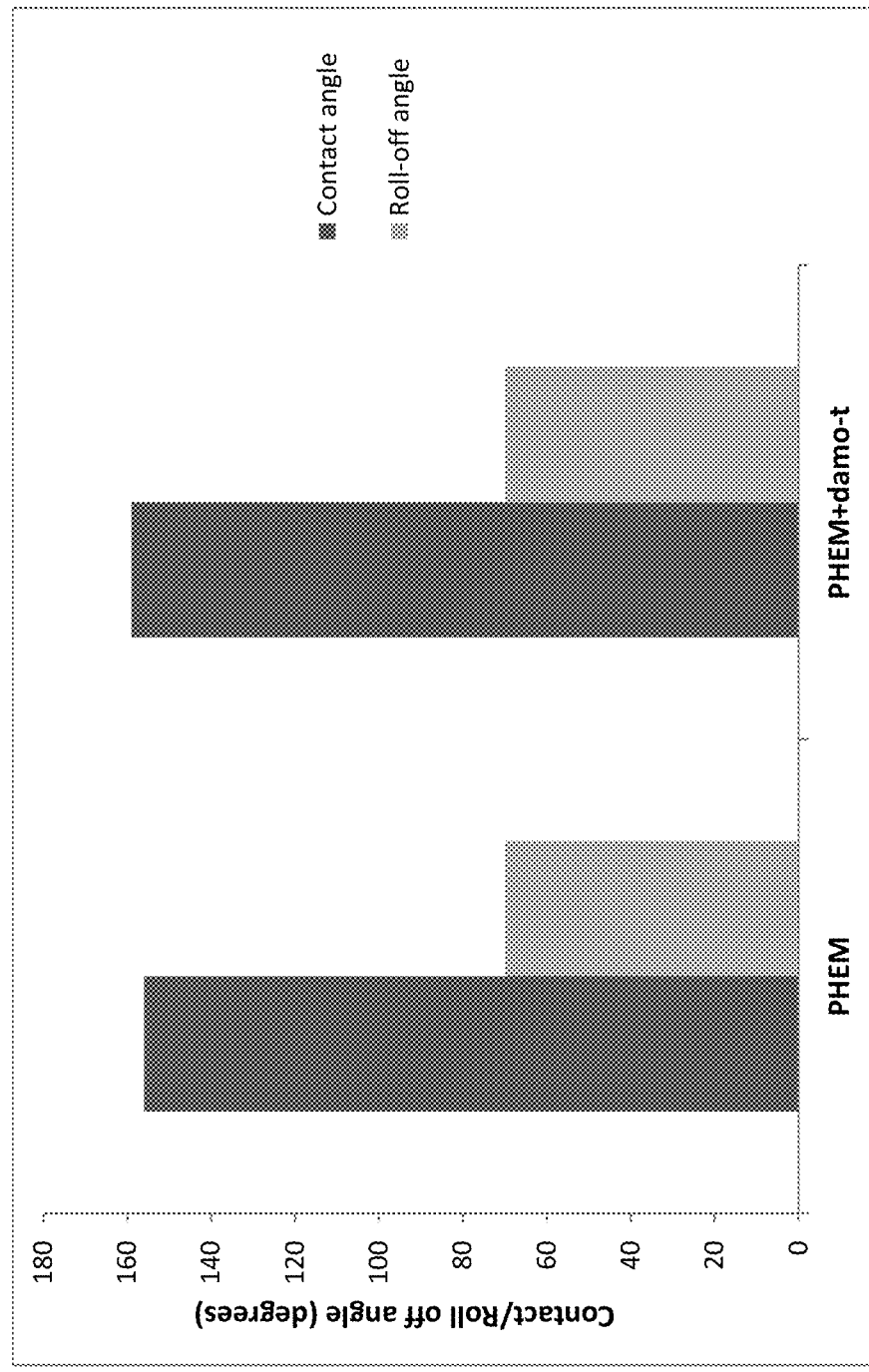
FIG. 12 shows the contact angle and the roll off angle of a 50 µL water droplet on an exemplary PHEM nanofiber-coated Substrate 6 with and without crosslinker DAMO-T.
Figure 13:
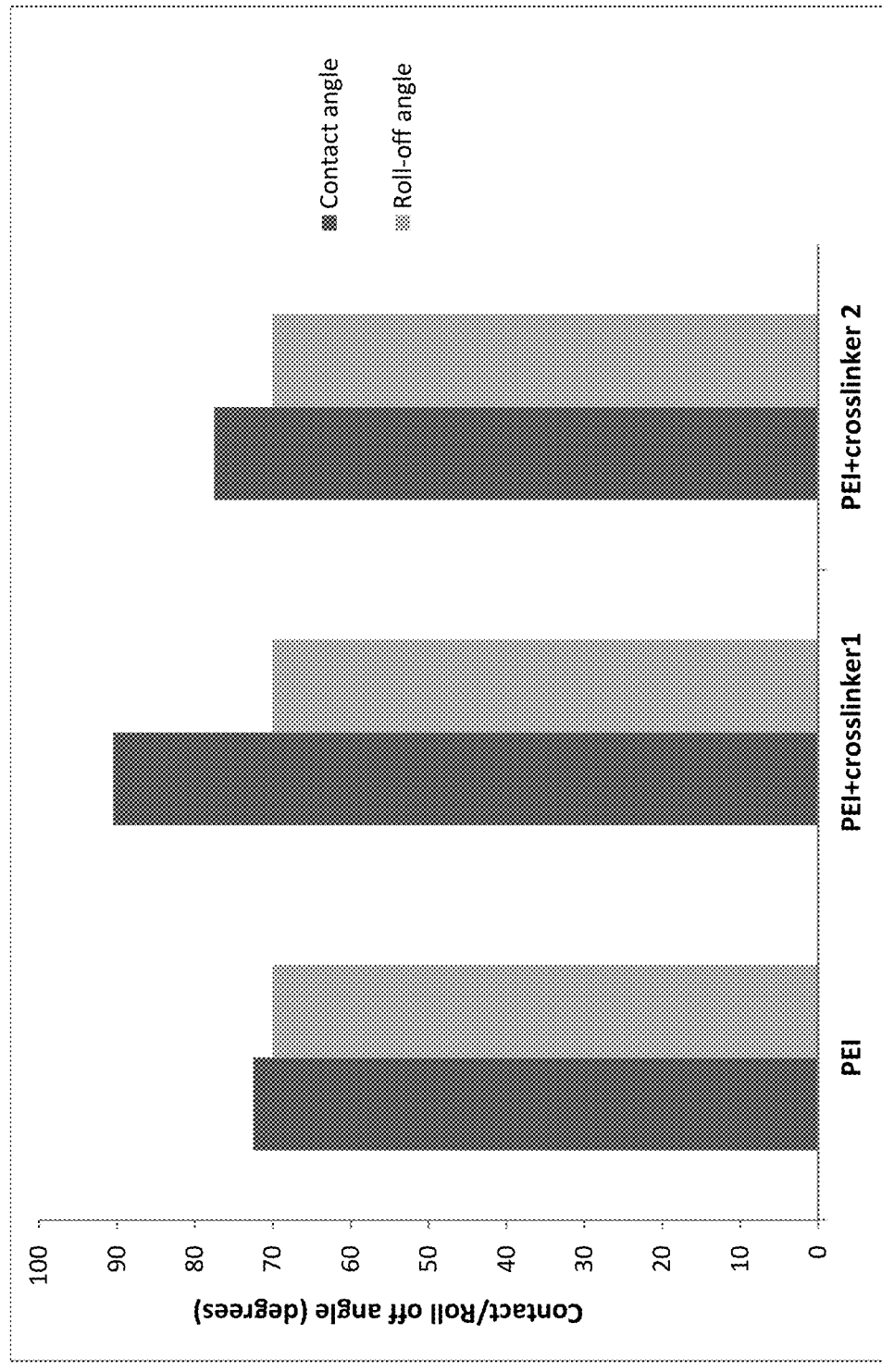
FIG. 13 shows the contact angle and the roll off angle of a 50 µL water droplet on an exemplary PEI nanofiber-coated Substrate 6 without crosslinker or crosslinked with (3-glycidyloxypropyl)trimethoxy silane) (crosslinker 1) or poly (ethylene glycol) diacrylate (crosslinker 2).

Results are shown in FIG. 12 to FIG. 15. Contact angles and roll off angles of a 50 µL water droplet on a PHEM-coated substrate with and without crosslinker were measured immediately after electrospinning and are shown in FIG. 12. Contact angles and roll off angles of a 50 µL water droplet on a PEI-coated substrate with and without crosslinker were measured immediately after electrospinning and are shown in FIG. 13.

Figure 14:
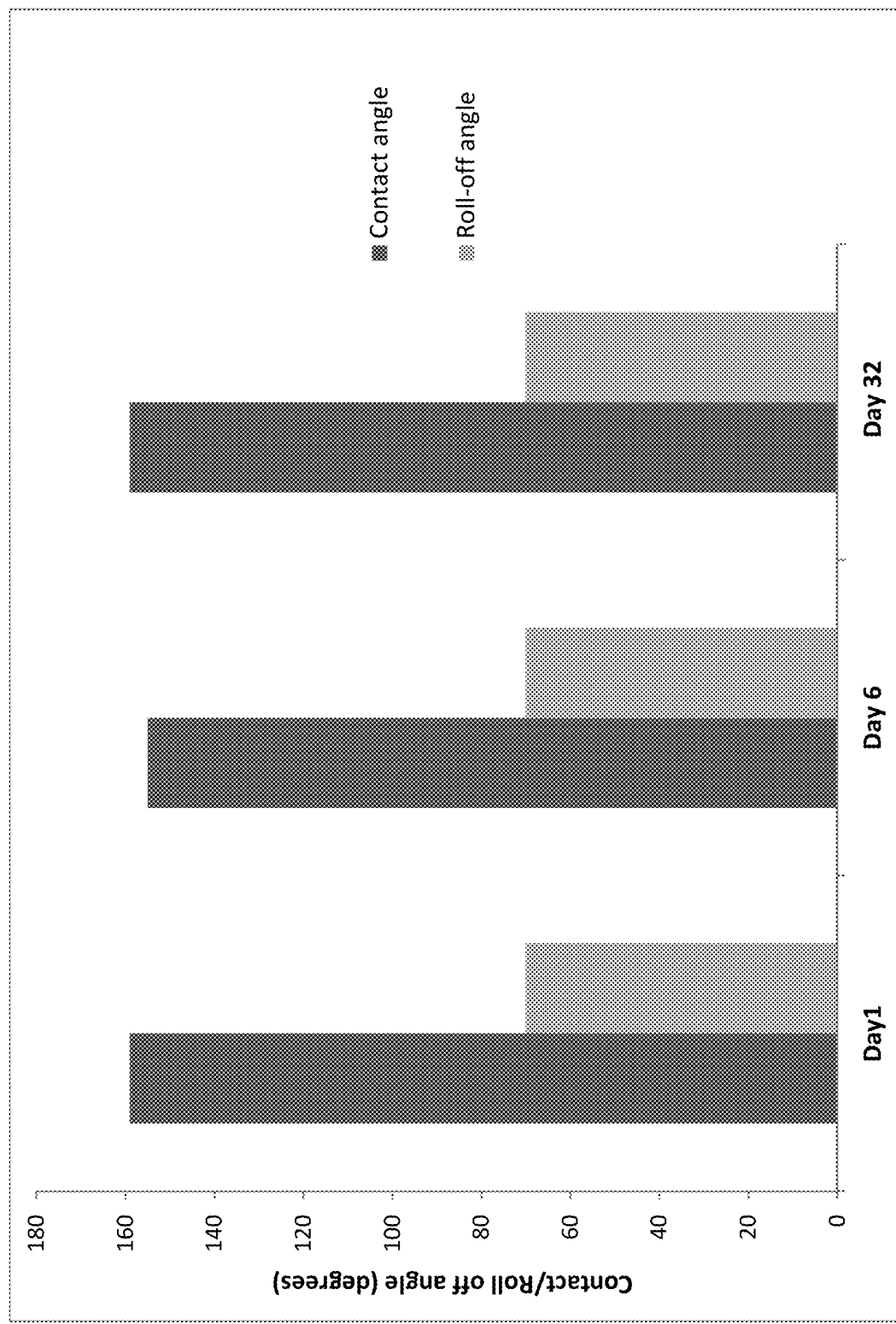
FIG. 14 shows the contact angles and the roll off angles of a 50 µL water droplet on an exemplary PHEM nanofiber-coated, DAMO-T-crosslinked Substrate 6 1 day, 6 days, and 32 days after formation of the coating by electrospinning.

FIG. 14 shows the contact angles and the roll off angles of a 50 μL water droplet on an exemplary PHEM nanofiber-coated, DAMO-T-crosslinked Substrate 6 1 day, 6 days, and 32 days after formation of the coating by electrospinning. Contact angles and roll off angles 52 days after formation of the coating by electrospinning were similar to those observed 32 days after formation of the coating by electrospinning.

Figure 15:
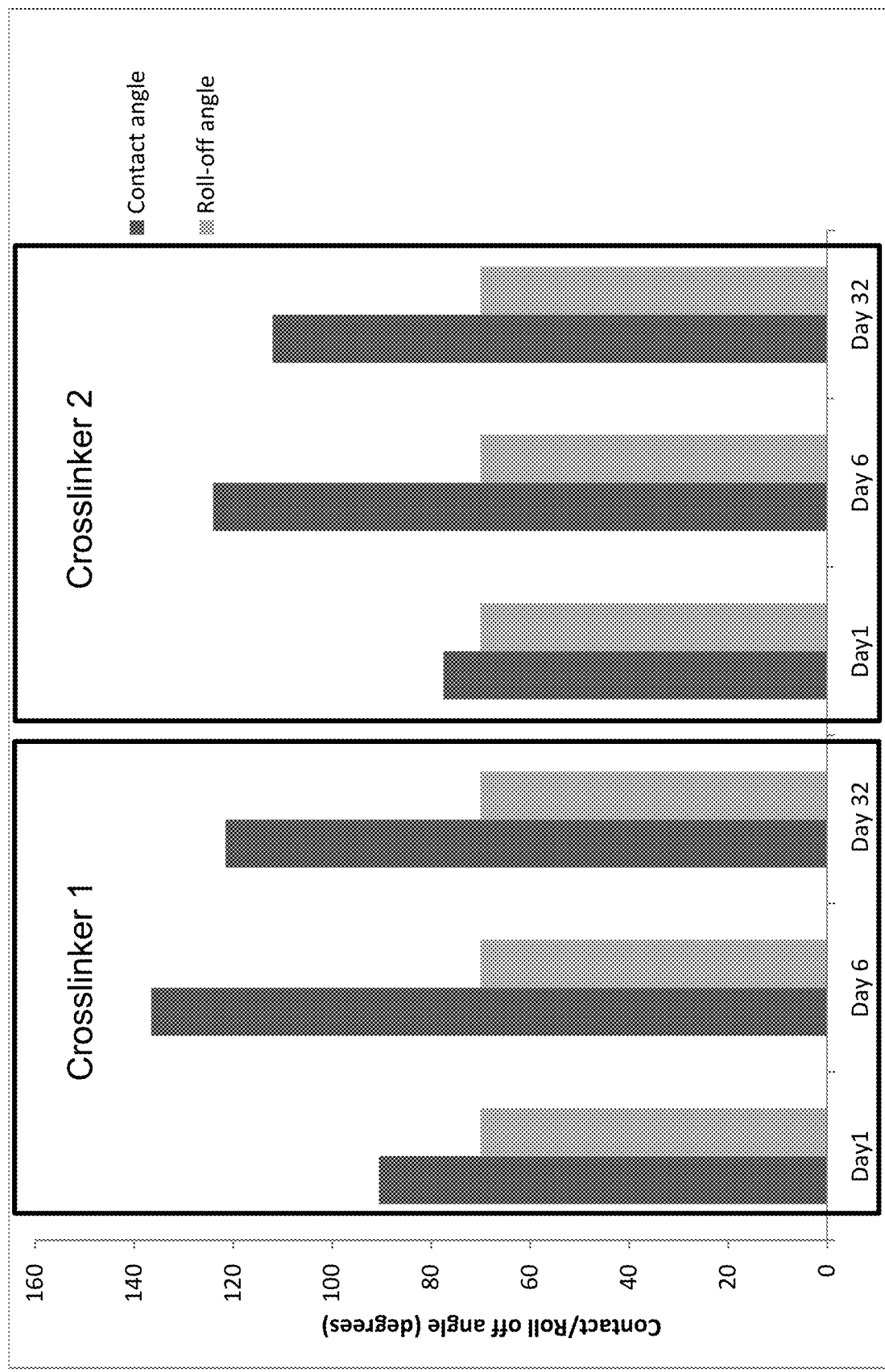
FIG. 15 shows the contact angle and the roll off angle of a 50 µL water droplet on an exemplary PEI-10K nanofiber-coated, crosslinked Substrate 6 1 day, 6 days, and 32 days after formation of the coating by electrospinning. The PEI was crosslinked using either (3-glycidyloxypropyl) trimethoxy silane (crosslinker 1) or poly (ethylene glycol) diacrylate (PEGDA) (crosslinker 2).

FIG. 15 shows the contact angles and the roll off angles of a 50 μL water droplet on an exemplary PEI-10K nanofiber-coated, crosslinked Substrate 6 1 day, 6 days, and 32 days after formation of the coating by electrospinning. The PEI was crosslinked using either (3-glycidyloxypropyl) trimethoxy silane (crosslinker 1) or poly (ethylene glycol) diacrylate (PEGDA) (crosslinker 2). Contact angles and roll off angles 52 days after formation of the coating by electrospinning were similar to those observed 32 days after formation of the coating by electrospinning.

Figure 16C:
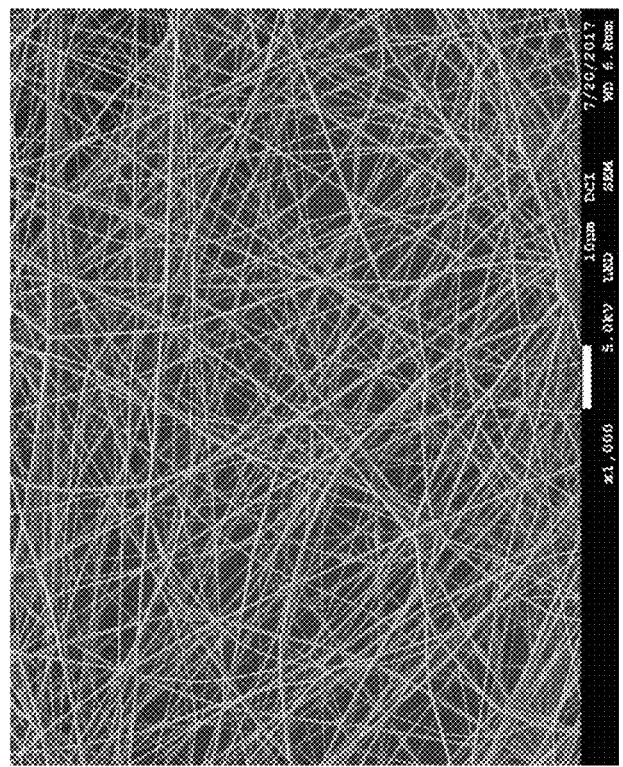
FIG. 16(A-C) shows exemplary scanning electron microscopy (SEM) images of uncoated Substrate 6 (FIG. 16A), Substrate 6 coated by electrospinning with PHEM without crosslinker (FIG. 16B), or Substrate 6 coated by electrospinning with PHEM with crosslinker DAMO-T (FIG. 16C). All images are shown at 1000× magnification.
Figure 16A:
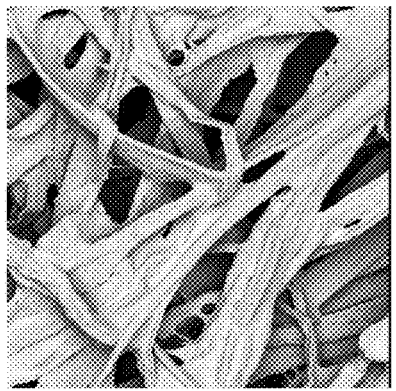
Figure 16B:
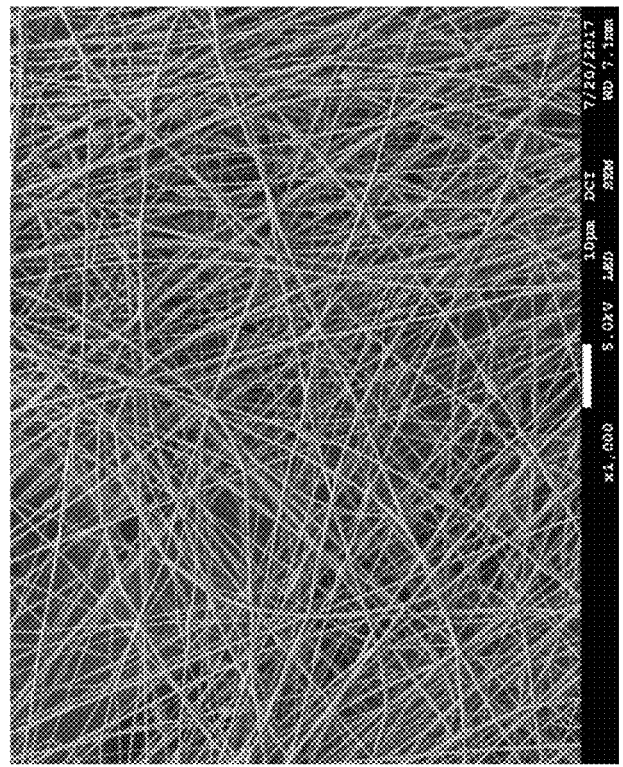
Figure 17B:
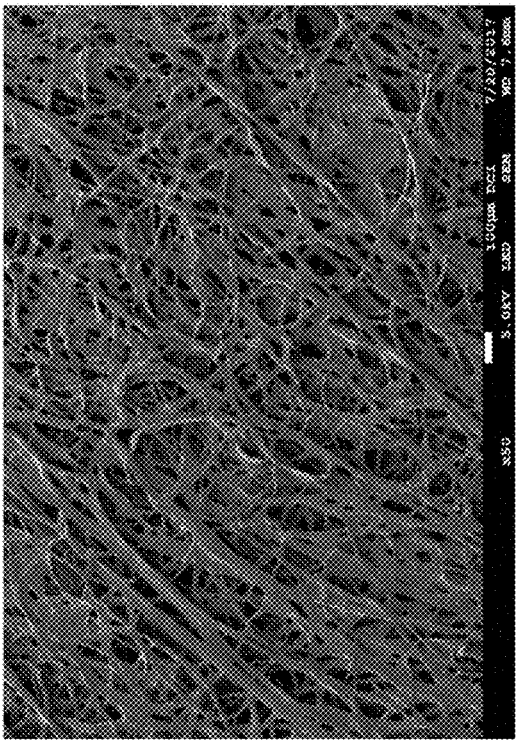
FIG. 17(A-C) shows exemplary SEM images of Substrate 6 coated by electrospinning with PEI-10K without crosslinker (FIG. 17A), Substrate 6 coated by electrospinning with PEI-10K with crosslinker (3-glycidyloxypropyl) trimethoxy silane (FIG. 17B), and Substrate 6 coated by electrospinning with PEI-10K with crosslinker poly (ethylene glycol) diacrylate (PEGDA) (FIG. 17C). All images are shown at 50× magnification.
Figure 17A:
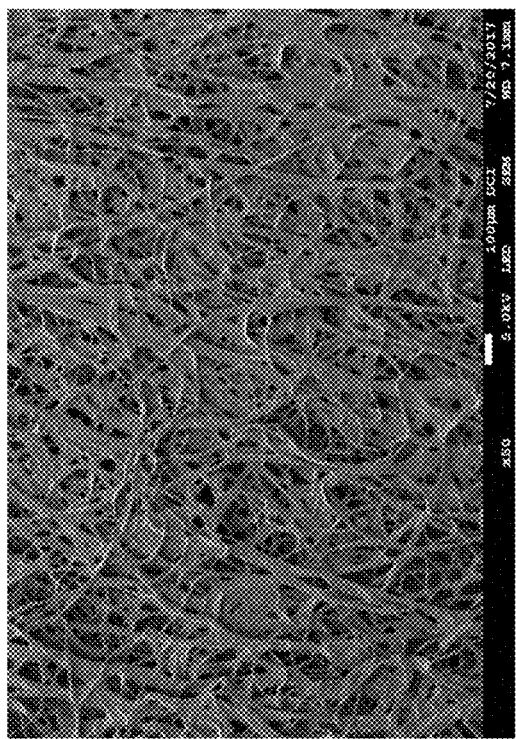
Figure 17C:
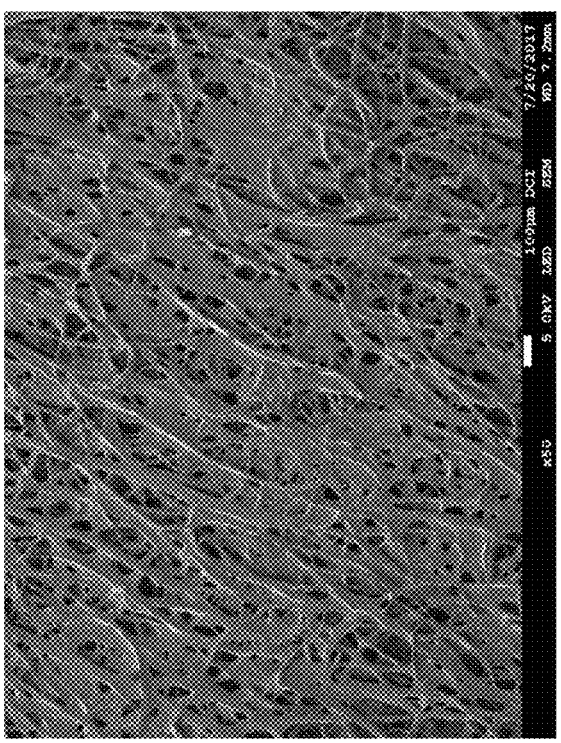
Figure 18A:
FIG. 18(A-D) shows exemplary SEM images of uncoated Substrate 6 (FIG. 18A); Substrate 6 coated by electrospinning with PEI-10K without crosslinker (FIG. 18B); Substrate 6 coated by electrospinning with PEI-10K and crosslinker 1 ((3-glycidyloxypropyl) trimethoxy silane) (FIG. 18C); and Substrate 6 coated by electrospinning with PEI-10K and crosslinker 2 (poly (ethylene glycol) diacrylate (PEGDA)) (FIG. 18D). All images are shown at 200× magnification.
Figure 18B:
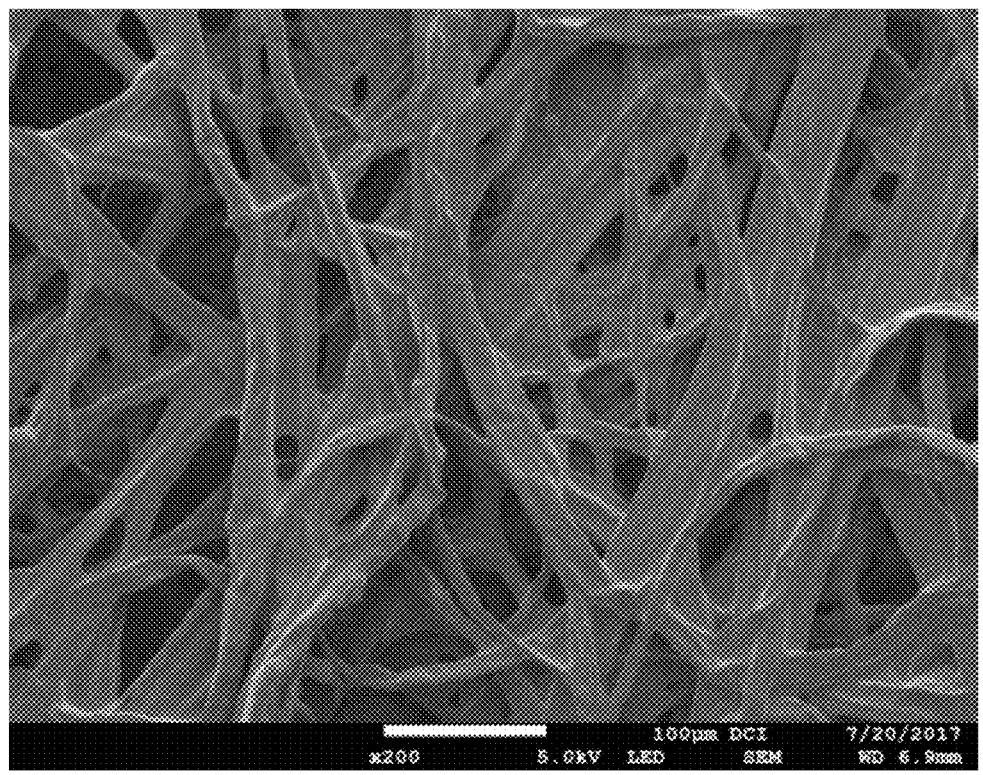
Figure 18C:
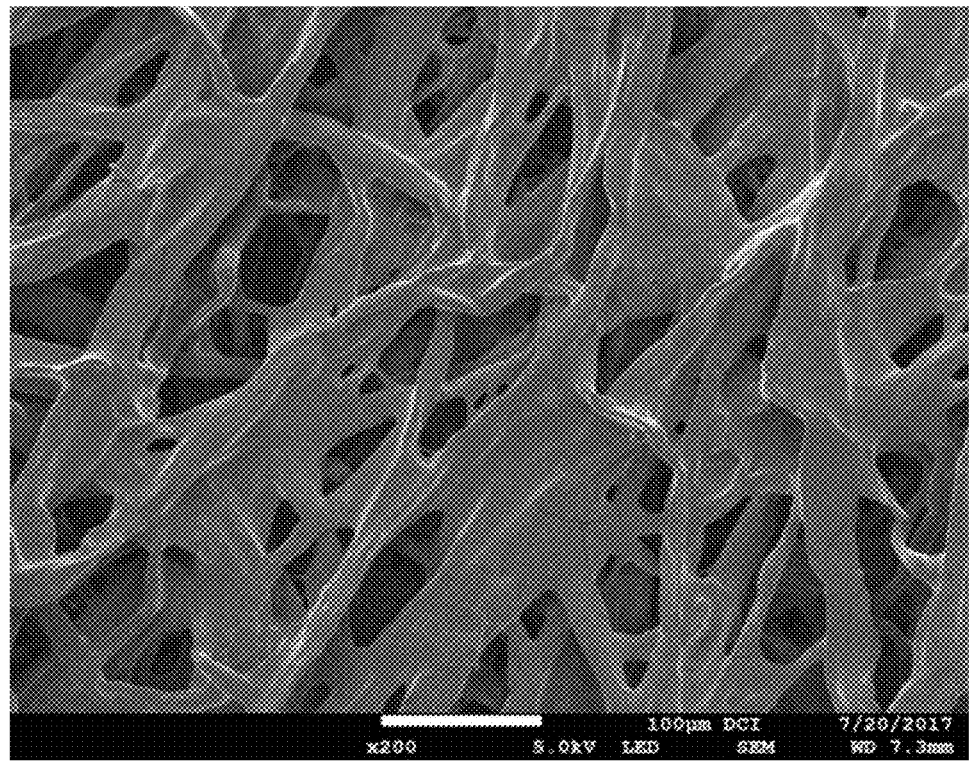
Figure 18D:
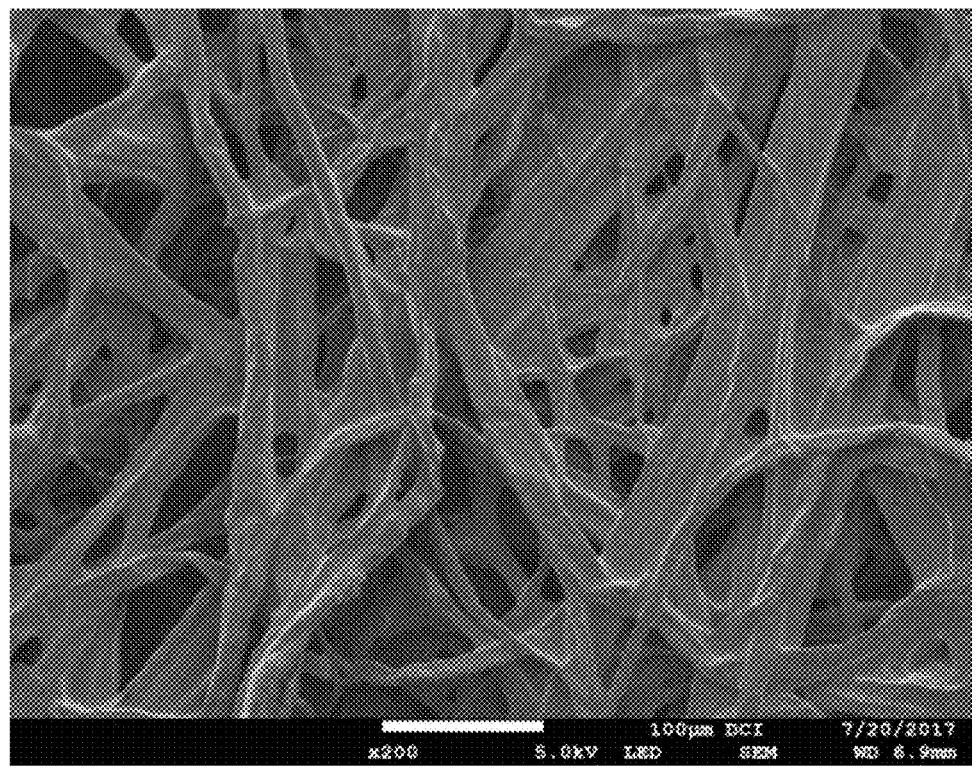

Scanning electron microscopy (SEM) images of Substrate 6 coated with polymers by electrospinning are shown in FIG. 16, FIG. 17, and FIG. 18. As shown in FIG. 16, electrospinning of PHEM forms PHEM nanofibers that coat the cellulose substrate. In contrast, as shown in FIG. 17 and FIG. 18, PEI-10K did not form nanofibers on the substrate but, rather, directly coated the cellulose fibers present in the substrate. These results indicate that a polymer coating created using electrospinning technique may be present in the form of nanofibers or it may be present as a solid polymer coat on a substrate.

TABLE 8

| Polymer solution | Volumetric Flow Rate (ml/min) | Voltage (kV) | Spinning distance (inch) | Spinning time (min) |
|---|---|---|---|---|
| PHEM + methanol | 0.1 | 25 | 5 | 5 |
| PHEM + methanol + DAMO-T | 0.1 | 25 | 5 | 5 |
| PEI + IPA | 0.5 | 20 | 5 | 15 |
| PEI + IPA+ PEGDA | 0.5 | 20 | 5 | 15 |
| PEI + IPA + (3-glycidyloxypropyl)trimethoxy silane | 0.5 | 20 | 5 | 15 |

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A filter media comprising a substrate,
   wherein the substrate comprises a surface having a roll off angle in a range of 40 degrees to 90 degrees and a contact angle in a range of 90 degrees to 180 degrees for a 50 μL water droplet when the surface is immersed in toluene;
   wherein the substrate comprises pores having an average diameter of at least 20 μm; and
   wherein the surface comprises poly(hydroxypropyl methacrylate) (PHPM), poly(2-hydroxyethyl methacrylate) (PHEM), poly(2-ethyl-2-oxazoline) (P2E2O), polyethyleneimine (PEI), quaternized polyethyleneimine, or poly(dopamine), or combinations thereof.

2. The filter media of claim 1, wherein the surface has a roll off angle in a range of 70 degrees to 90 degrees.

3. The filter media of claim 1, wherein the substrate comprises cellulose, polyester, polyamide, polyolefin, glass, or a combination thereof.

4. The filter media of claim 1, wherein the substrate comprises pores having an average diameter in a range of 40 μm to 50 μm.

5. The filter media of claim 1, wherein the substrate is at least 15% porous and up to 99% porous.

6. The filter media of claim 1, wherein the substrate has the ability to retain a roll off angle of at least 80% of an initial roll off angle after being submersed in a hydrocarbon fluid at a temperature of at least 50° C. for at least 1 hour.

7. The filter media of claim 1, wherein the surface comprises poly(hydroxypropyl methacrylate) (PHPM).

8. The filter media of claim 1, wherein the surface comprises poly(2-hydroxyethyl methacrylate) (PHEM).

9. The filter media of claim 1, wherein the surface comprises poly(2-ethyl-2-oxazoline) (P2E2O).

10. The filter media of claim 1, wherein the surface comprises polyethyleneimine (PEI) or quaternized polyethyleneimine, or a combination thereof.

11. The filter media of claim 1, wherein the surface comprises poly(dopamine).

12. A filter element comprising the filter media of claim 1.

13. The filter element of claim 12, wherein the filter element is configured to remove water from a hydrocarbon fluid.

14. The filter element of claim 12, wherein the filter element further comprises a coalescing layer located upstream of the substrate.

15. The filter element of claim 14, wherein the coalescing layer comprises pores having an average diameter and the average diameter of the pores of the substrate is greater than the average diameter of the pores of the coalescing layer.

16. A filter media comprising a substrate,
wherein the substrate comprises a surface having a roll off angle in a range of 40 degrees to 90 degrees and a contact angle in a range of 90 degrees to 180 degrees for a 50 μL water droplet when the surface is immersed in toluene;
wherein the substrate comprises pores having an average diameter of at least 20 μm; and
wherein the surface comprises poly(hydroxypropyl methacrylate) (PHPM).

17. A filter element comprising the filter media of claim 16.

18. A filter media comprising a substrate,
wherein the substrate comprises a surface having a roll off angle in a range of 40 degrees to 90 degrees and a contact angle in a range of 90 degrees to 180 degrees for a 50 μL water droplet when the surface is immersed in toluene;
wherein the substrate comprises pores having an average diameter of at least 20 μm; and
wherein the surface comprises polyethyleneimine (PEI) or quaternized polyethyleneimine, or a combination thereof.

19. A filter element comprising the filter media of claim 18.

20. A filter media comprising a substrate,
wherein the substrate comprises a surface having a roll off angle in a range of 40 degrees to 90 degrees and a contact angle in a range of 90 degrees to 180 degrees for a 50 μL water droplet when the surface is immersed in toluene;
wherein the substrate comprises pores having an average diameter of at least 20 μm; and
wherein the surface is formed by dip coating a polymer solution on the substrate,
wherein the polymer solution comprises a polymer comprising poly(hydroxypropyl methacrylate) (PHPM), poly(2-hydroxyethyl methacrylate) (PHEM), poly(2-ethyl-2-oxazoline) (P2E2O), polyethyleneimine (PEI), quaternized polyethyleneimine, or poly(dopamine), or a combination thereof, and
wherein the polymer solution comprises up to 5% (w/v) of the polymer, based on the molecular weight of the polymer.

* * * * *

UNITED STATES PATENT AND TRADEMARK OFFICE
CERTIFICATE OF CORRECTION

| | |
|---|---|
| PATENT NO. | : 11,207,623 B2 |
| APPLICATION NO. | : 16/425371 |
| DATED | : December 28, 2021 |
| INVENTOR(S) | : Bradly G. Hauser et al. |

It is certified that error appears in the above-identified patent and that said Letters Patent is hereby corrected as shown below:

On the Title Page

On page 2 in item (56) References Cited, '2017/0000223 A1' should be replaced with --2017/0022372 A1--.

Signed and Sealed this
Sixteenth Day of May, 2023

Katherine Kelly Vidal
*Director of the United States Patent and Trademark Office*